(12) United States Patent
Forgacs et al.

(10) Patent No.: US 8,143,055 B2
(45) Date of Patent: Mar. 27, 2012

(54) SELF-ASSEMBLING MULTICELLULAR BODIES AND METHODS OF PRODUCING A THREE-DIMENSIONAL BIOLOGICAL STRUCTURE USING THE SAME

(75) Inventors: Gabor Forgacs, Potsdam, NY (US); Francoise Suzanne Marga, Columbia, MO (US); Cyrille Norotte, Paris (FR)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 12/491,228

(22) Filed: Jun. 24, 2009

(65) Prior Publication Data
US 2010/0041134 A1 Feb. 18, 2010

Related U.S. Application Data

(60) Provisional application No. 61/132,977, filed on Jun. 24, 2008.

(51) Int. Cl.
*C12N 5/071* (2010.01)
(52) U.S. Cl. ........................................ 435/325; 435/395
(58) Field of Classification Search .................. 435/325, 435/395
See application file for complete search history.

(56) References Cited

U.S. PATENT DOCUMENTS

| | | | |
|---|---|---|---|
| 6,979,670 | B1 | 12/2005 | Lyngstadaas et al. |
| 7,051,654 | B2 | 5/2006 | Boland |
| 2002/0188349 | A1 | 12/2002 | McAllister et al. |
| 2003/0153078 | A1 | 8/2003 | Libera et al. |
| 2004/0253365 | A1 | 12/2004 | Warren et al. |
| 2005/0276791 | A1 | 12/2005 | Hansford et al. |
| 2008/0070304 | A1 | 3/2008 | Forgacs et al. |
| 2009/0142307 | A1 | 6/2009 | Athanasiou et al. |

FOREIGN PATENT DOCUMENTS
CA 2 306 346 A1 1/1999

OTHER PUBLICATIONS

International Search Report, PCT/US2009/048530, dated Mar. 15, 2010, 4 Pages.
Kelm, J. M., et al., "Microscale Tissue Engineering Using Gravity-Enforced Cell Assembly," Trends in Biotechnology, Apr. 2004, pp. 195-202, vol. 22, No. 4.
Marga, F., et al., "Developmental Biology and Tissue Engineering," Birth Defects Research (Part C), 2007, pp. 320-328, vol. 81.
Nickerson et al., Three-Dimensional Tissue Assemblies: Novel Models for the Study of *Salmonella enterica* Serovar Typhimurium Pathogenesis; Infection and Immunity, Nov. 2001, vol. 69, No. 11, p. 7106-7120.
Yamauchi et al., A Three-Dimensional Cell Culture Model for Bovine Endometrium: Regeneration of a Multicellular Spheroid Using Ascorbate; Placenta, 2003, vol. 24, p. 258-269.
Furukawa et al., Tissue-Engineered Skin Using Aggregates of Normal Human Skin Fibroblasts and Biodegradable Material J. Artif. Organs (2001); vol. 4; p. 353-356.
Mizumoto et al., Formation of Cylindrical Multicellular Aggregate (Cylindroid) and Expression of Liver Specific Functions of Primary Rate Hepatocytes; Cytotechnology, vol. 31; p. 69-75; 1999.
Constans, A., "Body by Science," The Scientist, Oct. 6, 2003, vol. 17, No. 19, http://www.the-scientist.com/article/display/14154/, 7 pages.
Dai, W., et al., "Fibroblast Aggregation by Suspension with Conjugates of Poly(ethylene glycol) and RGD," Biotechnology and Bioengineering, May 20, 1996, pp. 349-356, vol. 50, No. 4.
Forgacs, G., et al., "Viscoelastic Properties of Living Embryonic Tissues: A Quantitative Study," Biophyisical Journal, May 1998, pp. 2227-2234, vol. 74, No. 5.
Foty, R. A., et al., "Surface Tensions of Embryonic Tissues Predict Their Mutual Envelopment Behavior," Development, 1996, pp. 1611-1620, vol. 122, No. 5.
Foty, R. A., et al., "The Differential Adhesion Hypothesis: A Direct Evaluation," Developmental Biology, 2005, pp. 255-263, vol. 278, vol. 1.
Furukawa, K. S., et al., "Formation of Human Fibroblast Aggregates (Spheriods) by Rotational Culture," Cell Transplantation, 2001, pp. 441-445, vol. 10, No. 4-5.
Glazier, J. A., et al., "Simulation of the Differential Adhesion Driven Rearrangement of Biological Cells," Physical Review E, Mar. 1993, pp. 2128-2154, vol. 47, No. 3.
Glicklis, R., et al., "Modeling Mass Transfer in Hepatocyte Spheroids Via Cell Viability, Spheroid Size, and Hepatocellular Functions," Biotechnology and Bioengineering, Jun. 20, 2004, pp. 672-680, vol. 86, No. 6.
Graner, F., et al., "Simulation of Biological Cell Sorting Using a Two-Dimensional Extended Potts Model," Physical Review Letters, Sep. 28, 1992, pp. 2013-2016, vol. 69, No. 13.
Jakab, K., et al., "Relating Cell and Tissue Mechanics: Implications and Applications," Developmental Dynamics, 2008, pp. 2438-2449, vol. 237.

(Continued)

*Primary Examiner* — Jon P Weber
*Assistant Examiner* — Kailash C Srivastava
(74) *Attorney, Agent, or Firm* — Senniger Powers LLP

(57) ABSTRACT

Structures and methods for tissue engineering include a multicellular body including a plurality of living cells. A plurality of multicellular bodies can be arranged in a pattern and allowed to fuse to form an engineered tissue. The arrangement can include filler bodies including a biocompatible material that resists migration and ingrowth of cells from the multicellular bodies and that is resistant to adherence of cells to it. Three-dimensional constructs can be assembled by printing or otherwise stacking the multicellular bodies and filler bodies such that there is direct contact between adjoining multicellular bodies, suitably along a contact area that has a substantial length. The direct contact between the multicellular bodies promotes efficient and reliable fusion. The increased contact area between adjoining multicellular bodies also promotes efficient and reliable fusion. Methods of producing multicellular bodies having characteristics that facilitate assembly of the three-dimensional constructs are also provided.

19 Claims, 31 Drawing Sheets

OTHER PUBLICATIONS

Jakab, K., et al., "Tissue Engineering by Self-Assembly of Cells Printed into Topologically Defined Structures," Tissue Engineering: Part A, Nov. 3, 2008, pp. 413-421, vol. 14.

Koibuchi, N., et al., "Behavior of Cells in Artificially Made Cell Aggregates and Tissue Fragments after Grafting to Developing Hind Limb Buds in *Xenopus laevis*," The International Journal of Developmental Biology, 1999, pp. 141-148, vol. 43, No. 2.

Korff, T., et al., "Blood Vessel Maturation in a 3-Dimensional Spheroidal Coculture Model: Direct Contact with Smooth Muscle Cells Regulates Endothelial Cell Quiescence and Abrogates VEGF Responsiveness," The FASEB Journal, Feb. 2001, pp. 447-457, vol. 15.

Martin, I., et al., "Computer-Based Technique for Cell Aggregation Analysis and Cell Aggregation in In Vitro Chondrogenesis," Cytometry, 1997, pp. 141-146, vol. 28, No. 2.

Mironov, V., et al., "Organ Printing: Computer-Aided Jet-Based 3D Tissue Engineering," Trends in Biotechnology, Apr. 2003, pp. 157-161, vol. 21, No. 4.

Mironov, V., et al., "Organ Printing: Self-Assembling Cell Aggregates as 'Bioink'," Science & Medicine, Apr. 2003, pp. 69-71, vol. 9, No. 2.

Mironov, V., et al., "Organ Printing: Tissue Spheroids as Building Blocks," Biomaterials, 2009, pp. 2164-2174, vol. 30.

Mombach, J. C. M., et al., "Quantitative Comparison Between Differential Adhesion Models and Cell Sorting in the Presence and Absence of Fluctuations," Physical Review Letters, Sep. 11, 1995, pp. 2244-2247, vol. 75, No. 11.

Ryan, P. L., et al., "Tissue Spreading on Implantable Substrates in a Competitive Outcome of Cell-Cell vs. Cell-Substratum Adhesivity," Proceedings of the National Academy of Sciences, Apr. 10, 2001, pp. 4323-4327, vol. 98, No. 8.

"Sciperio, Inc. 2003 R&D 100 Award Winner," Sciperio, http://www.sciperio.com/news/20031016.asp, accessed on Feb. 1, 2005, 2 pages.

Steinberg, M. S., "Does Differential Adhesion Govern Self-Assembly Processes in Histogenesis? Equilibrium Configurations and the Emergence of a Hierarchy Among Populations of Embryonic Cells," The Journal of Experimental Zoology, Apr. 1970, pp. 395-433, vol. 173, No. 4.

Steinberg, M. S., "Liquid Behavior of Embryonic Tissues," Cell Behavior, 1982, pp. 583-697.

Stiles, E., "UA Wins R & D 100 Award for Machine that Prints Tissue Cell-by-Cell," UANews, Dec. 2, 2003, http://uanews.org/cgi-bin/WebObjects/UANews.woa/wa/goPrint?ArticleID=8305, accessed on Feb. 1, 2005, 2 pages.

Timmins, N. E., et al., "Hanging-Drop Multicellular Spheroids as a Model of Tumour Angiogenesis," Angiogenesis, 2004, pp. 97-103, vol. 7, No. 2.

Tang, M. D., et al., "Molding of Three-Dimensional Microstructures of Gels," Journal of the American Chemical Society, Oct. 29, 2003, pp. 12988-12989, vol. 125, No. 43.

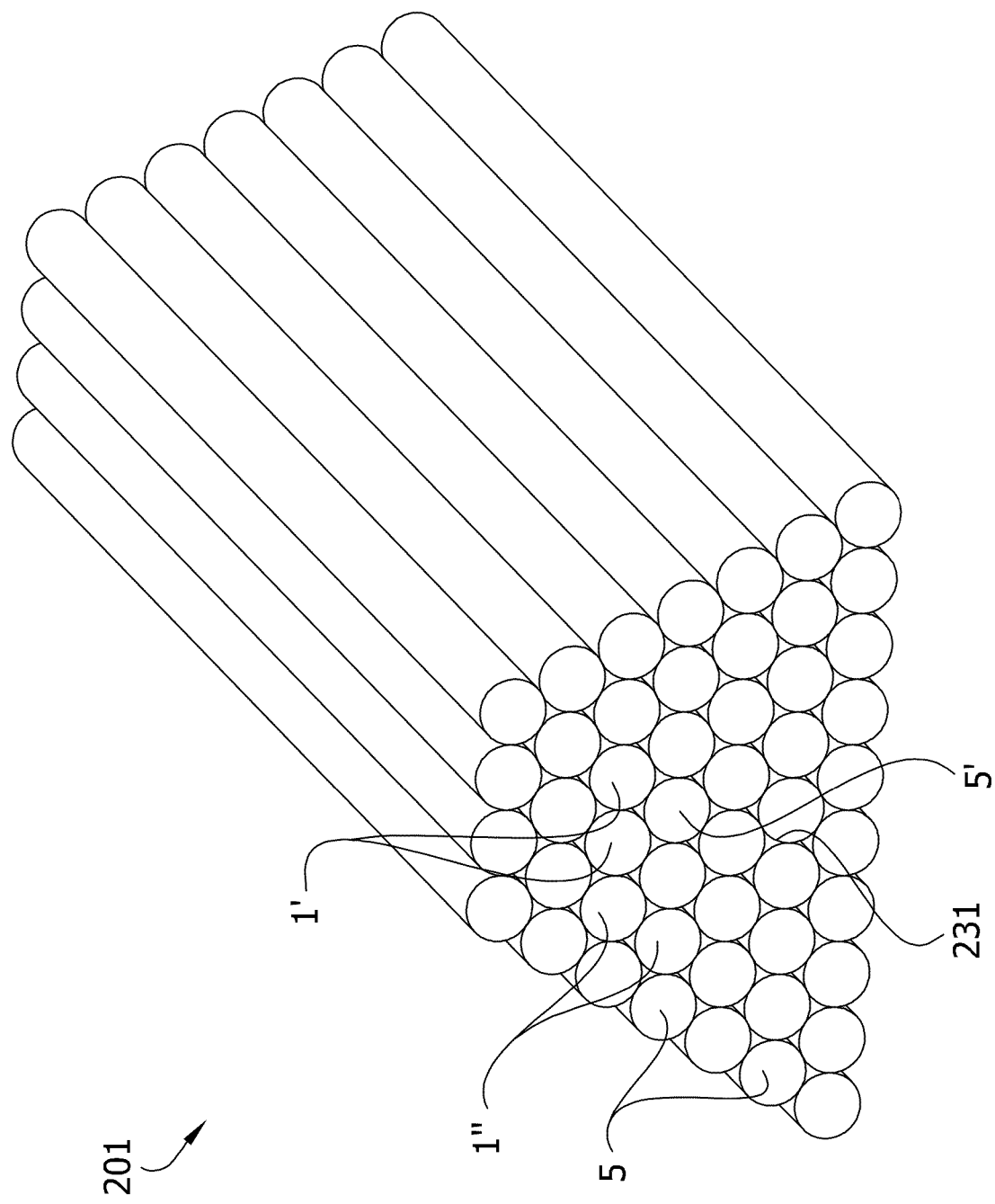

US 8,143,055 B2

SELF-ASSEMBLING MULTICELLULAR BODIES AND METHODS OF PRODUCING A THREE-DIMENSIONAL BIOLOGICAL STRUCTURE USING THE SAME

GRANT STATEMENT

The invention was made in part from government support under Grant No. NSF-0526854 from the National Science Foundation. The U.S. Government has certain rights in the invention.

FIELD OF THE INVENTION

The present invention relates to the field of regenerative medicine and tissue engineering, and more particularly to production of engineered tissues/organs having desired structures.

BACKGROUND

Tissue engineering provides promising solutions to problems caused by the growing demand for organ and tissue replacement coupled with a chronic shortage of transplantable organs, including blood vessels. In the United States, for example, thousands of people are on the national waiting list for organ transplants. Many will likely perish for lack of replacement blood vessels for diseased arteries or veins or replacement abdominal organs. To lessen and eventually solve the problem of inadequate supply of blood vessels and organs for transplantation, tissue engineers strive to build and grow transplantable blood vessels, blood vessel substitutes, organs, or organ substitutes in a laboratory, with high precision, on large scale, and in a relatively short amount of time.

A variety of methods to build engineered tissues have been attempted and developed with limited success. However, assembly of vascularized three-dimensional organs has not been accomplished.

Prior art solutions, though promising, have presented a number of challenges. Scaffold choice, immunogenicity, degradation rate, toxicity of degradation products, host inflammatory responses, fibrous tissue formation due to scaffold degradation, and mechanical mismatch with the surrounding tissue may affect the long term behavior of the engineered tissue construct and directly interfere with its primary biological function. For example, myocardial tissue requires high cell density to assure synchronous beating through gap junctions that tightly interconnect neighboring cells. The use of scaffolds in cardiac tissue engineering has been associated with reduced cell-to-cell connection, as well as incorrect deposition and alignment of extracellular matrix (ECM; e.g., collagen and elastin), affecting scaffold biodegradation and the force-generating ability of myocardial constructs. ECM-related factors are also particularly critical in vascular tissue engineering. Largely for this reason the promise of a scaffold-engineered small-diameter blood vessel substitute with mechanical strength comparable to native vessels for adult arterial revascularization, often described as the "holy grail" of tissue-engineering, remains unfulfilled. Besides the recurrent difficulty of producing elastic fibers in vitro, the use of scaffolds presents additional problems. The inherent weakness of the gels may hinder the final strength of the tissue-engineered vessel. In addition, the presence of residual polymer fragments can disrupt the normal organization of the vascular wall and even influence smooth muscle cell (SMC) phenotype. Therefore it is not surprising that the first clinical applications of tissue-engineered vascular grafts have either targeted low-pressure applications or relied on an entirely scaffold-free method termed sheet-based tissue-engineering.

Organ printing, especially the technique described in U.S. patent application Ser. No. 10/590,446, has shown promise for producing three-dimensional tissues. Organ printing is generally a computer-aided, dispenser-based, three-dimensional tissue-engineering technology aimed at constructing functional organ modules and eventually entire organs layer-by-layer. In the technology described in U.S. patent application Ser. No. 10/590,446, individual multicellular aggregates are printed into a gel or other support matrix. The final functional tissue results form the post-printing fusion of the individual aggregates.

SUMMARY OF THE INVENTION

One aspect of the invention is an elongate multicellular body. The body includes a plurality of living cells and tissue culture medium. The cells are cohered to one another. The multicellular body has a length of at least about 1000 microns and an average cross-sectional area along its length in the range of about 7,850 square microns to about 360,000 square microns.

Another aspect of the invention is an engineered elongate multicellular body. The body includes a plurality of living cells that are cohered to one another. The multicellular body has a length of at least about 1000 microns and an average cross-sectional area along its length in the range of about 7,850 square microns to about 360,000 square microns.

Another embodiment is a non-innervated and non-cartilaginous elongate multicellular body. The body includes a plurality of living cells that are cohered to one another. The multicellular body has a length of at least about 1000 microns and an average cross-sectional area along its length in the range of about 7,850 square microns to about 360,000 square microns.

A further aspect of the invention is a lumenless elongate multicellular body. The body includes a plurality of living cells and tissue culture medium. The cells are cohered to one another. The multicellular body has an aspect ratio that is at least about 2.

In one aspect of the invention, a multicellular body made of a plurality of cells or cell aggregates in a desired three-dimensional shape with viscoelastic consistency is described. The multicellular body comprises a plurality of cells or cell aggregates, wherein the cells or cell aggregates cohere together to form a construct in a pre-determined shape with viscoelastic consistency, desired cell density, and sufficient integrity for easy manipulation and handling.

Yet another aspect of the invention is a method of producing an elongate multicellular body that includes a plurality of living cells. A cell paste including a plurality of living cells is shaped into an elongate shape. The shaped cell paste is incubated in a controlled environment to allow the cells to cohere to one another to form the elongate multicellular body.

Another method of producing a multicellular body including a plurality of living cells according to the invention includes shaping a cell paste that includes a plurality of living cells in a device that holds the cell paste in a three-dimensional shape. The shaped cell paste is incubated a controlled environment while it is held in said three-dimensional shape for a sufficient time to produce a body that has sufficient cohesion to support itself on a flat surface.

Also provided is a method of producing an elongate multicellular body comprising a plurality of living cells. The method comprises shaping a cell paste comprising a plurality of living cells into an elongate shape, and incubating the shaped cell paste in a controlled environment to allow the cells to cohere to one another to form the elongate multicellular body. In this aspect of the invention, a method for producing an elongate multicellular body, which comprises a plurality of cells or cell aggregates in a pre-determined shape with viscoelastic consistency, is described. In one embodiment, the method to produce a multicellular body comprises the steps of: 1) providing a cell paste containing a plurality of pre-selected cells or cell aggregates with a desired cell density and viscosity, 2) manipulating the cell paste into desired shape, and 3) forming the multicellular body through maturation.

In yet another aspect of the invention, a filler body which is used in combination with the aforesaid multicellular body to build a desired three-dimensional biological construct, is described. The filler body comprises a material in a pre-determined shape, where the material resists the in-growth, migration, and adherence of cells, and can also be permeable to tissue culture media (i.e., permeable to nutrients). The filler body may be made of material such as agarose, agar, and/or other hydrogels. During the construction of a biological construct, the filler bodies are employed, according to a pre-determined pattern, to define domains void of the multicellular bodies.

In another aspect of the invention, a method of forming the filler bodies is described. In general, the method is to prepare (e.g., manipulate) a pre-selected suitable material in a gel-like condition into a desired shape. According to one embodiment of the inventive method, the fabrication method may further include the steps of: 1) lowering the viscosity of the material to liquid-like material, 2) shaping the liquid-like material with a pre-determined shape, and 3) raising the viscosity of the material into that of the desired gel-like filler matrix unit.

Yet another embodiment of the invention is a three-dimensional structure including a plurality of non-innervated elongate multicellular bodies. Each multicellular body includes a plurality of living cells cohered to one another. The multicellular bodies are arranged in a pattern in which each multicellular body contacts at least one other multicellular body and the multicellular bodies are not cohered to one another.

A further aspect of the invention is a three-dimensional structure. The structure includes a plurality of engineered elongate multicellular bodies. Each multicellular body includes a plurality of living cells cohered to one another. The multicellular bodies are arranged in a pattern in which each multicellular body contacts at least one other multicellular body and the multicellular bodies are not cohered to one another.

In another embodiment, a three-dimensional structure includes a plurality of elongate multicellular bodies. Each multicellular body includes a plurality of living cells cohered to one another and tissue culture medium. The multicellular bodies are arranged in a pattern in which each multicellular body contacts at least one other multicellular body and the multicellular bodies are not cohered to one another.

In yet another embodiment, a three-dimensional structure includes a plurality of non-innervated multicellular bodies. Each multicellular body includes a plurality of living cells cohered to one another. The multicellular bodies are arranged in a pattern in which at least one of the multicellular bodies contacts another of the multicellular bodies along a contact area having a length that is at least about 1000 microns.

In another aspect of the invention, a three-dimensional structure includes a plurality of engineered multicellular bodies. Each multicellular body includes a plurality of living cells cohered to one another. The multicellular bodies are arranged in a pattern in which at least one of the multicellular bodies contacts another of the multicellular bodies along a contact area having a length that is at least about 1000 microns.

In yet another embodiment of the invention a three-dimensional structure includes a plurality of multicellular bodies. Each multicellular body includes a plurality of living cells cohered to one another and tissue culture medium. The multicellular bodies are arranged in a pattern in which at least one of the multicellular bodies contacts another of the multicellular bodies along a contact area having a length that is at least about 1000 microns.

Another embodiment of a three-dimensional structure includes a plurality of multicellular bodies. Each multicellular body includes a plurality of living cells cohered to one another. The structure also includes a plurality of discrete filler bodies. Each filler body includes a biocompatible material that resists migration and ingrowth of cells from the multicellular bodies into the filler bodies and resists adherence of cells in the multicellular bodies to the filler bodies. The multicellular bodies and filler bodies are arranged in a pattern in which each multicellular body contacts at least one other multicellular body or at least one filler body.

Another further aspect of the invention is a three-dimensional structure including a plurality of multicellular bodies. Each multicellular body includes a plurality of living cells cohered to one another. The structure also includes a plurality of filler bodies. Each filler body includes a biocompatible material that resists migration and ingrowth of cells from the multicellular bodies into the filler bodies and resists adherence of cells in the multicellular bodies to the filler bodies. The multicellular bodies and the filler bodies are arranged to form a plurality of spaces in the three dimensional structure that are not occupied by the multicellular bodies and that are not occupied by the filler bodies.

Yet another aspect of the invention is a method of producing a three-dimensional biological engineered tissue. The method includes arranging a plurality of elongate multicellular bodies according to a pattern such that each of the multicellular bodies contacts at least one other multicellular body. Each multicellular body includes a plurality of living cells. At least one of the multicellular bodies is allowed to fuse with at least one other multicellular body.

In another embodiment of a method of producing a three-dimensional biological engineered tissue, a plurality of multicellular bodies and a plurality of filler bodies are arranged according to a pattern such that each of the multicellular bodies contacts at least one of (i) another multicellular body or (ii) a filler body. Each multicellular body includes a plurality of living cells. Each filler body includes a biocompatible material that resists migration and ingrowth of cells from the multicellular bodies into the biocompatible material and resists adherence of cells in the multicellular bodies to the filler bodies. At least one of the multicellular bodies is allowed to fuse with at least one other multicellular body.

In yet another embodiment of a method of producing a three-dimensional biological engineered tissue, the method is to deliver a plurality of multicellular bodies into a pre-determined pattern in a pre-selected receiving environment. According to one embodiment of the engineering method, the multicellular bodies may be employed in combination with the pre-selected filler bodies. More particularly, in one embodiment, the method includes the steps of: 1) delivering the plurality of multicellular bodies in a pre-determined combination with a plurality of filler bodies according to the pre-determined pattern to form a stacked or layered construct, where the multicellular bodies and the filler bodies are contiguous, 2) depositing the layered construct into a pre-selected controlled environment for maturation, whereby the multicellular bodies fuse with each other to result in a fused construct, and 3) removing the filler bodies from the fused construct to produce the desired biological construct.

Another embodiment of the invention is a three-dimensional structure including at least one filler body and a plurality of living cells which are cohered to one another. The cells form a tubular structure substantially surrounding the at least one filler body. The filler body includes a compliant biocompatible material that resists migration and ingrowth of cells into the material and which resists adherence of cells to the material.

Still another aspect of the invention is a mold for producing a multicellular body comprising a plurality of living cells cohered to one another. The mold has biocompatible substrate that is resistant to migration and ingrowth of cells into the substrate and resistant to adherence of cells to the substrate. The substrate is shaped to receive a composition comprising plurality of cells having a relatively lower cohesion and hold the composition in a desired shape during a maturation period during which the cohesion increases to form the multicellular body. The desired shape of the multicellular body has a length of at least about 1000 microns and is configured so every cell within the multicellular body is no more than about 250 microns from an exterior of the body.

Another embodiment of the invention is a tool for making a mold that is suitable for producing a plurality of multicellular bodies in which each body includes a plurality of living cells cohered to one another. The tool has a a body having a top and a bottom. A plurality of fins extend from the bottom of the body. Each of the fins has a width in the range of about 100 microns to about 800 microns for forming grooves in a biocompatible gel substrate configured for forming living cells placed in the grooves into elongate multicellular bodies. The fins have longitudinal axes and at least one of the fins is spaced laterally from the longitudinal axis of another of the fins.

BRIEF DESCRIPTION OF THE DRAWINGS

FIGS. 7, 7A, and 8-10 are schematic perspectives of various embodiments of three-dimensional constructs made from a plurality of multicellular bodies and a plurality of filler bodies;

Corresponding reference characters indicate corresponding parts throughout the drawings.

DETAILED DESCRIPTION

Figure 1A:
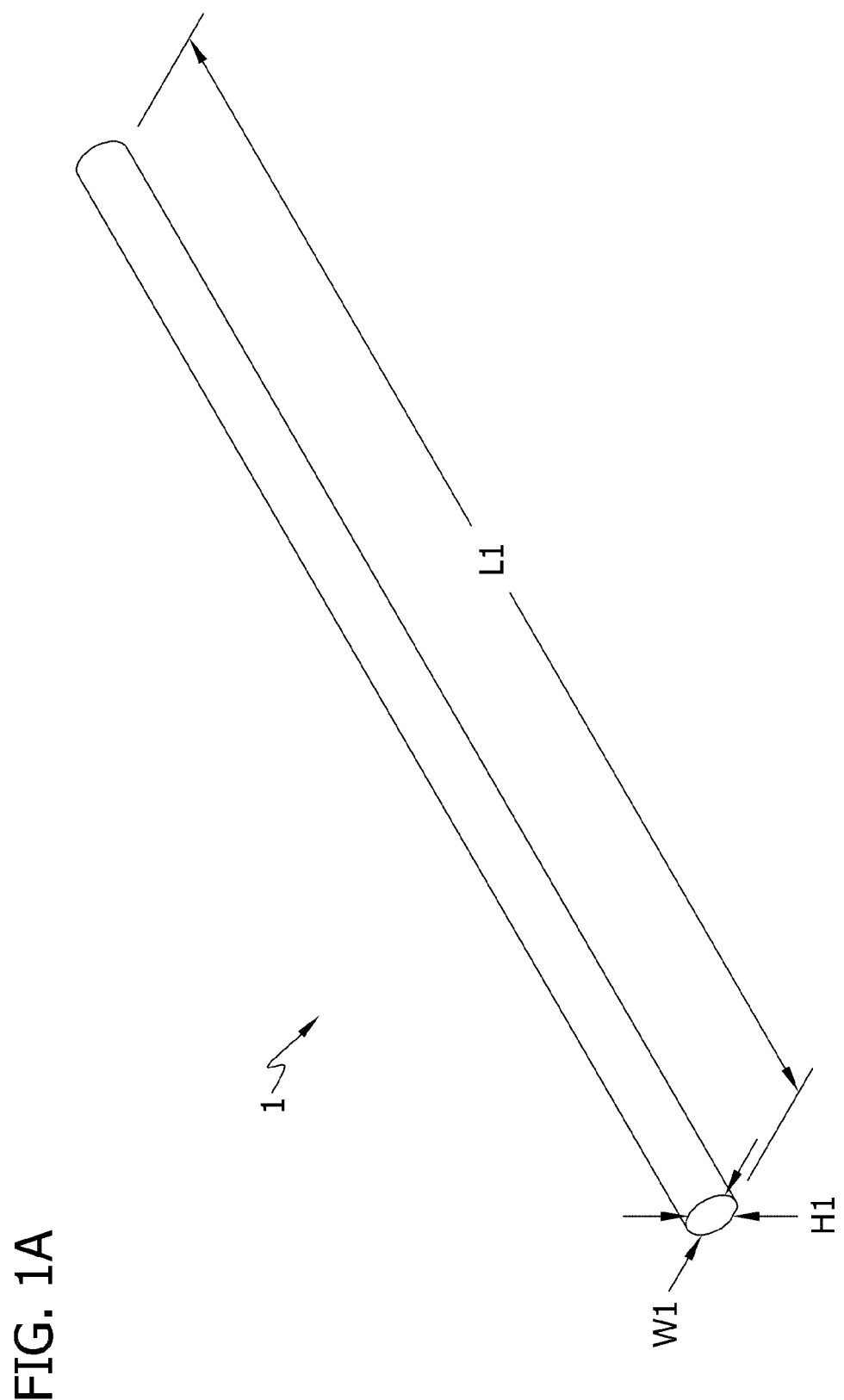
FIG. 1A is a perspective of one embodiment of a multicellular body of the present invention.

All publications, patent applications, patents, and other references mentioned herein are incorporated by reference in their entirety.

New structures and methods for producing engineered tissue are provided. The technology involves use of novel multicellular bodies as building blocks that can be used to assemble a three-dimensional construct that can become a desired engineered tissue through maturation. Each multicellular body comprises a plurality of living cells that are sufficiently cohered to one another to allow the body to be handled (e.g., picked up and moved) as a single object. The cohesion of the multicellular body is suitably sufficient to allow the body to support itself (e.g., on a work surface or in an assembly that includes multiple multicellular bodies) for a period of time sufficient to enable the living cells to cohere to the living cells of an adjoining multicellular body. The ability to pick up and move a plurality of living cells in the form of a self-supporting multicellular body provides flexibility to assemble numerous different three-dimensional constructs. For example, the multicellular bodies can be used in conjunction with one or more filler bodies (e.g., bodies comprising a biocompatible material that resists migration and ingrowth of cells from the multicellular bodies into the filler bodies and resists adherence of cells to the filler bodies) to assemble constructs that can become a tubular engineered tissue through maturation. The multicellular bodies and filler bodies can also be used to assemble constructs that become engineered tissues having other shapes through maturation. Further, because the multicellular bodies are self-supporting, there is no need to embed the multicellular bodies in a supporting gel or scaffold. Instead, the ability to "print in air" facilitates arranging the multicellular bodies in a manner that ensures the multicellular bodies are in direct contact with one another. Better contact between the multicellular bodies can facilitate efficient and reliable fusion of the multicellular bodies during maturation. In addition, the filler bodies can be easily removed from the exterior and interior (e.g. the lumen of a tubular structure) of a mature engineered tissue.

In addition, some of the methods of the present invention use elongate multicellular bodies as the building blocks for the engineered tissue. Because elongate multicellular bodies are already cohered to one another over a significant length along a longitudinal axis of the body, fusion of the multicellular bodies is more reliable and can be achieved in less time. Further, elongate multicellular bodies can be arranged in side-by-side adjoining relation to establish contact between the multicellular bodies along a contact area having a substantial length. This can facilitate rapid and reliable fusion of the adjoining multicellular bodies to one another.

Having provided a general overview of a method of producing a three-dimensional biological engineered tissue using the materials and processes of the present invention, such processes and materials will now be described in more detail.

Multicellular Bodies

One embodiment of a multicellular body (also referred to herein as an intermediate cellular unit), generally designated 1, is illustrated in FIG. 1. The multicellular body 1 includes a plurality of living cells that are cohered to one another. The multicellular body 1 comprises a plurality of cells cohered together in a desired three-dimensional (3-D) shape with viscoelastic consistency and sufficient integrity for easy manipulation and handling during a bio-engineering process, such as tissue or organ engineering. Sufficient integrity means that the multicellular body, during the subsequent handling, is capable of retaining its physical shape, which is not rigid, but has a viscoelastic consistency, and maintaining the vitality of the cells.

The multicellular body 1 may be composed of any one or more pre-selected cell types. In general, the choice of cell type will vary depending on the desired three-dimensional biological tissue. For example, if the multicellular body is to be used to engineer a blood vessel-type three-dimensional structure, the cells used to form the multicellular bodies can advantageously comprise a cell type or cell types typically found in vascular tissue (e.g., endothelial cells, smooth muscle cells, fibroblasts, etc.). Other cell types may be used to form the multicellular body if it is to be used to engineer a different type of three-dimensional tissue (e.g., intestine, liver, kidney, etc.). One skilled in the art will be able to choose an appropriate cell type or types for the multicellular body based on the type of three-dimensional tissue to be engineered. Non-limiting examples of suitable cell types include contractile or muscle cells (e.g., striated muscle cells, including myoblasts and cardiomyocytes, and smooth muscle cells), neural cells, fibroblasts, connective tissue cells (including the cell types which make up bone and cartilage, cells capable of differentiating into bone forming cells and chondrocytes, and cell types which make up lymph tissues), parenchymal cells, epithelial cells (including endothelial cells that form linings in cavities and vessels or channels, exocrine and endocrine secretory epithelial cells, epithelial absorptive cells, keratinizing epithelial cells, and extracellular matrix secretion cells), hepatocytes, and undifferentiated cells (such as embryonic cells, stem cells, and other precursor cells), among others. For example, the cells used to form the multicellular body 1 can be obtained from a live human or animal subject and cultured as a primary cell line.

The multicellular body 1 may be homocellular or heterocellular. In homocellular multicellular bodies, the plurality of living cells includes a plurality of living cells of a single cell type. Almost all of the living cells in a homocellular multicellular body are cells of the single cell type, subject to some tolerance for low levels of impurities including a relatively small number of cells of a different cell type that have no more than a negligible impact on the maturation of a construct including the homocellular multicellular body.

In contrast, a heterocellular multicellular body includes significant numbers of cells of more than one cell type. For example, a multicellular body can comprise a plurality of living cells of a first type and a plurality of living cells of a second type (etc.), the second cell type being different from the first cell type. If the multicellular bodies are to be used to create vascular tissue, for instance, the cells of the first type can be endothelial cells and the cells of the second type can be smooth muscle cells, the cells of the first type can be endothelial cells and the cells of the second type can be fibroblasts, or the cells of the first type can be smooth muscle cells and the cells of the second type can be fibroblasts. Heterocellular multicellular bodies can also include a plurality of cells of a first cell type, a plurality of cells of a second cell type, and a plurality of cells of a third cell type with each of the first, second and third cell types being different from the others of the first, second, and third cells types. For example, a multicellular body that is suitable for producing an engineered blood vessel can include endothelial cells, smooth muscle cells, and fibroblasts. The living cells in a heterocellular body may remain unsorted or can "sort out" (e.g., self-assemble) during the fusion process to form a particular internal structure for the engineered tissue. The self sorting of cells is consistent with the predictions of the Differential Adhesion Hypothesis (DAH). The DAH explains the liquid-like behavior of cell populations in terms of tissue surface and interfacial tensions generated by adhesive and cohesive interactions between the component cells. In general, cells can sort based on differences in the adhesive strengths of the cells. For example, cell types that sort to the center of a heterocellular multicellular body generally have a stronger adhesion strength (and thus higher surface tension) than cells that sort to the outside of the multicellular body.

Furthermore, when a heterocellular multicellular body is composed of cells from tissues that are neighbors in normal development, in the course of sorting they may recover their physiological conformation. Thus, heterocellular multicellular bodies may comprise a sort of pre-built internal structure, based on the adhesive and cohesive properties of the component cells, and the environment in which the cells are located. This can be used to build more complex biological structures. For example, while building a simple contractile tube, homocellular multicellular bodies composed of muscle cells can be used; to build a blood vessel-like structure, at least two cell types can be used. For example, a heterocellular multicellular body to be used for building an engineered blood vessel can suitably include (i) endothelial cells and smooth muscle cells; (ii) smooth muscle cells and fibroblasts; (iii) endothelial cells and fibroblasts; or (iv) endothelial cells, smooth muscle cells, and fibroblasts. By using multicellular bodies composed of these multiple different cell types randomly dispersed in the body to build a three-dimensional biological structure, in the course of structure formation the different cell types can sort out so endothelial cells line the internal structure of the tube (i.e., the lumen), smooth muscle cells form a layer surrounding the endothelial cells, and the fibroblasts form an outer layer surrounding the smooth muscle layer. The optimal structure can be achieved by varying the composition of the multicellular body (e.g., ratios of the various different cell types to one another) and by size of the multicellular body. As another example, heterocellular multicellular bodies can include a plurality of living cells of a first cell type, a plurality of cells of a second type, and a plurality of cells of a third type. If such multicellular bodies are to be used to create vascular tissue, for instance, the cells of the first cell type can suitably be endothelial cells, the cells of the second cell type can suitably be smooth muscle cells, and the cells of the third cell type can suitably be fibroblasts. Again, self-sorting of the cells may occur in such heterocellular multicellular bodies. Thus, when these multicellular bodies are used to build a three-dimensional biological structure, for example a tubular structure, in the course of structure formation these cell types may sort such that the endothelial cells line the internal structure of the tube (i.e., the lumen), the smooth muscle cells form a layer substantially surrounding the endothelial cells, and the fibroblasts form the outer layer of the tubular structure, substantially surrounding both the layer of endothelial cells and the layer of smooth muscle cells.

In some instances, the multicellular body 1 suitably includes one or more extracellular matrix (ECM) components or one or more derivatives of one or more ECM components in addition to the plurality of cells. For example, the multicellular bodies may contain various ECM proteins (e.g., gelatin, fibrinogen, fibrin, collagen, fibronectin, laminin, elastin, and/or proteoglycans). The ECM components or derivatives of ECM components can be added to a cell paste used to form the multicellular body, as discussed in further detail below. The ECM components or derivatives of ECM components added to the cell paste can be purified from a human or animal source, or produced by recombinant methods known in the art. Alternatively, the ECM components or derivatives of ECM components can be naturally secreted by the cells in the multicellular body, or the cells used to make the multicellular body can be genetically manipulated by any suitable method known in the art to vary the expression level of one or more ECM components or derivatives of ECM components and/or one or more cell adhesion molecules or cell-substrate adhesion molecules (e.g., selectins, integrins, immunoglobulins, and cadherins). The ECM components or derivatives of ECM components may promote cohesion of the cells in the multicellular body. For example, gelatin and/or fibrinogen can suitably be added to the cell paste which is used to form the multicellular body. The fibrinogen can then be converted to fibrin by the addition of thrombin.

As noted above, the multicellular body 1 in some instances suitably includes a tissue culture medium. The tissue culture medium can be any physiologically compatible medium and will typically be chosen according to the cell type(s) involved as is well known in the art. The tissue culture medium may comprise, for example, basic nutrients such as sugars and amino acids, growth factors, antibiotics (to minimize contamination), etc.

The cohesion of the cells in the multicellular body 1 is suitably sufficiently strong to allow the multicellular body to retain a three-dimensional shape while supporting itself on a flat surface. In FIG. 1B, for instance, the multicellular body 1 is supporting itself on a flat surface 13. Although there is some minor deformation (e.g., where the multicellular body 1 contacts the surface 13), the multicellular body is sufficiently cohesive to retain a height that is suitably at least one half its width, and more suitably about equal to the width. Also as illustrated in FIG. 1B, for example, the multicellular body 1 is supported by a flat exterior surface 15 formed on the bottom of the multicellular body by contact between the multicellular body and the surface 13. When the full weight of the multicellular body 1 is supported by the surface 13, the area A1 of the contact surface 15 may be larger than the initial contact area due to slight deformation of the multicellular body. However, the area A1 of the contact surface 15 is suitably smaller than the area A2 of a two dimensional projection of the multicellular body 1 onto the support surface 13 (See FIG. 1B). This means that a portion of the multicellular body 1 (e.g., each of the sides as illustrated in FIG. 1B) is supported by the multicellular body 1 above the work surface 13. Likewise, when two or more of the multicellular bodies 1 are placed in side-by-side adjoining relation to one another on the flat surface 13 (FIG. 1C), their self-supporting abilities in combination with the three-dimensional shape in which they retain themselves can form a void space 17 under their sides and above the work surface.

The cohesion of the cells in the multicellular body 1 is also suitably sufficiently strong to allow the multicellular body to support the weight of at least one similarly sized and shaped multicellular body or filler body when the multicellular body is assembled in a construct in which the multicellular bodies and filler bodies are stacked on top of one another (See FIG. 2, discussed in more detail below). The cohesion of the cells in the multicellular body 1 is also suitably sufficiently strong to allow the multicellular body to be picked up by an implement (e.g., a capillary micropipette) (See FIG. 3D, discussed in more detail below).

Furthermore, the multicellular body 1 can suitably be non-innervated (i.e., it is substantially free of neurons) or non-cartilaginous, or both non-innervated and non-cartilaginous. The multicellular body can be described as an "engineered" multicellular body because it is different from biological structures that arise without the guidance of human ingenuity. In other words, the multicellular body is synthetic, or non-naturally occurring.

The multicellular body 1 can have various sizes and shapes within the scope of the invention. For example, the multicellular body 1 illustrated in FIG. 1 is a lumenless body, meaning that there is no open passage extending through the multicellular body. For example, the multicellular body 1 suitably has substantially no voids, hollow spaces or the like within the body. This is one difference between the multicellular body 1 illustrated in FIG. 1 and prior art engineered blood vessels and other prior art tubular engineered tissues.

Figure 1B:
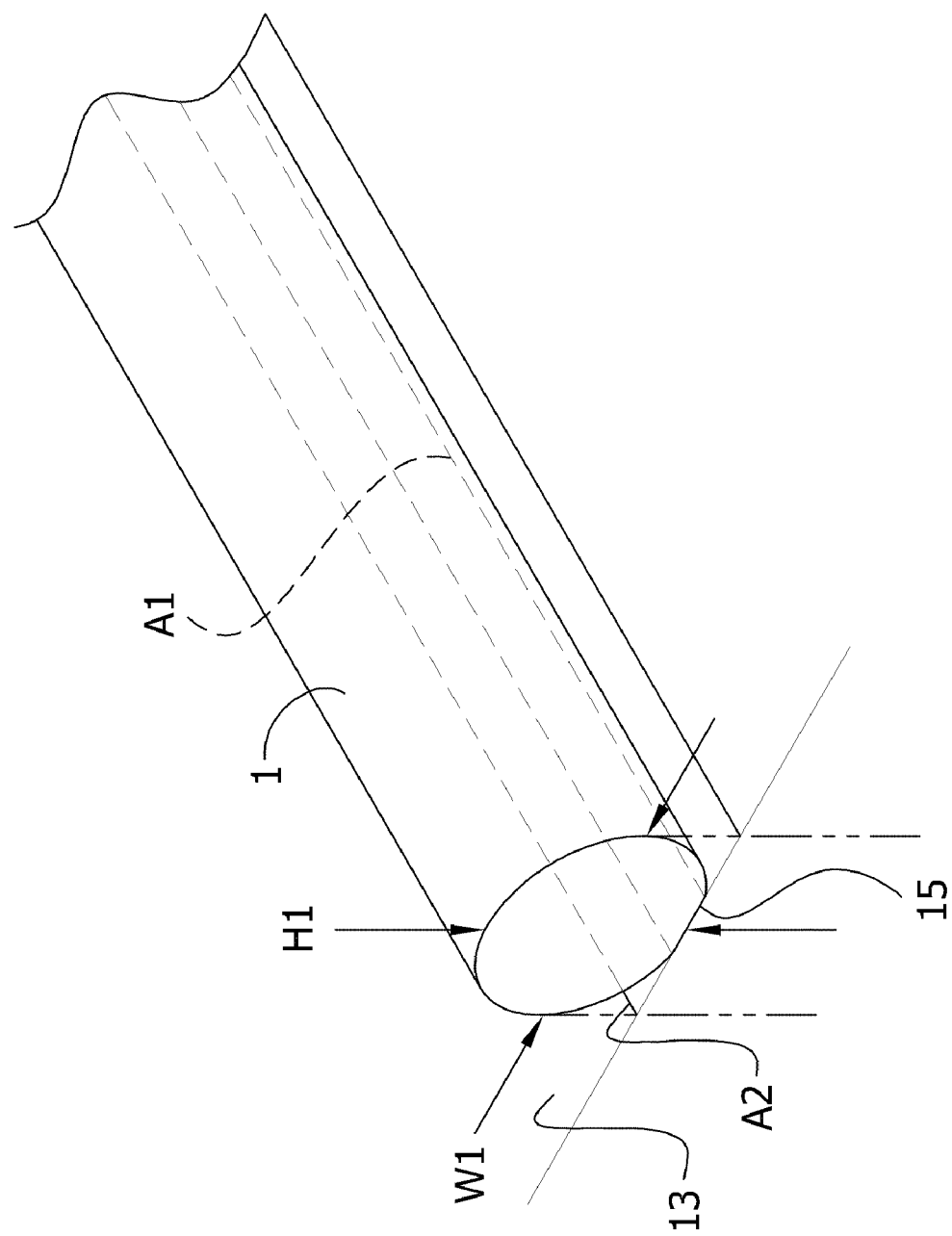
FIG. 1B is an enlarged perspective of the multicellular body supported by a surface.

The multicellular body 1 illustrated in FIG. 1A-1B is configured to limit cell necrosis caused by inability of oxygen and/or nutrients to diffuse into central portions of the multicellular body. For example, the multicellular body 1 is suitably configured so none of the living cells therein is more than about 250 microns from an exterior surface of the multicellular body, and more suitably so none of the living cells therein is more than about 200 microns from an exterior of the multicellular body. Because of the proximity of the cells in the central portions of the multicellular body 1 to the exterior surface of the multicellular body, cells in the multicellular body can be supplied with oxygen and/or nutrients by diffusion thereof from a void space at the exterior surface of the multicellular body toward the central portions of the body. Although there may be some necrosis of cells in one or more portions of the multicellular body (e.g., the central portion), the necrosis is limited.

The multicellular body 1 in FIG. 1 is also an elongate body having a length L1 that is significantly larger than its height H1 and its width W1. The length L1 of the multicellular body 1 is suitably at least about 1000 microns (e.g., in the range of about 1000 microns to about 30 centimeters), more suitably at least about 1 centimeter (e.g., in the range of about 1 centimeter to about 30 centimeters), still more suitably at least about 5 centimeters (e.g., in the range of about 5 centimeters to about 30 centimeters). There is no theoretical upper limit on the length L1 of the multicellular body. Thus, it is recognized that it is possible to make a multicellular body having a length in excess of 30 centimeters (or any arbitrary length different from 30 centimeters) within the scope of the invention as long as a person is willing to overcome practical difficulties associated with making a long multicellular body, such as obtaining a sufficient quantity of living cells or handling a long multicellular body etc.

The height H1 and width W1 of the elongate multicellular body 1 illustrated in FIG. 1 are suitably significantly less than its length L1. For example, the length L1 is suitably at least twice the width W1 and at least twice the height H1, meaning the body 1 has an aspect ratio (i.e., the ratio of the length to the longest dimension orthogonal to the length) that is at least about 2, more suitably at least about 10 and still more suitably at least 20. It will be noted from the description of the dimensions of the multicellular body 1 above that the aspect ratio can also be considerably higher than 20 within the scope of the invention; for example the aspect ratio can be 2000.

The multicellular body 1 illustrated in FIG. 1 also has a relatively narrow width W1 and a relatively short height H1. For example, the average cross-sectional area of the multicellular body 1 along its length L is suitably in the range of about 7,850 square microns to about 360,000 square microns, more suitably in the range of about 31,400 square microns to about 250,000 square microns, and still more suitably in the range of about 31,400 square microns to about 90,000 square microns. For another example, the multicellular body 1 illustrated in FIG. 1 (which is substantially cylindrical and has a circular cross section) suitably has an average diameter along its length in the range of about 100 microns to about 600 microns (corresponding to an average cross-sectional area in the range of about 7,850 square microns to about 282,600 square microns), more suitably in the range of about 200 microns to about 500 microns (corresponding to an average cross-sectional area in the range of about 31,400 square microns to about 196,250 square microns), and still more suitably in the range of about 200 microns to about 300 microns (corresponding to an average cross-sectional area in the range of about 31,400 square microns to about 70,650 square microns).

Although the multicellular body 1 illustrated in FIG. 1 is substantially cylindrical and has a substantially circular cross section, multicellular bodies having different sizes and shapes are within the scope of of the invention. For example, the multicellular body can be an elongate shape (e.g., a cylindrical shape) with a square, rectangular, triangular, or other non-circular cross sectional shape within the scope of the invention. Likewise, the multicellular body can have a generally spherical shape, a non-elongate cylindrical shape, or a cuboidal shape within the scope of the invention.

Method of Making the Multicellular Bodies

There are various ways to make multicellular bodies having the characteristics described above within the scope of the invention. For example, a multicellular body can be fabricated from a cell paste containing a plurality of living cells or with a desired cell density and viscosity. The cell paste can be shaped into a desired shape and a multicellular body formed through maturation (e.g., incubation). In another example, an elongate multicellular body is produced by shaping a cell paste including a plurality of living cells into an elongate shape. The cell paste is incubated in a controlled environment to allow the cells to cohere to one another to form the elongate multicellular body. It yet another example, a multicellular body is produced by shaping a cell paste including a plurality of living cells in a device that holds the cell paste in a three-dimensional shape. The cell paste is incubated in a controlled environment while it is held in the three dimensional shape for a sufficient time to produce a body that has sufficient cohesion to support itself on a flat surface, as described above.

The cell paste can suitably be provided by: (A) mixing the cells or cell aggregates (also referred to herein as "pre-selected" cells or cell aggregates) (may be one or more cell types) and a cell culture medium (also referred to herein as a "pre-selected" medium)(e.g., in a pre-determined ratio) to result in a cell suspension (also referred to herein as a cellular mixture), and (B) compacting the cellular mixture to produce the cell paste with a desired cell density and viscosity. The compacting may be achieved by a number of methods, such as by concentrating a particular cell suspension that resulted from cell culture to achieve the desired cell concentration (density), viscosity, and consistency required for the cell paste. For example, a relatively dilute cell suspension from cell culture may be centrifuged for a determined time to achieve a cell concentration in the pellet that allows shaping in a mold. Tangential flow filtration ("TFF") is another suitable method of concentrating or compacting the cells. Compounds may also be combined with the cell suspension to lend the extrusion properties required. Some examples of suitable compounds that may be used in the present invention include collagen, hydrogels, Matrigel, nanofibers, self-assembling nanofibers, gelatin, fibrinogen, etc.

Thus, the cell paste used in these methods is suitably produced by mixing a plurality of living cells with a tissue culture medium, and compacting the living cells (e.g., by centrifugation). If one or more ECM components, or one or more derivatives of one or more ECM components are to be included in the cell paste (as discussed in further detail below), the cell pellet can suitably be resuspended in one or more physiologically acceptable buffers containing the ECM component(s) or derivative(s) of ECM component(s) and the resulting cell suspension centrifuged again to form the cell paste.

The cell density of the cell paste desired for further processing may vary with cell types. The interactions between cells determine the properties of the cell paste, and different cell types will have a different relationship between cell density and cell-cell interaction. The cells may be pre-treated to increase cellular interactions before shaping the cell paste. For example, cells may be incubated inside a centrifuge tube after centrifugation in order to enhance cell-cell interactions prior to shaping the cell paste.

Various methods may be used to shape the cell paste under the present invention. For example the cell paste can be manipulated, manually molded or pressed (e.g., after concentration/compaction) to achieve the desired shape. For example, the cell paste may be taken up (e.g., aspirated) into a preformed instrument, such as a micropipette (e.g., a capillary pipette), that shapes the cell paste to conform to an interior surface of the instrument. The cross sectional shape of the micropipette (e.g., capillary pipette) can be circular, square, rectangular, triangular, or other non-circular cross sectional shape. The cell paste may also be shaped by depositing it into a preformed mold, such as a plastic mold, metal mold, or a gel mold. Furthermore, centrifugal casting or continuous casting may be used to shape the cell paste.

Figure 3A:
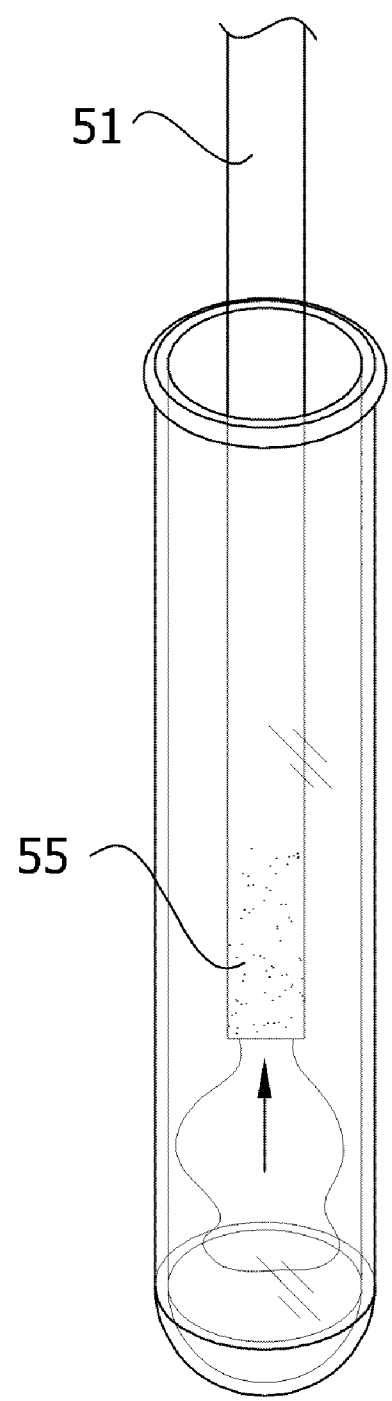
FIGS. 3A-3D illustrate one embodiment of a method of making the multicellular bodies illustrated in FIGS. 1A, 1B, 1C, and 2.
Figure 3B:
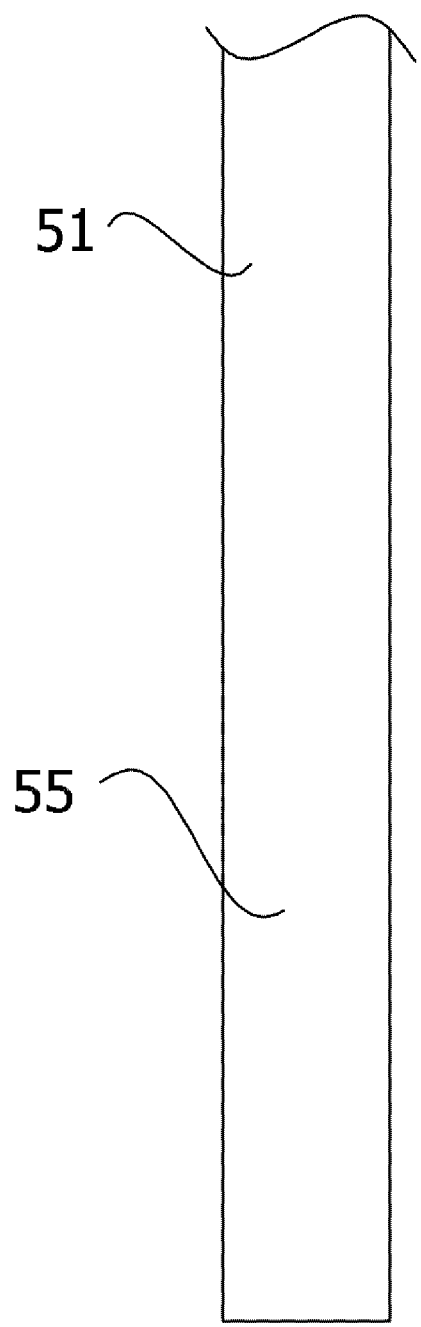

In one example of the method, the shaping includes retaining the cell paste in a shaping device to allow the cells to partially cohere to one another in the shaping device. For example, as illustrated in FIG. 3A, cell paste 55 can be aspirated into a shaping device 51 (e.g., a capillary pipette) and held in the shaping device for a maturation period (also referred to herein as an incubation period) (FIG. 3B) to allow the cells to at least partially cohere to one another. If the cells are able to achieve sufficient cohesion in the first shaping device 51, the multicellular body 1 can be produced in a process that has only a single maturation step (e.g, a single incubation step). For example, the method suitably includes shaping the cell paste 55 in a single shaping device 51 and incubating the shaped cell paste in a single controlled environment to allow the cells to cohere to one another to form the multicellular body 1. If this is the case, the shaping device 51 (e.g., capillary pipette) can suitably be part of a printing head of a bioprinter or similar apparatus operable to automatically place the multicellular body in a three-dimensional construct, as will be described in more detail below The inclusion of ECM components or derivatives of ECM components, for example gelatin and/or fibrinogen, in the cell paste may facilitate production of a multicellular body in a single maturation step because such components can promote the overall cohesivity of the multicellular body. However, there is a limit to the amount of time cells can remain in a shaping device such as a capillary pipette, which provides the cells only limited access at best to oxygen and/or nutrients, before viability of the cells is impacted.

If the cells cannot be retained in the shaping device 51 for a maturation period long enough to achieve the desired cohesion, the partially cohered cell paste 55 is suitably transferred from the shaping device (e.g., capillary pipette) to a second shaping device 301 (e.g., a mold) that allows nutrients and/or oxygen to be supplied to the cells while they are retained in the second shaping device for an additional maturation period. One example of a suitable shaping device 301 that allows the cells to be supplied with nutrients and oxygen is illustrated in FIGS. 4A-4D. This shaping device is a mold 301 for producing a plurality of multicellular bodies (e.g., substantially identical multicellular bodies). The mold 301 includes a biocompatible substrate 303 made of a material that is resistant to migration and ingrowth of cells into the substrate and resistant to adherence of cells to the substrate. The mold 301 may be made of any material that will exclude the cells from growing or migrating into or adhering to the mold. For example, the substrate 303 can suitably be made of Teflon® (PTFE), stainless steel, hyaluronic acid, agarose, agarose, polyethylene glycol, glass, metal, plastic, or gel materials (e.g., agarose gel or other hydrogel), and similar materials.

The substrate 303 is shaped to receive a composition comprising plurality of cells having a relatively lower cohesion (e.g., from the first shaping device 51) and hold the composition in a desired three-dimensional shape during a maturation period during which the cohesion of the cells increases to form a multicellular body that has a greater cohesion relative to the composition before the maturation period, such as a multicellular body having any of the characteristics of the multicellular body 1 described above. The mold 301 is also suitably configured so tissue culture media can be supplied to the cell paste 55 (e.g., by dispensing tissue culture media onto the top of the mold). For example, as illustrated in FIGS. 4A-4D a plurality of elongate grooves 305 are formed in the substrate 303. As illustrated in FIG. 4D, the depth D2 of each groove is suitably in the range of about 500 microns to about 1000 microns. The bottom of each groove 305 in the illustrated embodiment suitably has an arcuate (e.g., semicircular) cross-sectional shape for forming elongate cylindrical multicellular bodies that have a substantially circular cross-sectional shape. The width W5 of the grooves 305 is suitably slightly larger than the width of the multicellular body to be produced in the mold 301. For example, the width W5 of the grooves is suitably in the range of about 300 microns to about 1000 microns. The spacing between the grooves 305 is not critical, but it will generally be desirable to space the grooves relatively close to one another to increase the number of multicellular bodies that can be produced in the mold 301. In the illustrated embodiment for example, the strips of the substrate 303 between the grooves 305 each have a width W4 that is about 2 mm.

Figure 5A:
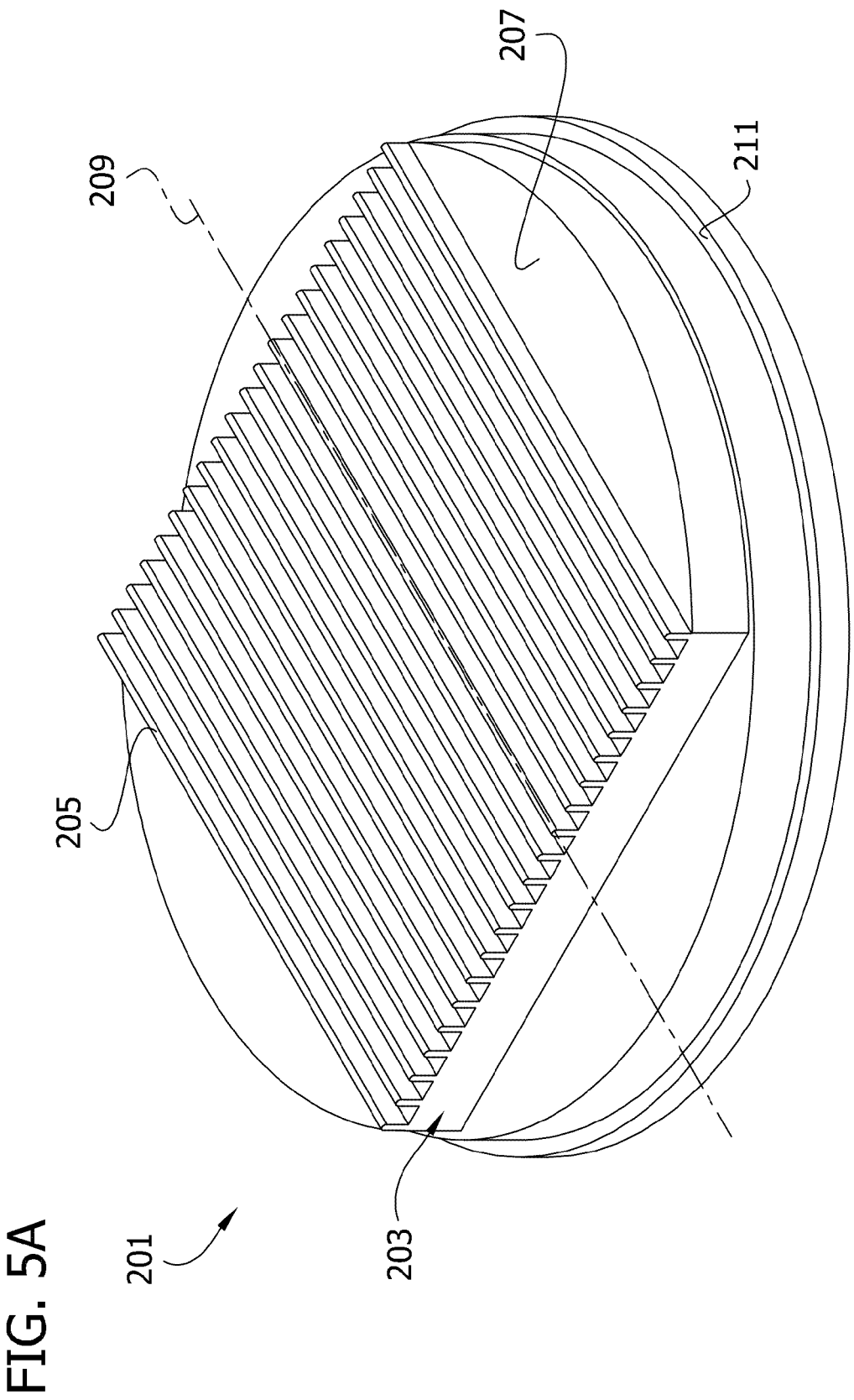
FIG. 5A is a perspective of one embodiment of a tool that can be used to make the mold illustrated in FIGS. 4A-4D.
Figure 5B:
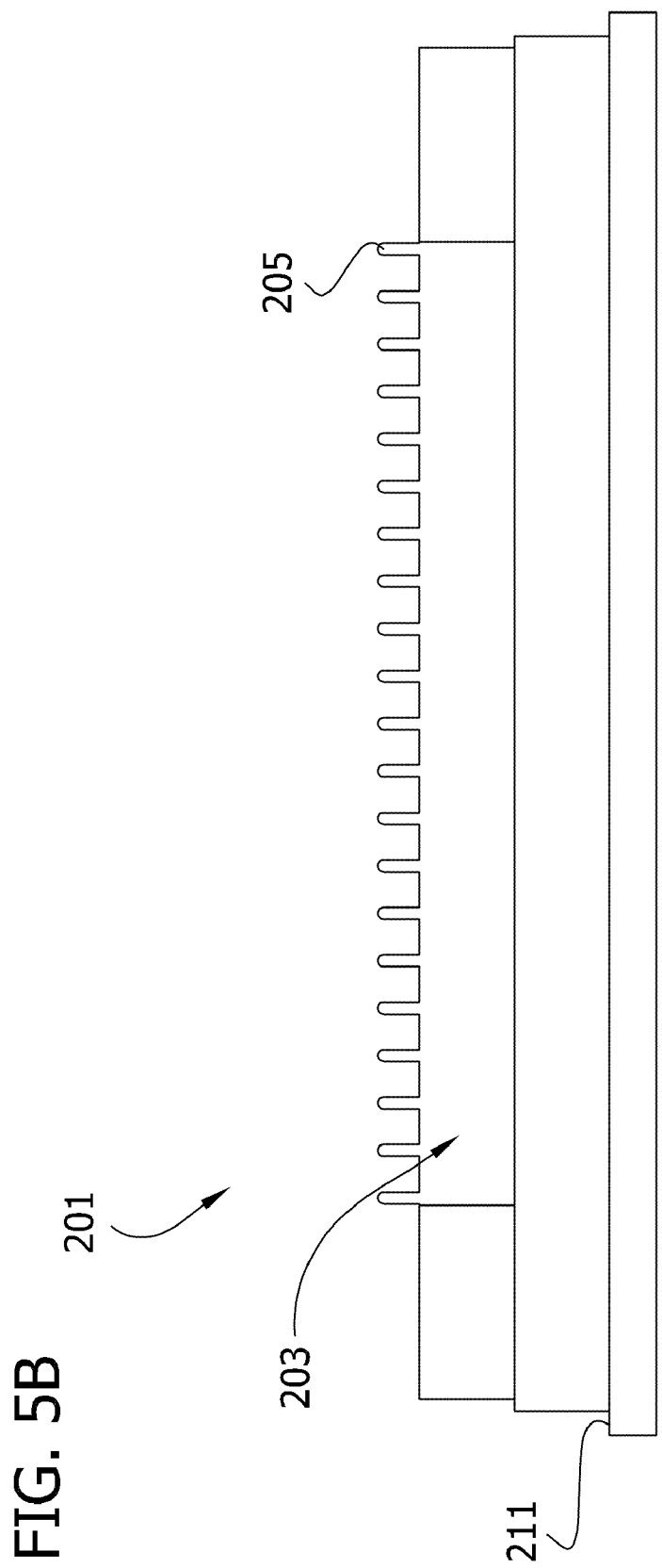
FIG. 5B is a side view of the tool illustrated in FIG. 5A.
Figure 5C:
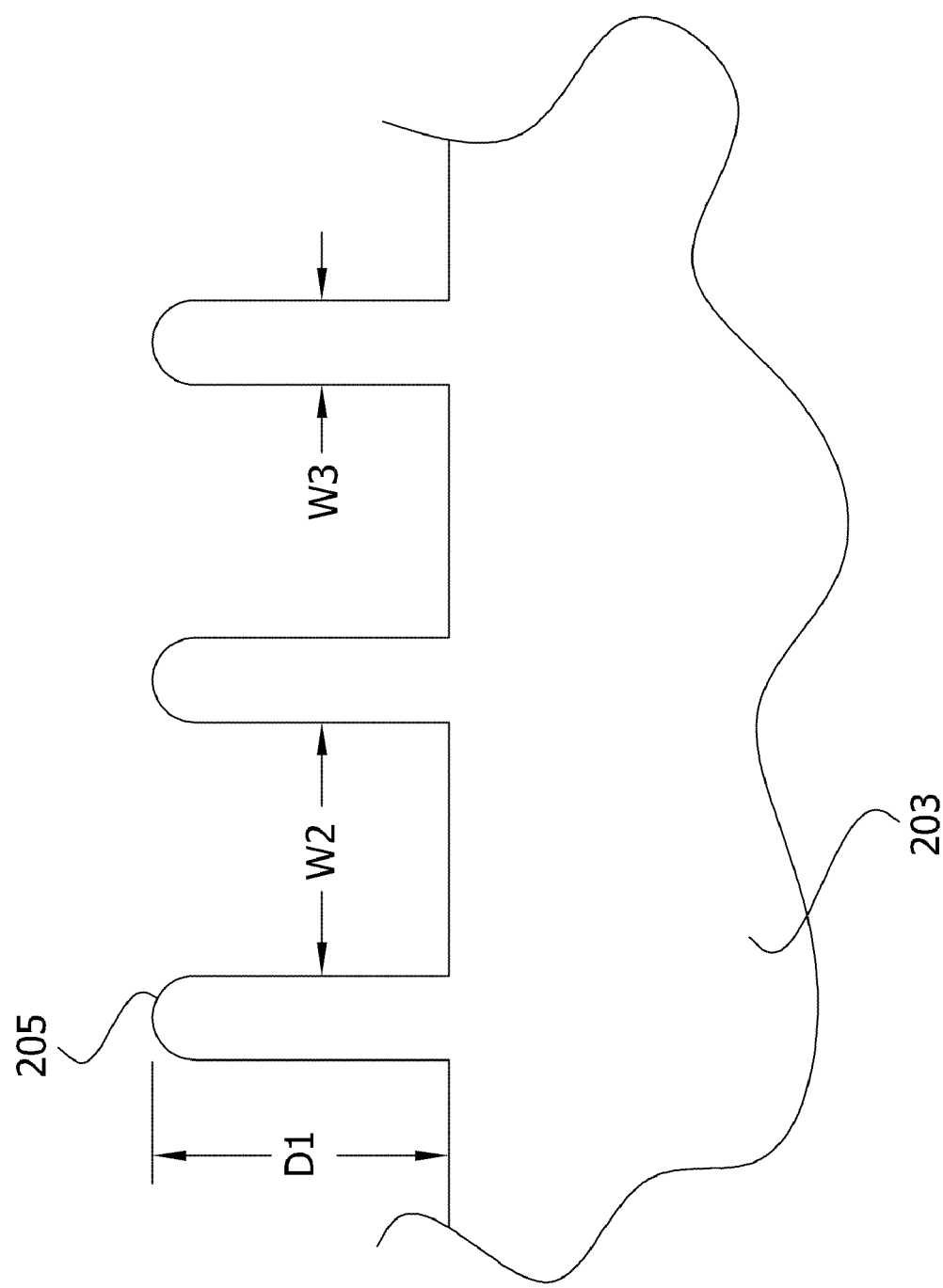
FIG. 5C is an enlarged side view of a portion of the tool as illustrated in FIG. 5B.

There are various ways to make a suitable mold within the scope of the invention. For example, FIGS. 5A-5C illustrate one embodiment of a tool, generally designated 201, that can be used to make a mold that is suitable for making the multicellular bodies described above. In general, a portion of the tool 201 is configured to be a negative of the portion of the mold 301 that retains the partially cohered cell paste during the second maturation period. For example, the tool 201 suitably includes a body 203 and a plurality of projections 205 extending from the body. Each projection 205 is suitably sized and shaped to form a depression or receiving area in the mold substrate that will retain cell paste 55 in a shape such that none of the cells in the depression/receiving area formed in the mold by the projection is more than about 300 microns from an exterior surface of the shaped cell paste.

Figure 4A:
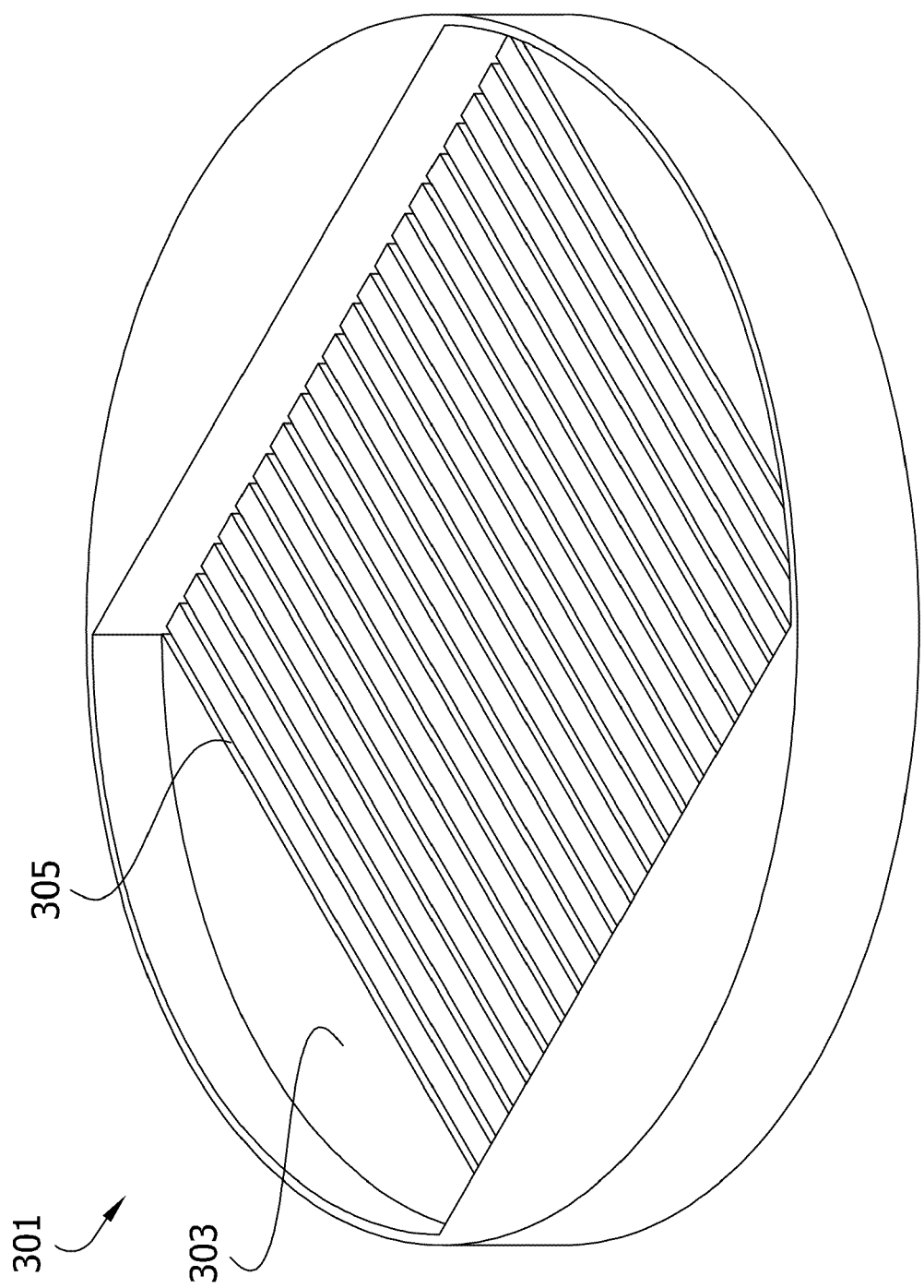
FIG. 4A is a perspective of one embodiment of a mold that is suitable for use in the method illustrated in FIGS. 3A-3D.
Figure 4B:
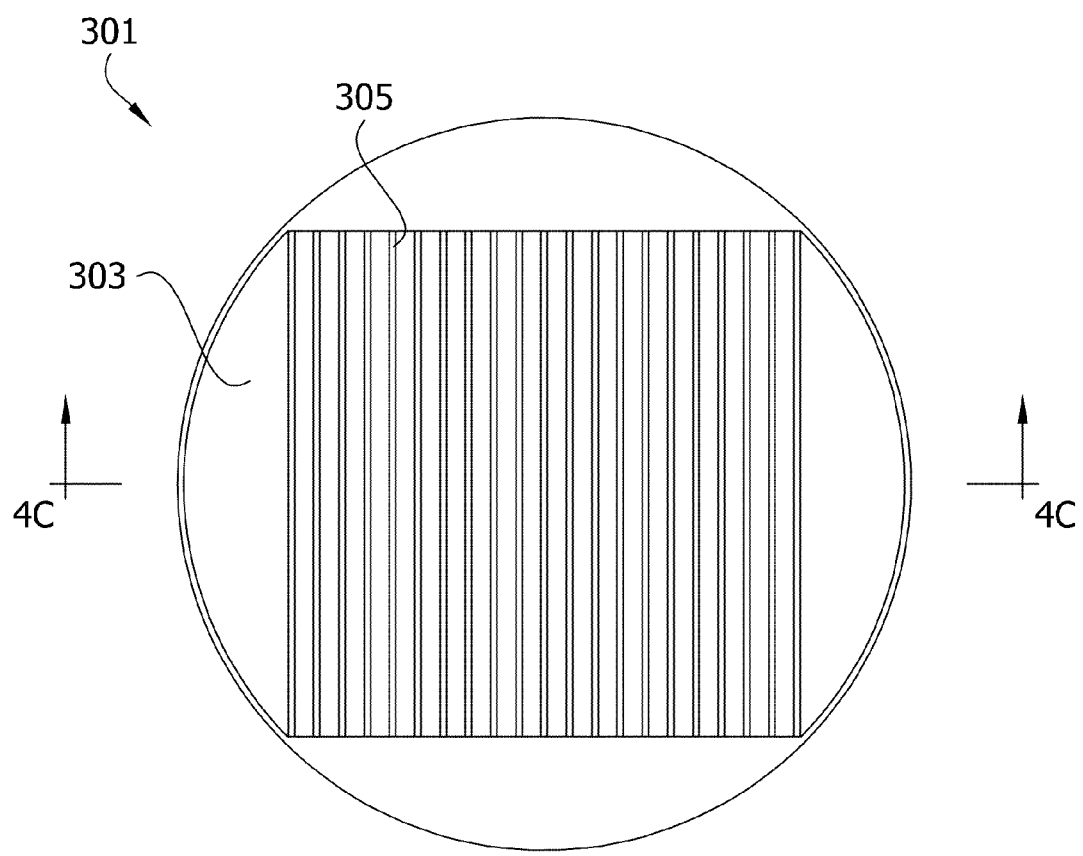
FIG. 4B is a top plan view of the mold.
Figure 4C:
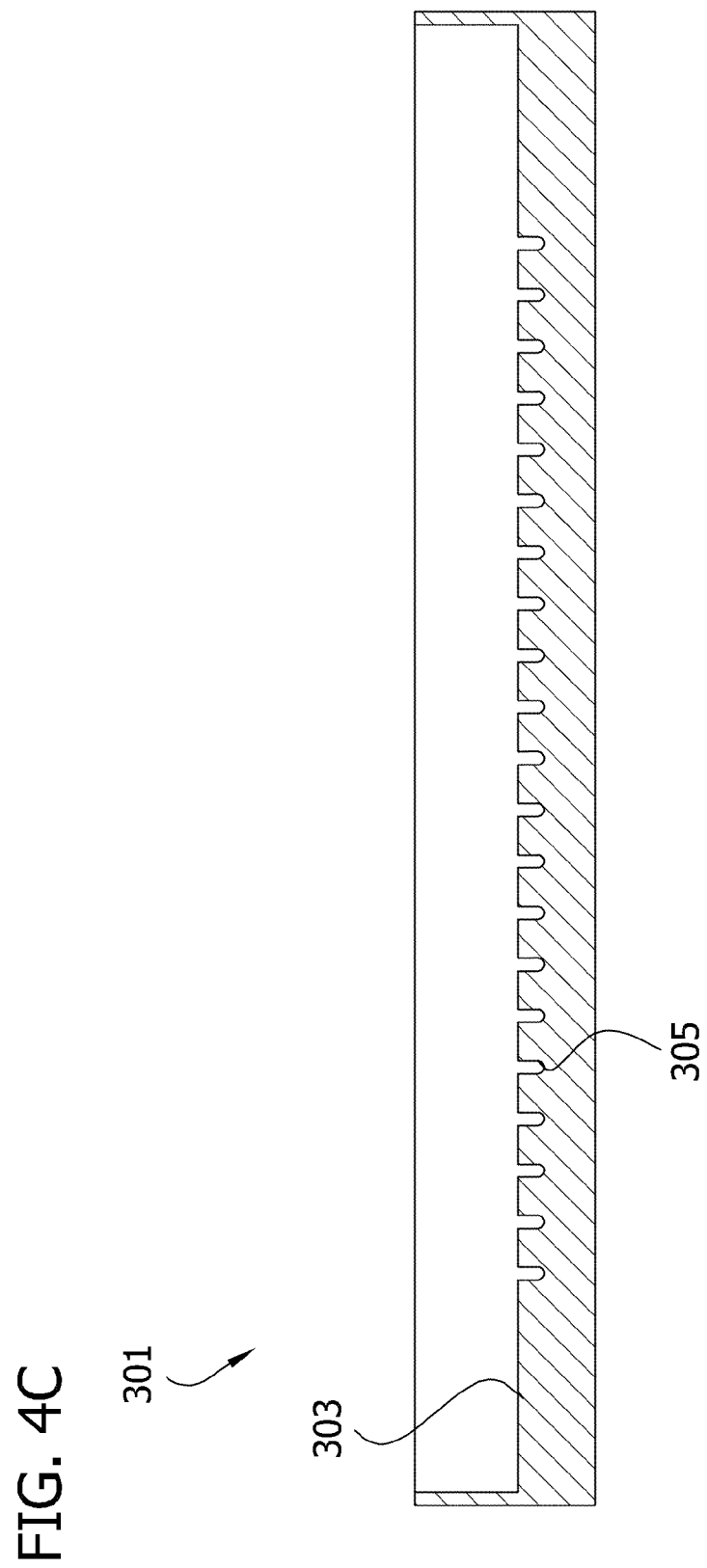
FIG. 4C is a cross section of the mold taken in a plane including line 4C-4C on FIG. 4B.
Figure 4D:
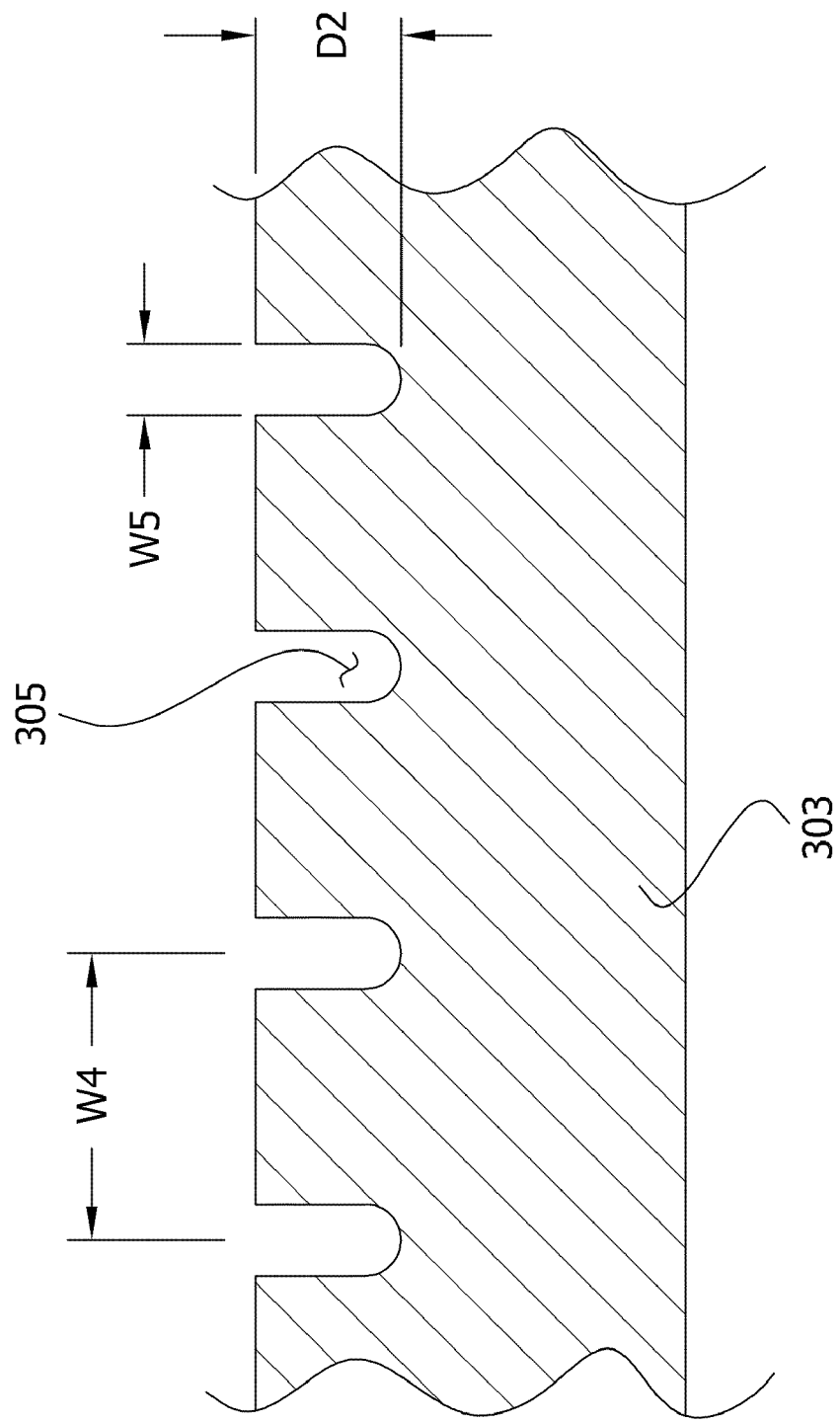
FIG. 4D is an enlarged cross-section of a portion of the mold as illustrated in FIG. 4C.

The particular tool 201 illustrated in FIGS. 5A-5C is configured to produce the mold 301 illustrated in FIGS. 4A-4B. The projections 205 are configured as a plurality of fins extending from a bottom 207 of the body 203. Each of the fins 205 is a negative of a one of the grooves 305 in the mold 301. The fins 205 have longitudinal axes 209 (FIG. 5A) and are configured to make a mold that can be used to make the elongate multicellular bodies 1 described above. At least one of the fins 205 is spaced laterally from the longitudinal axis 209 of another of the fins. This is one difference between the tool 201 and a conventional comb that is used to form wells in a gel for performing gel electrophoresis. In the illustrated embodiment, all of the fins 205 are substantially parallel to one another and each fin is spaced laterally from the other fins relative to their longitudinal axes 209. The fins 205 are suitably all substantially identical to one another. Referring to FIG. 5C, each fin 205 suitably extends from the body 203 a distance D1 of about 1.5 mm. The distal end of the fins 205 have an arcuate (e.g., semicircular) cross-sectional shape corresponding to the shape of the bottom of the grooves 305 in the mold 301. The width W3 of each fin is suitably about 300 microns to about 1000 microns. The distance W2 separating the fins is suitably about 2 mm. A lip 211 on the tool 201 is suitably configured to sit on the rim of a cell culture dish to hold the projections above the bottom of the dish. The tool 201 can be made of various materials from which the mold is easily separated, such as Teflon® (PTFE), stainless steel, and the like.

Figure 6A:
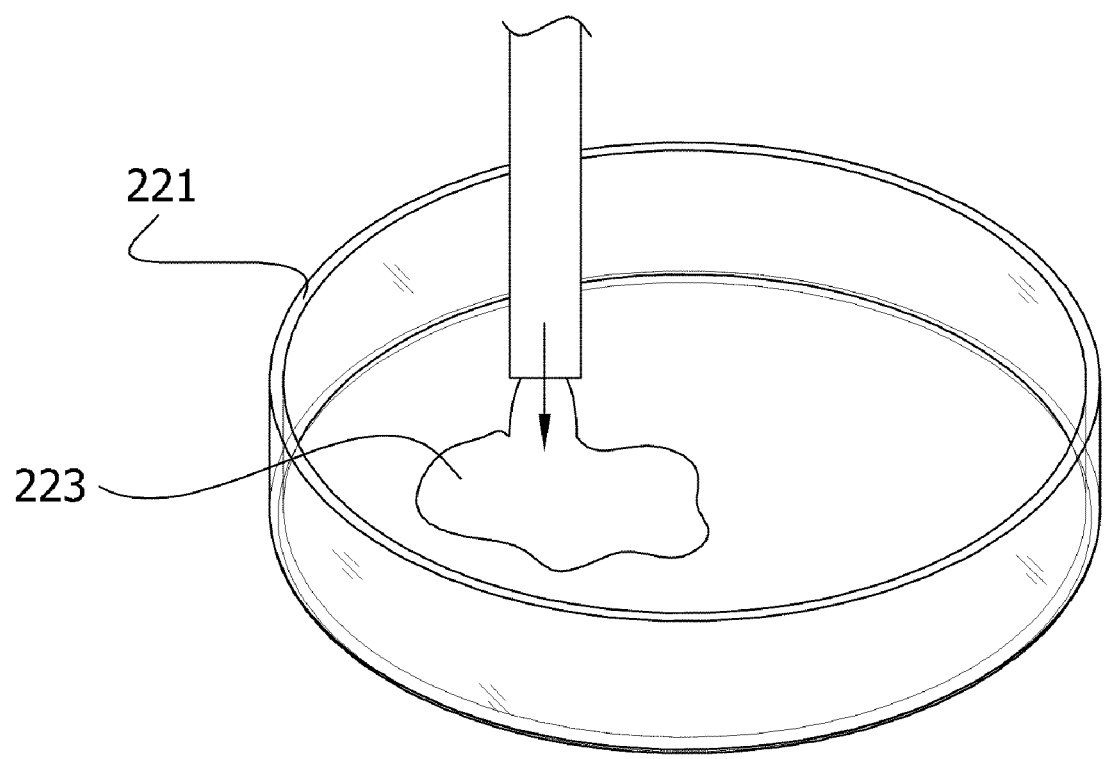
FIGS. 6A-6C illustrate one embodiment of a method of using the tool illustrated in FIGS. 5A-5C to make the mold illustrated in FIGS. 4A-4D.
Figure 6B:
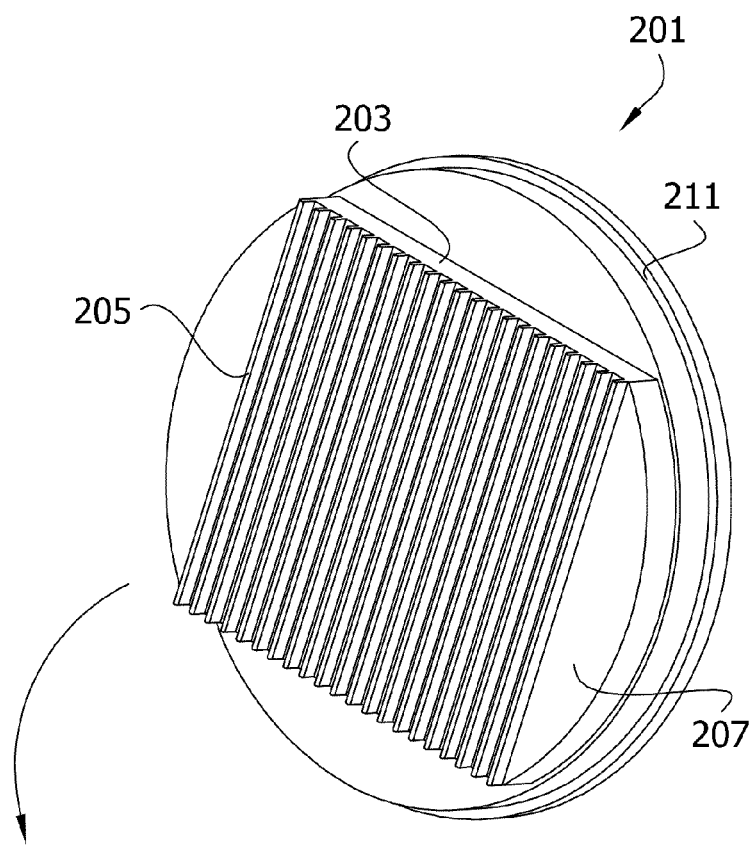
Figure 6B:
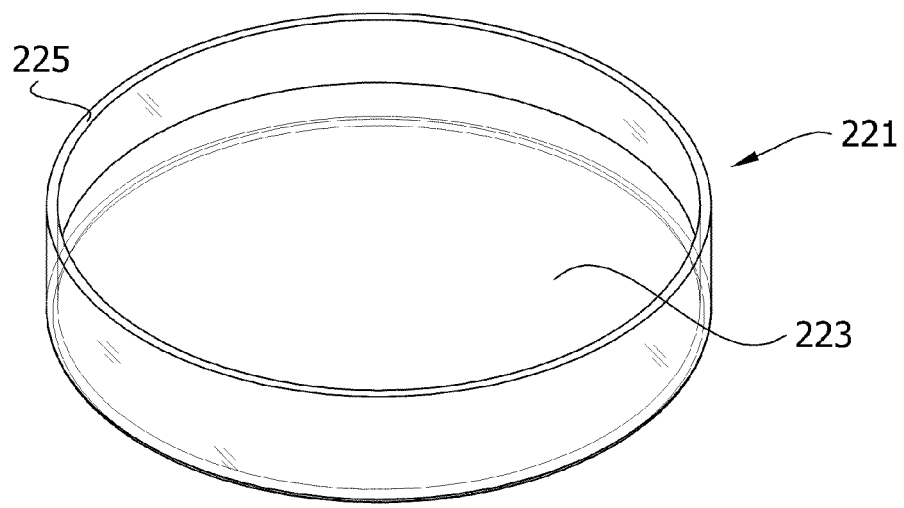
Figure 6C:
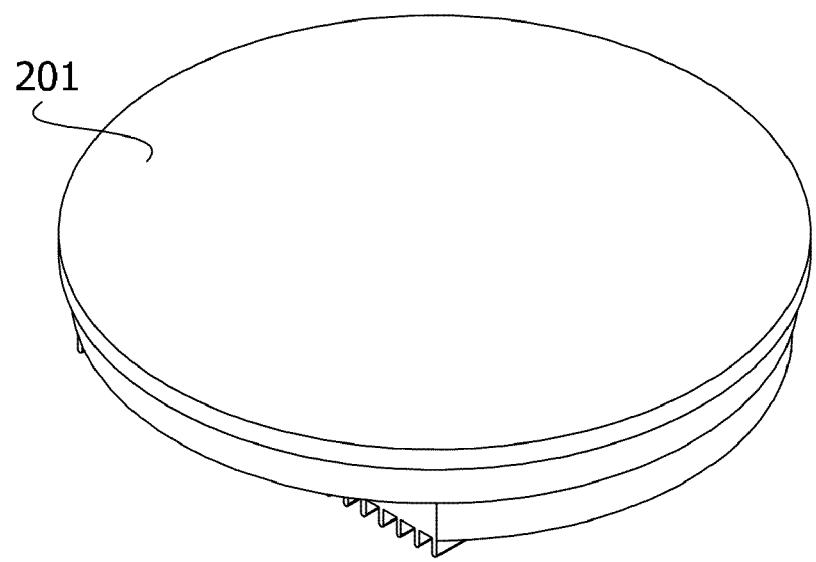
Figure 6C:
Figure 6C:
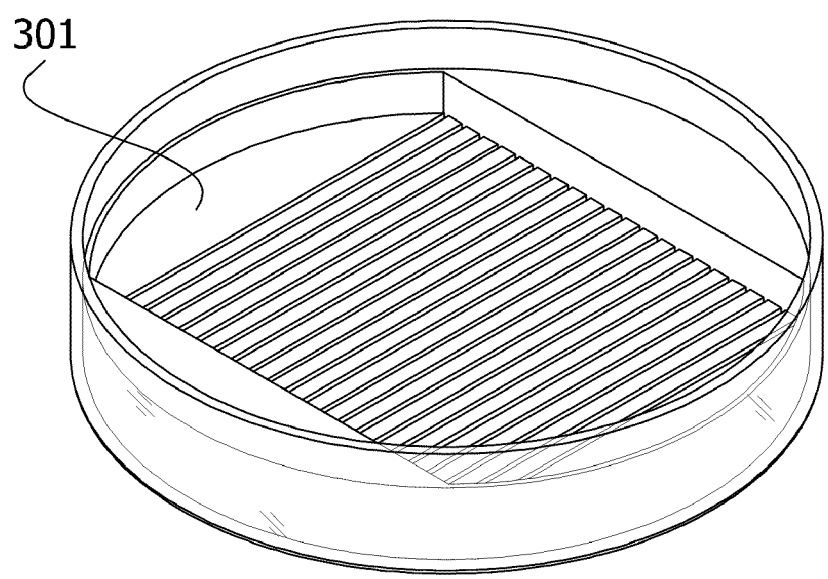

To make the mold 301 a cell culture dish 221 is suitably filled with a liquid 223 that can be made to solidify or set up as a gel, as illustrated in FIG. 6A. For example, the liquid can be an agarose solution 223. The tool 201 is placed on top of the cell culture dish 221 (FIG. 6B) so the lip 211 sits on the rim 225 of the cell culture dish and the projections 205 (e.g., fins) extend from the bottom 207 of the tool 201 into the liquid 223. The liquid 223 is allowed to set up to form a solid or gel substrate surrounding the distal ends of the projections 205 (e.g., fins). Then tool 201 is lifted off the cell culture dish to separate the tool 201 from the newly produced mold 301 (FIG. 6C).

Thus, if a second shaping device is used, the partially cohered cell paste 55 is suitably transferred from the first shaping device 51 (e.g., a capillary pipette) to the second shaping device (e.g., the mold 301 illustrated in FIGS.

Figure 3C:
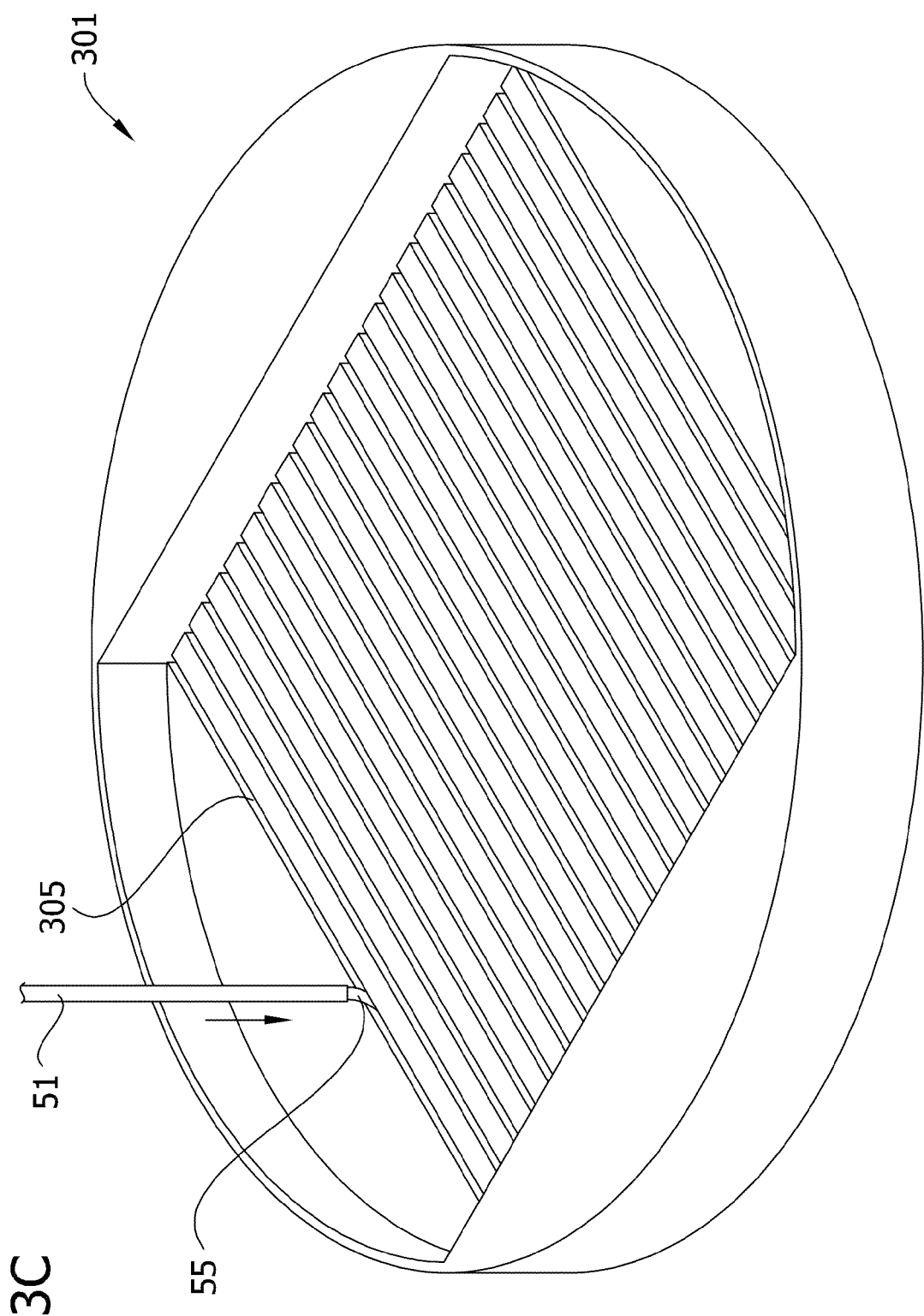
Figure 3D:
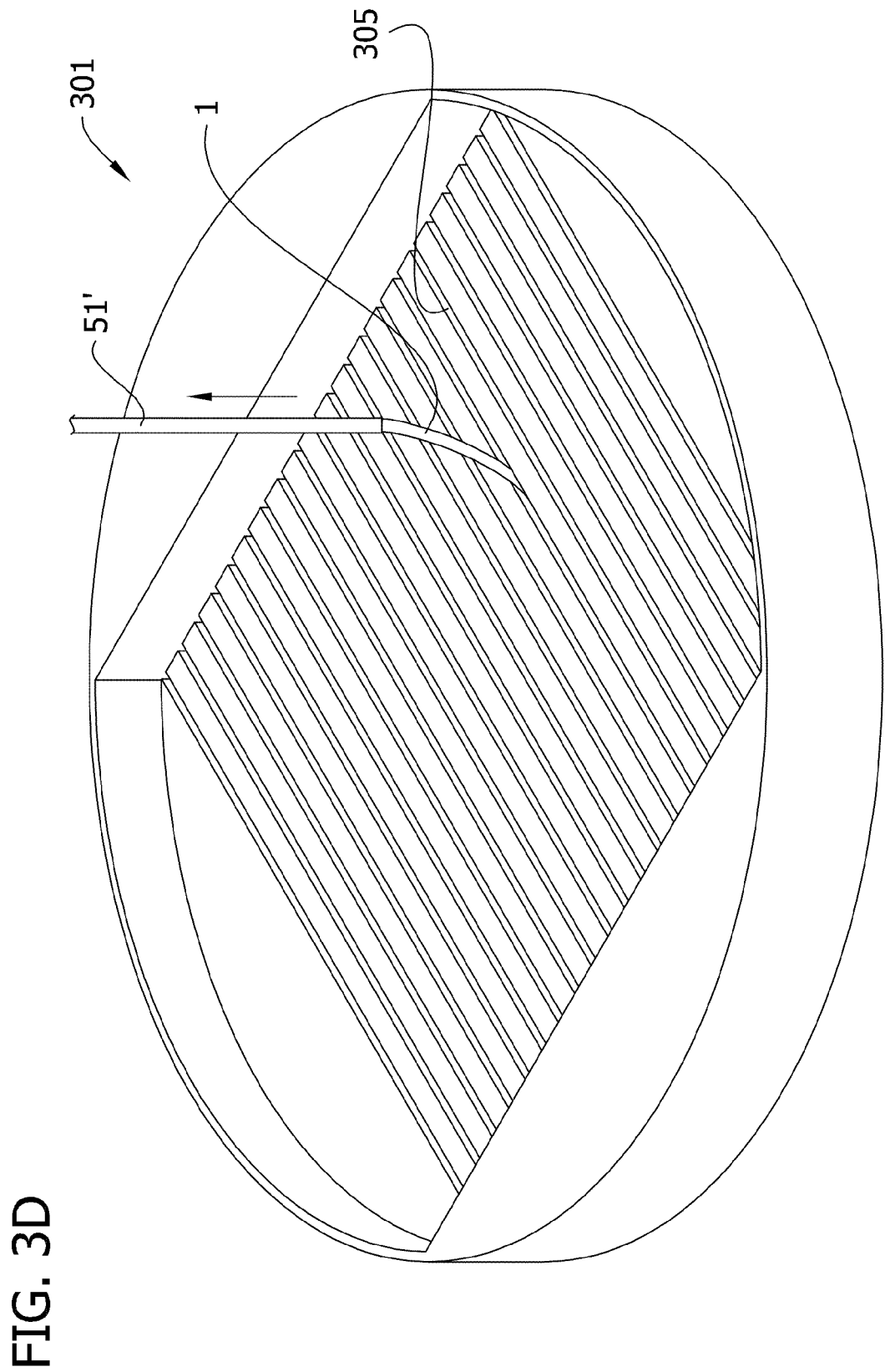

4A-4D). The partially cohered cell paste 55 can be transferred by the first shaping device 51 (e.g., the capillary pipette) into the grooves 305 of the mold 301, as illustrated in FIG. 3C. Thus, the method includes transferring the partially cohered cell paste 55 to a second shaping device 301, and retaining the partially cohered cell paste in the second shaping device to form the multicellular body 1. Following a maturation period in which the mold 301 is incubated along with the cell paste 55 retained therein in a controlled environment to allow the cells in the cell paste to further cohere to one another to form the multicellular body 1, the cohesion of the cells will be sufficiently strong to allow the resulting multicellular body 1 to be picked up with an implement 51', e.g., a capillary pipette as illustrated in FIG. 3D. The capillary pipette 51' (now containing the mature multicellular body 1 that has been picked up out of a groove 305 in the mold 301) can suitably be part of a printing head of a bioprinter or similar apparatus operable to automatically place the multicellular body into a three-dimensional construct, as will be described in more detail below.

Thus, in one example of the method of making a multicellular bodies 1, the shaping includes retaining the cell paste 55 in a first shaping device 51 to allow the cells to partially cohere to one another in the first shaping device, transferring the partially cohered cell paste to a second shaping device 301, and retaining the partially cohered cell paste in the second shaping device to form the multicellular body 1. However, in some embodiments, such as when gelatin and/or fibrinogen are added to the cell paste, the cells may sufficiently cohere to form the multicellular body in the first shaping device 51, and the step of transferring the cell paste 55 to a second shaping device 301 and retaining the cell paste in the second shaping device may be unnecessary.

The first shaping device 51 can suitably include a capillary pipette and the second shaping device can include a device that allows nutrients and oxygen to be supplied to the cells wile they are retained in the second shaping device, such as the above-described mold 301.

The cross-sectional shape and size of the multicellular bodies will substantially correspond to the cross-sectional shapes and sizes of the first shaping device and optionally the second shaping device used to make the multicellular bodies, and the skilled artisan will be able to select suitable shaping devices having suitable cross-sectional shapes, cross-sectional areas, diameters, and lengths suitable for creating multicellular bodies having the cross-sectional shapes, cross-sectional areas, diameters, and lengths discussed above.

As discussed above, a large variety of cell types may be used to create the multicellular bodies of the present invention. Thus, one or more types of cells or cell aggregates, both human and animal somatic cells, including, for example, all of the cell types listed above, may be employed as the starting materials to create the cell paste. For instance, cells such as smooth muscle cells, endothelial cells, chondrocytes, mesenchymal stem cells, myoblasts, fibroblasts, cardiomyocytes, Schwann cells, hepatocytes or Chinese hamster ovary ("CHO") cells may be employed. A sample of cells from an intended recipient (obtained, for example, by biopsy) or cells from one or more established cell lines can be cultured to produce a sufficient quantity of cells for fabrication of the multicellular bodies. Multicellular bodies made from cells from an intended recipient are advantageous for avoiding host inflammatory responses or other acute or chronic rejection of the transplanted organ or tissue by the recipient.

As noted above, the multicellular body can be homocellular or heterocellular. For making homocellular multicellular bodies, the cell paste suitably is homocellular, i.e., it includes a plurality of living cells of a single cell type. Almost all of the living cells in cell paste to be used for creating a homocellular multicellular body will be cells of the single cell type, subject to some tolerance for low levels of impurities, including a relatively small number of cells of a different cell type that have no more than a negligible impact on the maturation of a construct which includes homocellular multicellular bodies made from such cell paste. For example, cell paste for making homocellular multicellular bodies suitably includes cells of a first type, where at least about 90 percent of the cells in the cell paste are cells of the first cell type.

For making heterocellular multicellular bodies, on the other hand, the cell paste will suitably include significant numbers of cells of more than one cell type (i.e., the cell paste will be heterocellular). For example, the cell paste can comprise a plurality of living cells of a first type and a plurality of living cells of a second type, the second cell type being different from the first cell type. In another example, the cell paste can comprise a plurality of living cells of a first cell type, a plurality of living cells of a second cell type, and a plurality of living cells of a third cell type. Thus, if the cell paste is to be used to make heterocellular multicellular bodies which in turn are to be used to make vascular tissue the plurality of living cells in the cell paste can suitably include: (i) endothelial cells and smooth muscle cells; (ii) smooth muscle cells and fibroblasts; (iii) endothelial cells and fibroblasts; or (iv) endothelial cells, smooth muscle cells, and fibroblasts. As described in greater detail above, when heterocellular cell paste is used to create the multicellular bodies, the living cells may "sort out" during the maturation and cohesion process based on differences in the adhesive strengths of the cells, and may recover their physiological conformation.

In addition to the plurality of living cells, one or more ECM components or one or more derivatives of one or more ECM components (e.g., gelatin, fibrinogen, collagen, fibronectin, laminin, elastin, and/or proteoglycans) can suitably be included in the cell paste to incorporate these substances into the multicellular bodies, as noted above. The ECM components or derivatives of ECM components added to the cell paste can be purified from a human or animal source, or produced by recombinant methods known in the art. Adding ECM components or derivatives of ECM components to the cell paste may promote cohesion of the cells in the multicellular body. For example, gelatin and/or fibrinogen can be added to the cell paste. More particularly, a solution of 10-30% gelatin and a solution of 10-80 mg/ml fibrinogen can be mixed with a plurality of living cells to form a cell suspension containing gelatin and fibrinogen. The cell suspension can then be compacted (e.g., by centrifugation) to form the cell paste. The cell paste formed by this process can then be shaped and incubated in a controlled environment to allow the cells to cohere to one another to form the multicellular body. The fibrinogen can be converted to fibrin by the addition of thrombin (e.g., during the printing process). When ECM components or derivatives of ECM components such as, for example, gelatin and fibrinogen, are included in the cell paste, the shaping step suitably comprises retaining the cell paste in a single shaping device to form the multicellular body, and the incubating step suitably comprises incubating the shaped cell paste in a single controlled environment to allow the cells to cohere to one another to form the multicellular body.

The present invention also provides a method for fabrication of a multicellular body comprising a plurality of cells or cell aggregates formed in a desired 3-D shape. The inventive fabrication method generally comprises the steps of 1) providing a cell paste containing a plurality of pre-selected cells or cell aggregates (e.g., with a desired cell density and viscosity), 2) shaping the cell paste (e.g., into a desired shape), and 3) forming the multicellular body through maturation.

The aforesaid forming step may be achieved through one or multiple steps to ensure the coherence of the multicellular body (e.g., cellular unit). In certain processes, upon the initial maturation, the cell paste may be partially stabilized, or partially hardened to form the multicellular body with integrity sufficient to allow further handling.

According to one embodiment, the forming step may include two substeps: A) retaining the cell paste in the shaping device, such as a micropipette (e.g., a capillary pipette), for a first time period (e.g., a pre-determined time period) for the initial maturation, and B) depositing the shaped cell paste into a holding device, such as a mold, for a second time period (e.g., a pre-determined time period) for further maturation, where the holding device is made of a material capable of excluding cells from growing or migrating into, or adherence onto it. The initial maturation will provide the cell paste with sufficient stability to remain intact during the handling in the further maturation process.

Various methods can be used to facilitate the further maturation process. In one embodiment, the cell paste may be incubated at about 37° C. for a time period (which may be cell-type dependent) to foster coherence. Alternatively or in addition, the cell paste may be held in the presence of cell culture medium containing factors and/or ions to foster adherence.

For example, after a cell paste in a cylindrical shape is incubated in a micropipette (e.g., a capillary pipette) (i.e., the initial maturation process) until the adherence of the cells is such that the cylinder can be extruded without breakage from the micropipette, the cell paste may then be further incubated and cultured with medium in the further maturation process, which encourages retention of the desired shape.

Filler Bodies

The present invention also provides filler bodies which can be used in combination with the above-described multicellular bodies to form desired three-dimensional biological engineered tissues. Specifically, the present invention also provides a filler body (also referred to herein as a "filler matrix unit") to be used in combination with the multicellular bodies as building units for constructing a biological construct, where the filler bodies are used to define the domains of the desired 3-D bio-construct that are devoid of multicellular bodies. The filler body is suitably a body having a pre-determined shape made of a material capable of excluding cells growing or migrating into or adhering to it. The filler body material is suitably permeable to nutrient media (also referred to herein as tissue culture medium or cell culture medium). For example, the filler body material is suitably a biocompatible gel material selected from the group consisting of agarose, hyaluronic acid, polyethylene glycol, and agar, or other hydrogel or a non-gel flexible biocompatible material. The filler bodies can suitabley be formed from different materials or from different concentrations of the same material. For example, a lumen-forming filler body can be made of 4% agarose, while the remaining filler bodies used to construct a desired three-dimensional biological engineered tissue can be made of 2% agarose. The filler body may assume any shape or size in accordance with the shape or size of the corresponding multicellular body, with a cylindrical shape as preferred.

In some embodiments, the filler bodies have shapes and sizes substantially identical to the shapes and sizes of the multicellular bodies with which they are to be used to build a desired three-dimensional biological engineered tissue. Thus, for example, the filler bodies can suitably have any of the shapes described above in connection with the multicellular body 1. For example, both the filler bodies and the multicellular bodies may be substantially cylindrical and have substantially circular cross-sections having substantially identical diameters (as shown in FIG. 2).

The filler bodies and the multicellular bodies can have different sizes and or/shapes, so long as the filler bodies and multicellular bodies can be arranged according to a pattern such that a desired three-dimensional biological engineered tissue is formed when the multicellular bodies fuse to one another. For instance, the filler bodies can be substantially cylindrical and the multicellular bodies can be substantially spherical (as illustrated in FIG. 2). Further, the filler bodies and the multicellular bodies may both be elongate and substantially cylindrical, but have different lengths. The skilled artisan will recognize that there are many ways in which filler bodies and multicellular bodies of varying sizes and shapes can be combined to form a desired three-dimensional biological engineered tissue.

A filler body is suitably produced by shaping a suitable gel-like material into a pre-determined shape. According to one embodiment, the method may further include the steps of: 1) decreasing (lowering) the viscosity of a filler material (i.e., the pre-selected filler material) to a liquid-like material, 2) shaping the liquid-like material (e.g., into a pre-selected shape), and 3) increasing (raising) the viscosity of the material to solidify into a filler body (e.g., with the pre-selected shape).

A number of known methods may be used to decrease the viscosity of a filler material, including direct or indirect heating of the material, application of pressure, or changing its concentration. Moreover, a number of methods may be employed in the shaping step, such as depositing the material into a precast mold, or drawing it into a chamber of desired shape by a pipette or negative displacement of a piston. Furthermore, a number of known methods may be employed to increase the viscosity of the material to solidify its shape, including direct or indirect cooling of the material, causing or allowing a solvent to be removed or evaporated, allowing chemical action to harden the material, changing the concentration of the components or allowing crosslinking of a polymeric material by chemical or other action.

For example, according to one embodiment, agarose solution (agarose originally in powder phase mixed with buffer and water) may be heated to reduce its viscosity and taken up (e.g., aspirated) into a capillary pipette (i.e., micropipette) with a desired dimension (or into a chamber of a desired shape by negative displacement of a piston). Depending on the desired cross-sectional shape of the filler body, capillary pipettes having various cross-sectional shapes can be used. For example, a capillary pipette having a substantially circular cross-sectional shape along its length can be used to make filler bodies which are substantially cylindrical and which have substantially circular cross sectional shapes. Alternatively, a capillary pipette having a substantially square cross-section along its length can be used to make filler bodies which are substantially cylindrical and which have square cross-sectional shapes. The skilled artisan will recognize that filler bodies having a myriad of cross-sectional shapes can be produced in a similar manner using capillary pipettes as used in making multicellular bodies as described above.

The agarose solution in the pipette (or the chamber) may be cooled to room temperature, for example by forced air on the exterior of the pipette or plunging the pipette into a container with cold liquid, so that it can solidify into an agarose gel with the desired shape, i.e., filler body. The resulting filler body may be extruded from the pipette or chamber during the construction of a particular bio-construct.

A filler body can suitably be produced by a bioprinter or similar apparatus as it assembles a three-dimensional construct comprising an arrangement of multicellular bodies and filler bodies. For example, a capillary pipette can be part of a printing head of a bioprinter. When a filler body is needed for the three-dimensional construct, the capillary pipette can be transported to a source of liquid that can set up as a gel. For example, the capillary pipette can be transported to supply of agarose solution that is heated to maintain it in a liquid state. The liquid can be aspirated into the capillary pipette to shape the liquid into the shape of the filler body. Then the capillary pipette can be chilled (e.g., by immersing it in a cold water bath) in order to expedite the setting up of the agarose gel.

Three-Dimensional Constructs

The multicellular bodies and filler bodies described above can be used in accordance with the methods of the present invention to produce a three-dimensional biological engineered tissue. Briefly, a plurality of multicellular bodies and a plurality of filler bodies are arranged according to a pattern such that each multicellular body contacts at least one of (i) another multicellular body, or (ii) a filler body. The multicellular bodies are then allowed to fuse with at least one other multicellular body to form a three-dimensional biological engineered tissue. The filler bodies can then be separated from the fused multicellular bodies to obtain the engineered tissue.

Figure 1C:
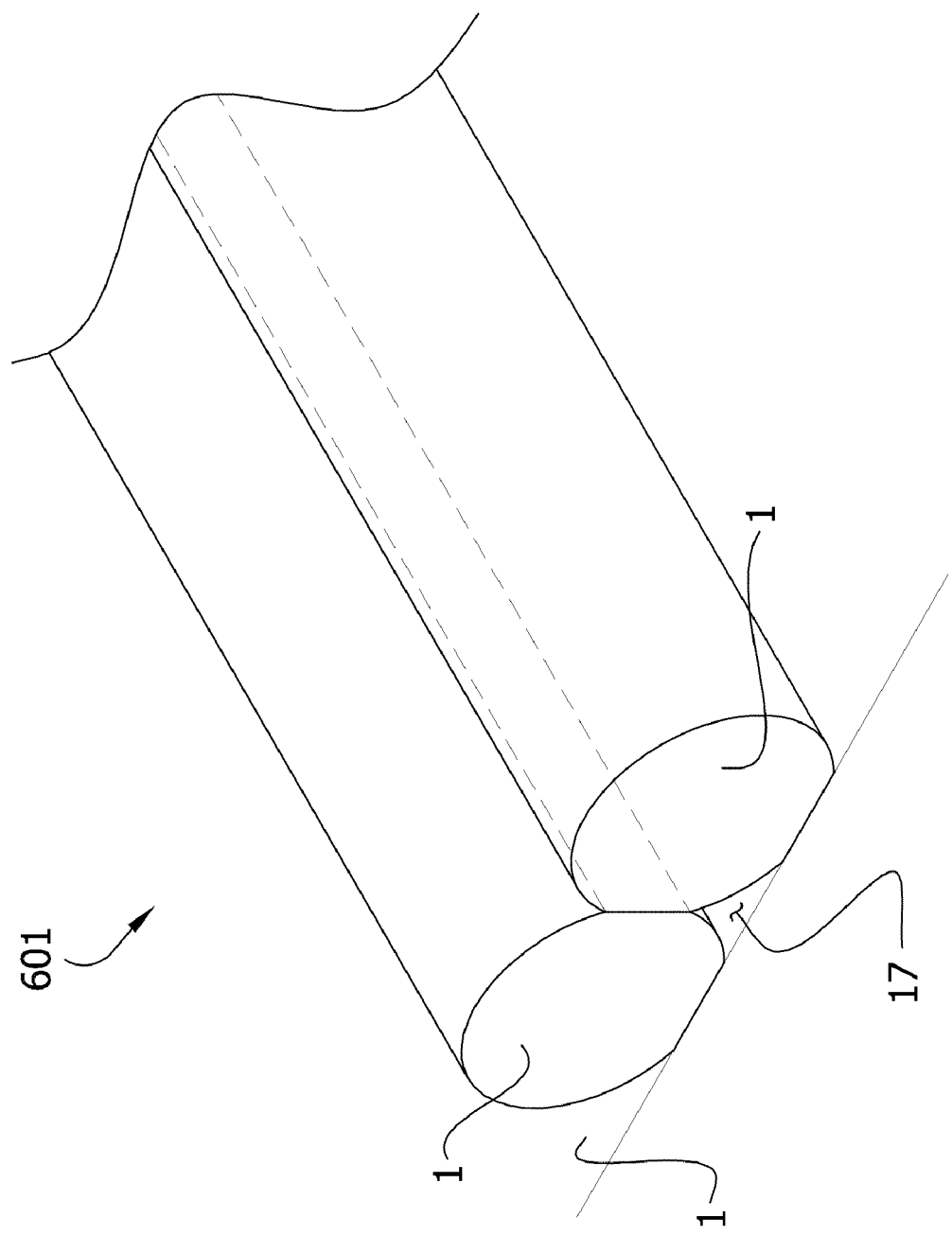
FIG. 1C is a an enlarged perspective of the ends of multiple multicellular bodies in side-by-side adjoining relation to one another on the surface.
Figure 2:
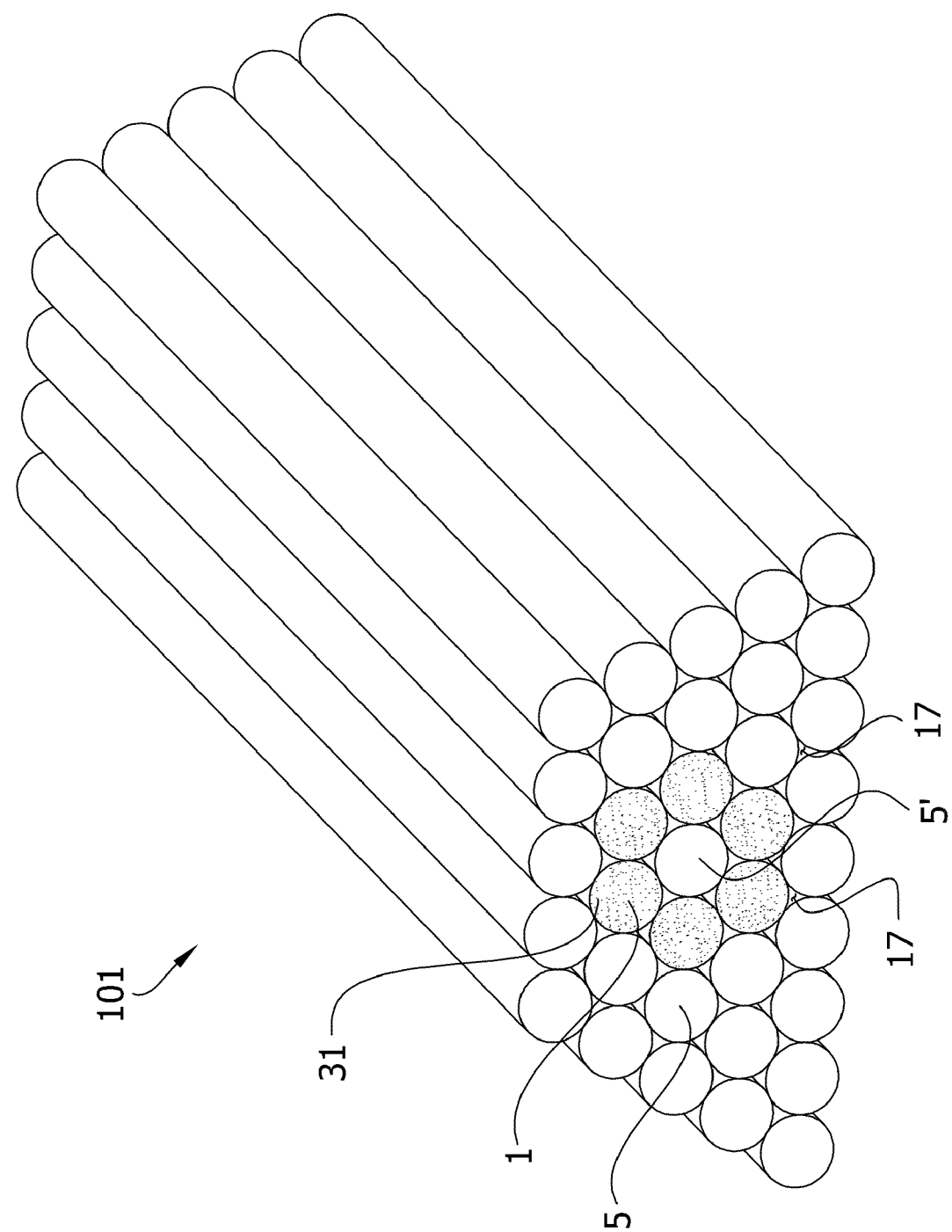
FIG. 2 is a perspective of one embodiment of a three-dimensional construct including a plurality of the multicellular bodies and a plurality of filler bodies arranged in a pattern suitable for producing one embodiment of an engineered tissue.

One embodiment of a three-dimensional structure of the present invention, which is generally designated 101, is illustrated in FIG. 2. The structure 101 includes a plurality of elongate multicellular bodies 1, each of which is suitably identical to the elongate multicellular body 1 described above. For example, each of the elongate multicellular bodies 1 has suitably been produced according to the methods described above for producing a self-supporting multicellular tissue body that can be printed in air. The multicellular bodies 1 are arranged in a pattern in which each multicellular body contacts at least one other multicellular body. As best understood in reference to FIG. 1C, at least one of the multicellular bodies 1 contacts another of the multicellular bodies along a contact area that has a substantial length. Although FIG. 1C shows two multicellular bodies 1 in side-by-side adjoining relation on a surface 13 rather than arranged in the pattern illustrated in FIG. 2, it is understood that the contact area between two of the multicellular bodies 1, can be substantially similar to the contact area illustrated in FIG. 1C whenever they are arranged in a pattern in which they are in side-by-side adjoining relation to one another. For example, in the arrangement of FIG. 2 each of the multicellular bodies 1 contacts at least one (e.g., two) other multicellular bodies over a contact area having a substantial length. The contact area between adjoining elongate multicellular bodies in side-by-side relation suitably has a length of at least about 1000 microns, more suitably at least about 1 centimeter, more suitably at least about 5 centimeters, and still more suitably in the range of about 5 centimeters to about 30 centimeters. In another example, the contact area has a length that is suitably in the range of about 1000 microns to about 30 centimeters, and more suitably in the range of about 1 centimeter to about 30 centimeters. The length of the contact area can correspond to the length of the multicellular bodies 1. Because there is no theoretical upper limit on the length of the multicellular bodies 1, the contact area can have a length in excess of 30 centimeters (or any arbitrary length different from 30 centimeters) within the scope of the invention provided a person is willing to overcome practical difficulties, such as the need to obtain a sufficient quantity of cell paste, associated with production of long multicellular bodies. Although the multicellular bodies 1 are in contact with one another in FIG. 2, at this initial stage of maturation the multicellular bodies are not cohered to one another.

The structure also includes one or more filler bodies 5, each of which is suitably identical to the filler body described above. For example, the structure in FIG. 2 includes a plurality of discrete filler bodies 5. The filler bodies 5 are arranged in the pattern with the multicellular bodies so each filler body contacts at least one multicellular body or another filler body. The multicellular bodies 1 and filler bodies 5 in FIG. 2 are arranged to form a plurality of spaces 17 in the structure 101 that are not occupied by the multicellular bodies and also not occupied by the filler bodies. The spaces 17 suitably contain tissue culture medium, which can be added to the structure 101 by pouring the tissue culture medium over the top of the multicellular bodies 1 and filler bodies 5. Thus, the spaces 17 can facilitate supply of nutrients and/or oxygen to the cells in the multicellular bodies 1 (e.g., during maturation).

The multicellular bodies 1 in the structure illustrated in FIG. 2 can be homocellular bodies, heterocellular bodies, or a combination thereof In particular, the multicellular bodies 1 can suitably include any of the cell types and combinations of cell types described above. As illustrated, the multicellular bodies are suitably substantially identical with respect to the cell types contained therein. However, it is possible that one or more of the multicellular bodies contains cells of a different cell type than the other multicellular bodies in the structure within the scope of the invention. For example, a majority of the cells in each of one or more of the multicellular bodies 1 can suitably be cells of a first cell type (e.g., endothelial cells or smooth muscle cells) and a majority of the cells in each of one or more other multicellular bodies in the structure 101 can be cells of a second cell type (e.g., smooth muscle cells or fibroblasts) that is different from the first cell type. The multicellular bodies 1 are suitably substantially uniform in shape. The filler bodies are also suitably substantially uniform in shape. Further, as illustrated in FIG. 2, the multicellular bodies 1 have a shape that is substantially identical to the shape of the filler bodies 5.

At least some of the multicellular bodies 1 (e.g., all of the multicellular bodies) are arranged to form a tube-like structure 31. At least one of the filler bodies 5' is inside the tube-like structure 31 and substantially surrounded by the multicellular bodies 1 that form the tube-like structure. For example, the multicellular bodies 1 in FIG. 2 are arranged in a hexagaonal configuration to form a tube-like structure 31 surrounding one of the filler bodies 5. Each of the multicellular bodies 1 in the hexagonal configuration of FIG. 2 is in side-by-side adjoining relation with at least two neighboring elongate multicellular bodies. In this arrangement, the one or more filler bodies 5' inside the tube-like structure 31 are lumen-forming filler bodies. The one or more lumen-forming filler bodies 5' are referred to as such because they prevent migration and ingrowth of cells from the multicellular bodies 1 into an elongate space that extends through the tube-like structure 31, which becomes a lumen after maturation of the structure according to the methods described below. The one or more lumen-forming filler bodies 5' do not develop any lumen within themselves during maturation. In general, any arrangement of multicellular bodies that can via maturation produce a tubular engineered tissue that includes a plurality of living cells can be considered a tube-like structure whether or not there are filler bodies inside the tube-like structure. It is apparent from the foregoing that the tube-like structure can differ from a tubular structure by virtue of the fact the adjoining multicellular bodies are not cohered to one another at this stage of maturation so an object could be pushed into the space between two of the adjoining multicellular bodies forming the tube-like structure.

Another embodiment of a three-dimensional structure, generally designated 201, is illustrated in FIG. 7. Except as noted, this structure can be substantially identical to the structure illustrated in FIG. 2 and described above. The structure 201 in FIG. 7 includes a plurality of multicellular bodies, each of which can be identical to the multicellular body 1 described above. However, in this structure 201 there are two different sets of multicellular bodies 1', 1" arranged in the pattern that forms the structure. A majority of the cells in the multicellular bodies 1' of the first set (e.g., at least about 90 percent of the cells) are cells of a first cell type and a majority of the cells in the multicellular bodies 1" of the second set (e.g., at least about 90 percent of the cells) are cells of a second cell type that is different from the first cell type. For example, the majority of the cells in the first set of multicellular bodies 1' can suitably be endothelial cells and the majority of the cells in the second set of multicellular bodies 1" can suitably be smooth muscle cells. As another example, the majority of the cells in the first set of multicellular bodies 1' can suitably be endothelial cells and the majority of the cells in the multicellular bodies 1" in the second set can be fibroblasts. As yet another example, the majority of cells in the first set of multicellular bodies 1' can suitably be smooth muscle cells and the majority of the cells in the multicellular bodies 1" in the second set can be fibroblasts. It is also possible to use other cell types. The first set of multicellular bodies 1' is arranged in a hexagonal configuration (similar to the hexagonal configuration described above) surrounding one or more lumen-forming filler bodies 5'. The second set of multicellular bodies 1" is arranged in a larger hexagonal configuration surrounding the first set of multicellular bodies 1' and the one or more lumen-forming filler bodies 5'. Together, the multicellular bodies 1', 1" form a tube-like structure 231 that includes two different types of cells. The first set of multicellular bodies 1' are arranged to form an inner layer of the tube-like structure 231 and the second set of multicellular bodies 1" are arranged for form an outer layer of the tube-like structure. Accordingly, cells of the first cell type (e.g., endothelial cells) are more concentrated in an inner portion of the tube-like structure 231 and cells of the second cell type (e.g., smooth muscle cells) are more concentrated in an outer portion of the tube-like structure, such that a ratio of the number of endothelial cells to the number of non-endothelial cells in the first set of multicellular bodies 1' is greater than a ratio of the number of endothelial cells to the number of non-endothelial cells in the second set of multicellular bodies 1", or a ratio of the number of smooth muscle cells to the number cells that are not smooth muscle cells in the second set of multicellular bodies 1" is greater than a ratio of the number of smooth muscle to the number of cells that are not smooth muscle cells in the first set of multicellular bodies 1'. This arrangement can facilitate production of a tubular engineered tissue having an inner layer of cells of the first type and an outer layer of cells of the second type. For instance the structure 201 can be used to produce an engineered blood vessel having an inner layer of endothelial cells and an outer layer of smooth muscle cells. In another example, a first set of multicellular bodies 1' each comprising a plurality of endothelial cells and a plurality of smooth muscle cells are arranged to form an inner layer of the tube-like structure 231 and a second set of multicellular bodies 1" comprising fibroblasts are arranged for form an outer layer of the tube-like structure. Accordingly, endothelial cells are more concentrated in an inner portion of the tube-like structure 231, smooth muscle cells are more concentrated in a center portion of the tube-like structure, and fibroblasts are more concentrated in an outer portion of the tube-like structure, such that a ratio of the number of fibroblasts to the number of non-fibroblasts in the second set of multicellular bodies 1" is greater than a ratio of the number of fibroblasts to the number of non-fibroblasts in the first set of multicellular bodies 1'. In another example, a first set of multicellular bodies 1' each comprising endothelial cells are arranged to form an inner layer of the tube-like structure 231 and a second set of multicellular bodies 1" each comprising and a plurality of smooth muscle cells and a plurality of fibroblasts are arranged for form an outer layer of the tube-like structure. Accordingly, endothelial cells are more concentrated in an inner portion of the tube-like structure 231, smooth muscle cells are more concentrated in a center portion of the tube-like structure, and fibroblasts are more concentrated in an outer portion of the tube-like structure, such that a ratio of the number of endothelial cells to the number of non-endothelial cells in the first set of multicellular bodies 1' is greater than a ratio of the number of endothelial cells to the number of non-endothelial cells in the second set of multicellular bodies 1".

Figure 7A:
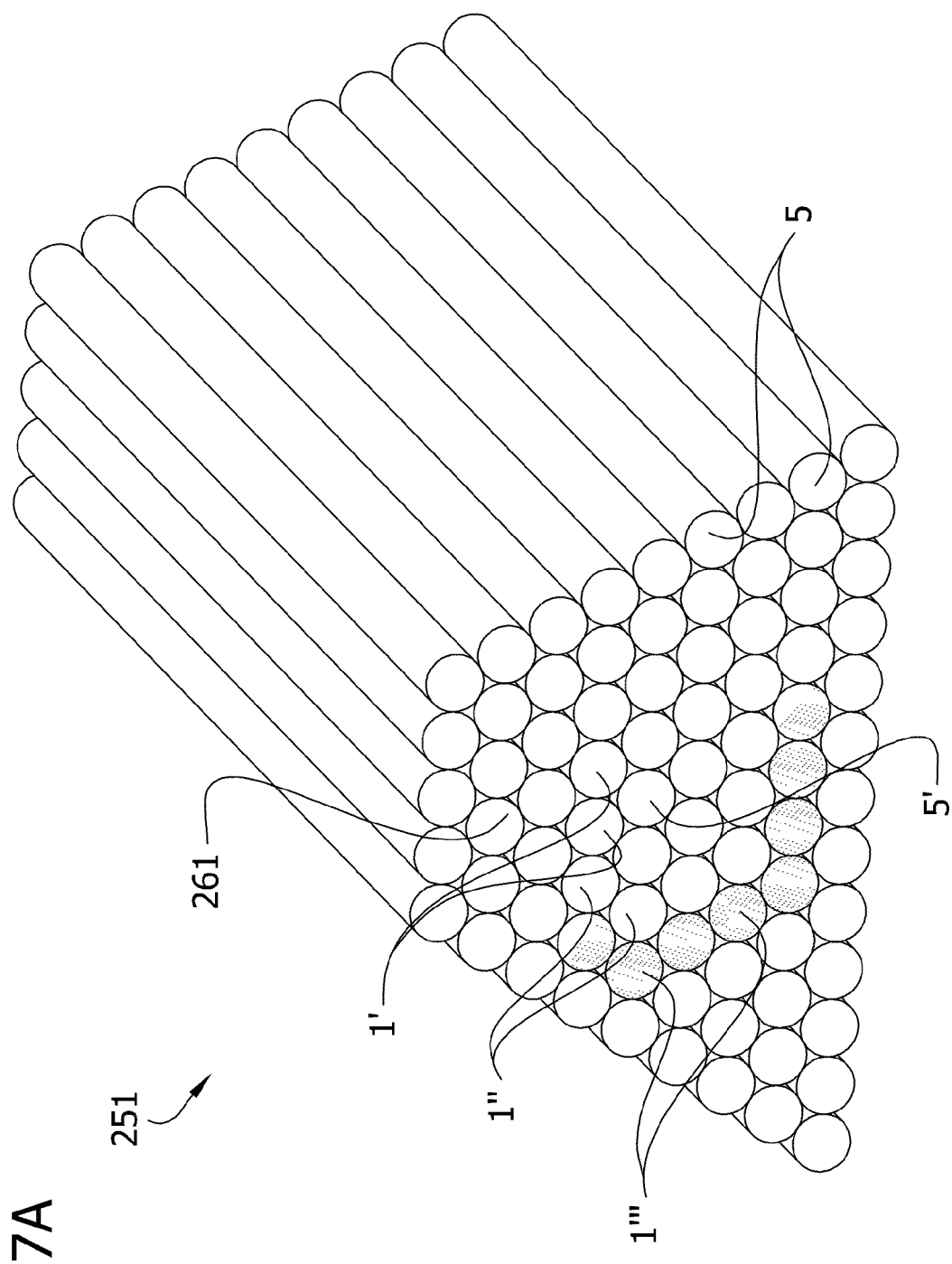

FIG. 7A illustrates another example of a three-dimensional structure 251 of the present invention. This structure 251 is substantially the same as the structure illustrated in FIG. 7 except that it also includes a third set of multicellular bodies 1'''. A majority of the cells in the multicellular bodies 1''' in the third set are of a cell type that is different from each of the cell types constituting the majority cell type for the respective multicellular bodies 1', 1" in the first and second sets. The multicellular bodies 1''' in the third set are suitably arranged in a generally hexagonal configuration surrounding and adjoining the multicellular bodies 1" in the second set. Thus, the multicellular bodies 1''' in the third set suitably surround the multicellular bodies 1" in the second set and the multicellular bodies 1' in the first set. Together, the multicellular bodies 1', 1", 1''' suitably form a tube-like structure 261 formed by three layers of multicellular bodies. One or more lumen-forming filler bodies 5' extends axially through the tube-like structure 261. If the structure 251 is to be used to form an engineered blood vessel, the majority of the cells in the multicellular bodies 1' in the first set are suitably endothelial cells, the majority of the cells in the multicellular bodies 1" in the second set are suitably smooth muscle cells, and the majority of the cells in the multicellular bodies 1''' in the third set are suitably fibroblasts, such that a ratio of the number of fibroblasts to the number of non-fibroblasts in the third set of multicellular bodies 1''' is greater than a ratio of the number of fibroblasts to the number of non-fibroblasts in the first set of multicellular bodies 1' or the second set multicellular bodies 1". However, the multicellular bodies 1', 1", 1''' can have other majority cell types within the scope of the invention.

Figure 8:
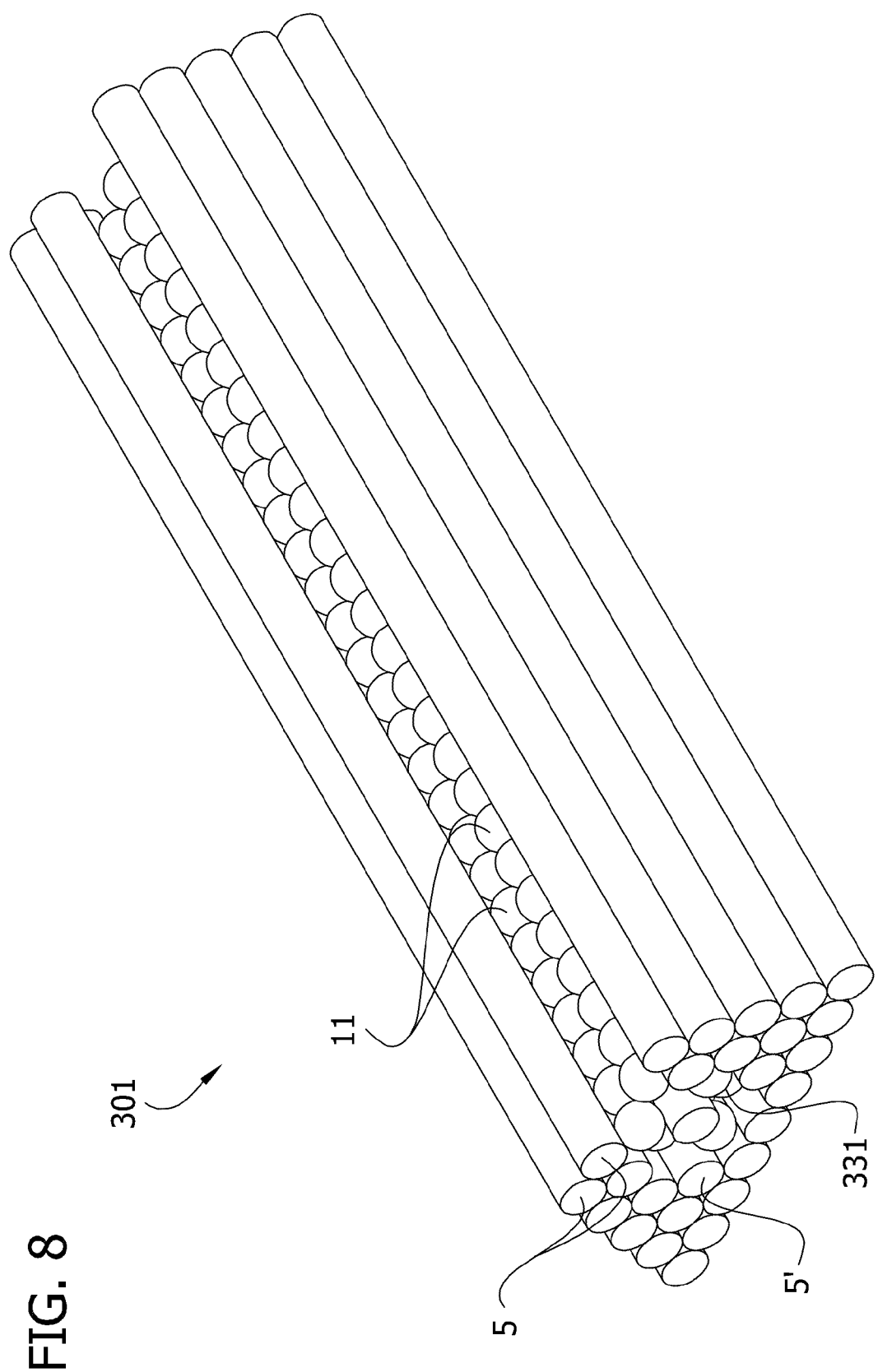

Another embodiment of a three-dimensional structure 301 of the present invention is illustrated in FIG. 8. Except as noted, this structure 301 is substantially identical to the structure 101 described above and illustrated in FIG. 2. In this embodiment, each of the elongate cylindrical multicellular bodies 1 used in the structure 101 illustrated in FIG. 2 has been replaced with a series of substantially spherical multicellular bodies 11. The spherical multicellular bodies 11 are suitably produced according to the methods described above for producing a self-supporting multicellular body. Of course, the shape of the spherical multicellular bodies 11 is different from the multicellular body 1 described above because they do not have any of its elongate characteristics. The spherical multicellular bodies 11 are suitably arranged to form a tube-like structure 331 surrounding one or more lumen-forming filler bodies 5'. To facilitate fusion of the spherical multicellular bodies, each series (e.g., line) of multicellular bodies can be offset from neighboring series of multicellular bodies so the center of each spherical multicellular body is axially aligned with a point about half the distance between the centers of the adjacent spherical bodies in the neighboring series. This can facilitate fusion because it results in increased contact area between neighboring spherical multicellular bodies 11. Although there is only one layer of multicellular bodies 11 surrounding the one more lumen-forming filler bodies 5' in FIG. 8, the multicellular bodies 1', 1", and 1'" in FIG. 7 or 7A can be also be replaced with spherical multicellular bodies 11. The spherical multicellular bodies provide the same options with respect to cell type, combinations of cell types in different multicellular bodies, and mixtures of cell types within the multicellular bodies as the elongate multicellular bodies.

In another embodiment of a three-dimensional structure of the present invention which is not illustrated, this structure is substantially identical to the structure 101 described above and illustrated in FIG. 2. In this embodiment, each of the elongate cylindrical filler bodies used in the structure 101 illustrated in FIG. 2 has been replaced with a series of substantially spherical filler bodies. The spherical filler bodies are suitably produced according to the methods described above for producing a self-supporting filler body. Of course, the shape of the spherical filler bodies is different from the filler body described above because they do not have any of its elongate characteristics. To facilitate stacking of the spherical filler bodies, each series (e.g., line) of filler bodies can be offset from neighboring series of filler bodies so the center of each spherical filler body is axially aligned with a point about half the distance between the centers of the adjacent spherical bodies in the neighboring series. This can facilitate stacking because it results in increased contact area between neighboring spherical filler bodies. The spherical filler bodies provide the same options with respect to materials (e.g., agarose, etc.) as the elongate filler bodies.

In another embodiment of a three-dimensional structure of the present invention which is not illustrated, the structure is substantially identical to the structure shown in FIG. 8 except that the structure also includes the spherical filler bodies as described above to replace at least some of the elongate filler bodies as shown in FIG. 8.

Figure 9:
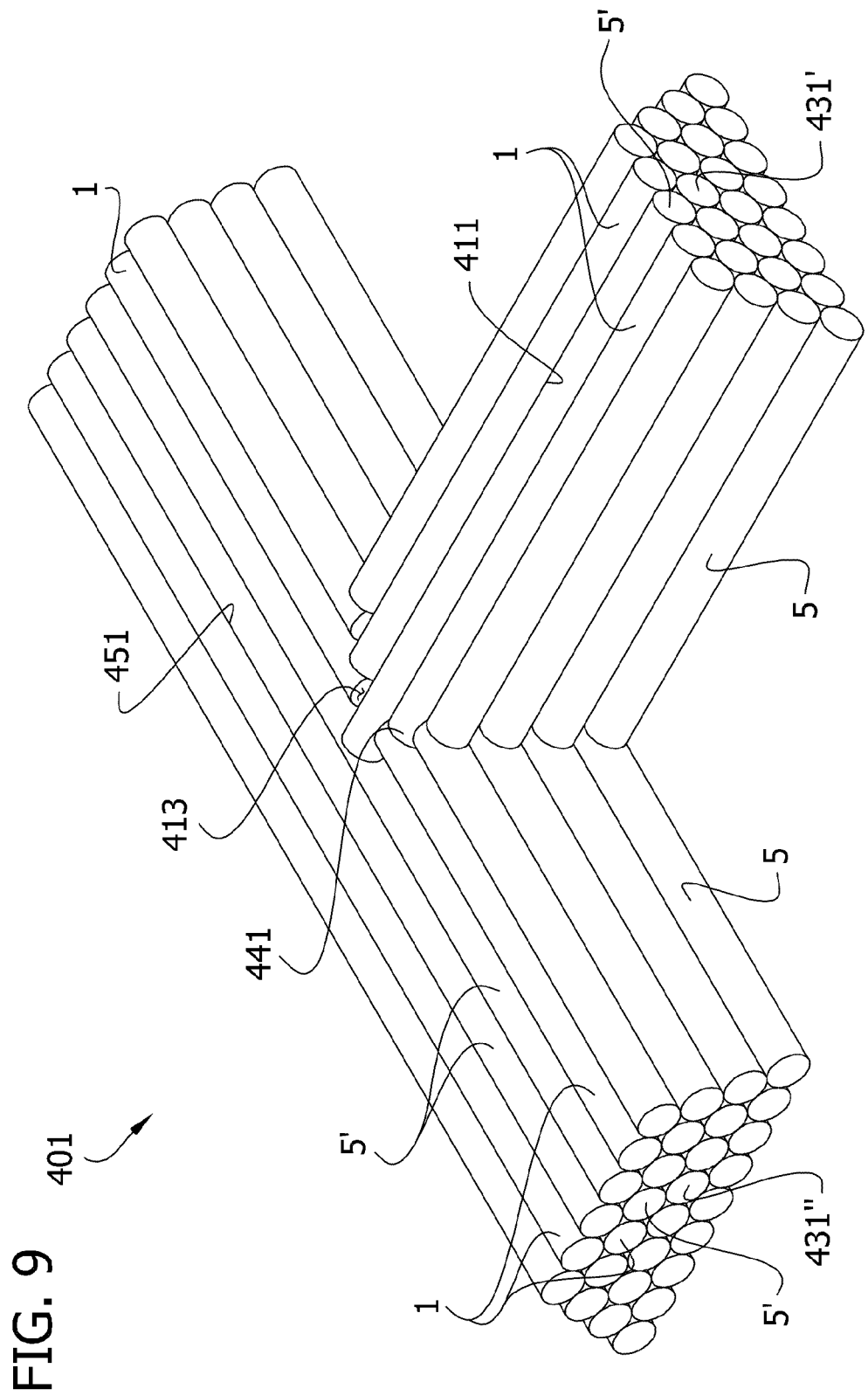

FIG. 9 illustrates a portion of another embodiment of a three-dimensional structure, generally designated 401. This structure is suitably an arrangement of elongate multicellular bodies 1, which can be substantially identical to the multicellular body 1 described above and a plurality of filler bodies 5. In FIG. 9 some of the multicellular bodies 1 and filler bodies 5 have been removed to show the internal arrangement of the multicellular bodies and filler bodies. In this structure 401, one or more of the filler bodies 5 are arranged to be lumen-forming filler bodies 5'. As illustrated, the lumen-forming filler bodies 5' are arranged to prevent ingrowth of cells from the multicellular bodies into first and second elongate spaces 411, 413. The lumen-forming filler bodies 5' are substantially surrounded by the multicellular bodies 1. For example, the multicellular bodies are suitably arranged to form a first tube-like structure 431' surrounding the first elongate space 411 and a second tube-like structure 431" surrounding the second elongate space 413. Although the tube-like structures 431', 431" are not shown in their entirety, they are similar to the tube-like structure 31 in FIG. 2 except as noted.

One of the tube-like structures 431" has a larger diameter than the other tube-like structure 431'. At least some of the elongate multicellular bodies 1 that form the smaller diameter tube-like structure 431' contact at least some of the elongate multicellular bodies 1 that form the larger diameter tube-like structure at an intersection 441 of the tube-like structures 431', 431". Further, at least one lumen-forming filler body 5' suitably extends through a gap 451 in the multicellular bodies 1 to connect an end of the first elongate space to the second elongate space so the lumens formed in the tube-like structure 431', 431" by the lumen-forming bodies 5' are connected to one another. Accordingly, maturation of this structure can produce a branched tubular engineered tissue, such as an engineered blood vessel. The example, illustrated in FIG. 9 produces a single branch, but the technique can be expanded to produce higher order branching structures, including structures having branches that have multiple different diameters. Also, the elongate multicellular bodies 1 in FIG. 9 can be replaced with spherical multicellular bodies 11, as illustrated by the structure 501 in FIG. 10. Further, the tube-like structures 431', 431" formed by the elongate multicellular bodies 1 (FIG. 9) or the spherical multicellular bodies (FIG. 10) can suitably be modified to include one or more additional sets of multicellular bodies in a manner similar to what is illustrated in FIGS. 7 and 7A. The same options with respect to cell type, combinations of cell types in different multicellular bodies, and mixtures of cell types within the multicellular bodies that have been described above also apply to the structures 401, 501 illustrated in FIGS. 9 and 10.

FIG. 1C illustrates another three-dimensional structure 601 of the invention. This structure 601 does not necessarily include any filler bodies. Instead a series of elongate multicellular bodies are arranged in side-by-side adjoining relation to form a sheet-like structure. Although there are only two multicellular bodies 1 in the sheet structure 601 illustrated in FIG. 1C, any number of additional multicellular bodies can be placed alongside these multicellular bodies so each multicellular body is in contact with at least one other multicellular body to increase the width of the sheet structure.

Methods of Making Three-Dimensional Structures

There are many different ways to use the multicellular bodies described above, including the elongate multicellular bodies 1 and the spherical multicellular bodies 11 (in some cases in conjunction with the filler bodies 5) to produce the three-dimensional biological constructs described above within the scope of the invention. For example, one method generally involves arranging a plurality of elongate multicellular bodies 1 according to a pattern such that each of the multicellular bodies contacts at least one other multicellular body and then allowing at least one (e.g., all) of the multicellular bodies to fuse to at least one other multicellular body to produce a desired three-dimensional biological engineered tissue. It is not necessary to include any filler bodies in the arrangement of multicellular bodies (see e.g., FIG. 1C). However, it is also possible to arrange a plurality of multicellular bodies (including the elongate multicellular bodies 1 and spherical multicellular bodies 11 described above) and one or more filler bodies 5 so each of the multicellular bodies contacts at least one other multicellular body or a filler body and then allow the multicellular bodies to fuse to form a desired three-dimensional biological engineered tissue.

Figure 10:
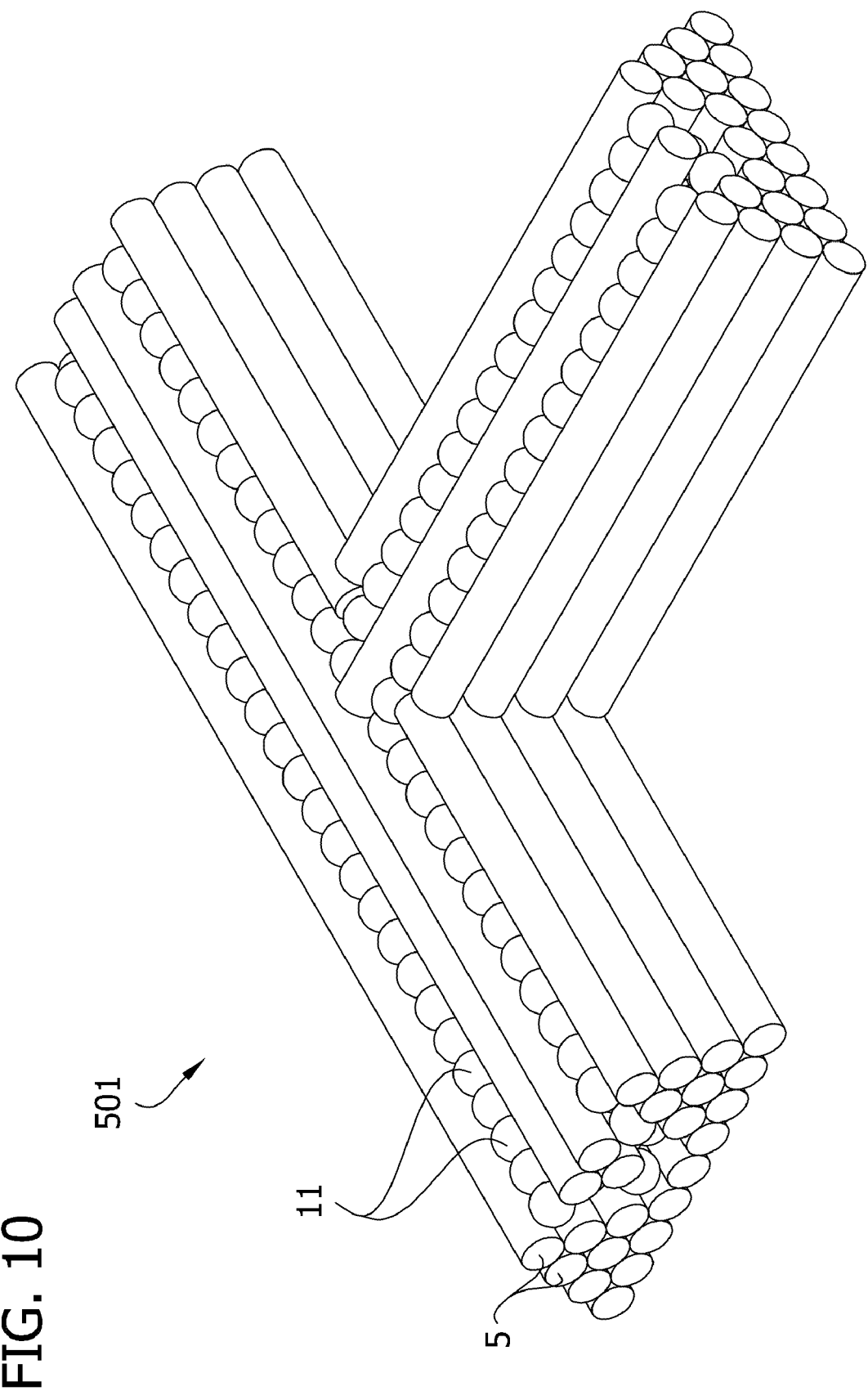
Figure 11:
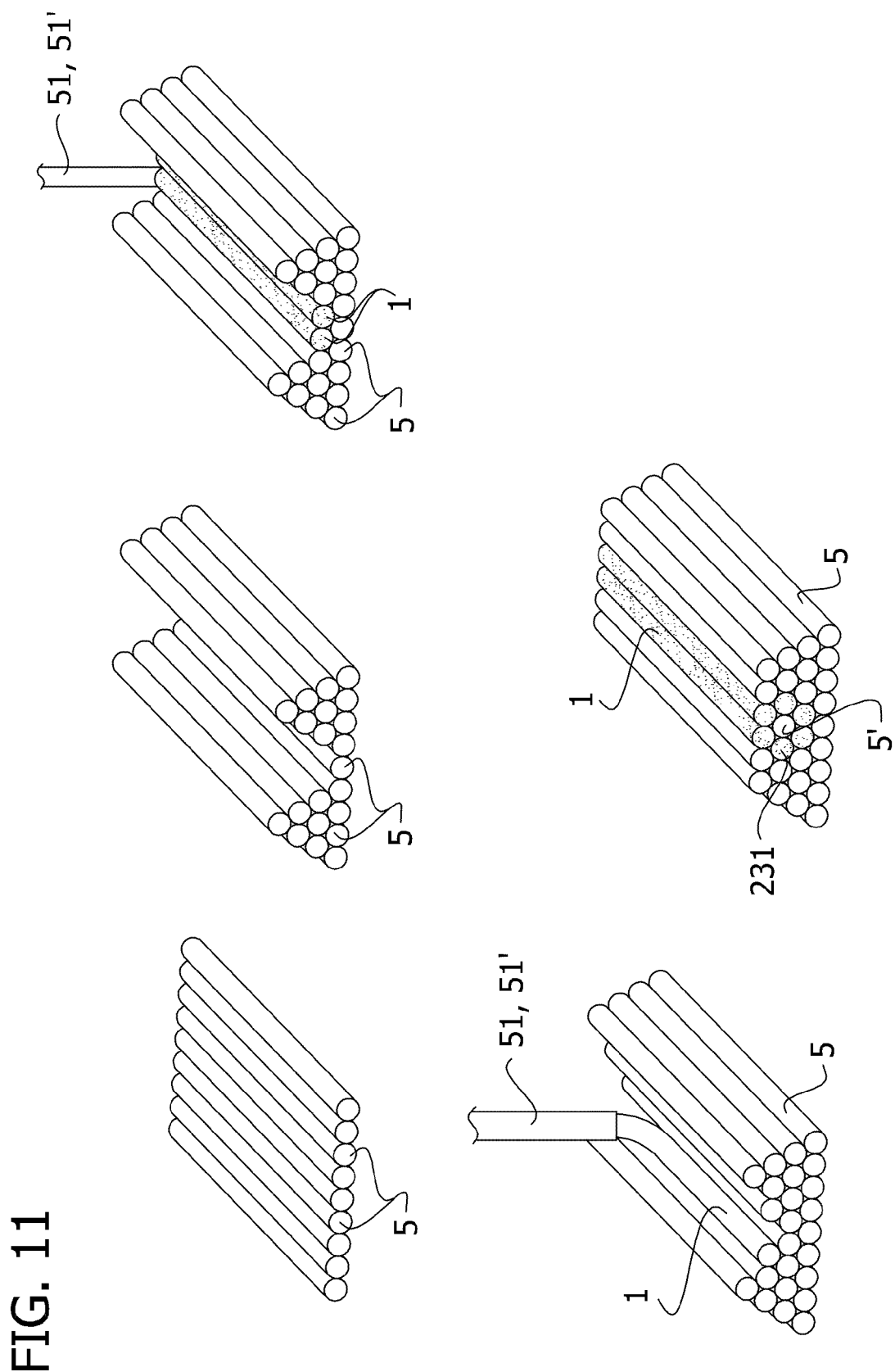
FIGS. 11 and 12 are schematic illustrations of various methods of making three-dimensional constructs from a plurality of multicellular bodies and filler bodies.

A number of methods may be used to deliver the multicellular bodies in a pre-determined pattern to produce the desired three-dimensional structure. For example, the multicellular bodies can be manually placed in contact with one another or a filler body, deposited in place by extrusion from a pipette, nozzle, or needle, or positioned in contact by an automated machine. As illustrated in FIG. 11, for example, one or more implements (which can suitably include the first shaping device 51 described above, the capillary pipette 51' that takes the multicellular body out of the mold 301, as described above, and/or a different implement) is used to pick up a multicellular body (e.g., to take them out of the mold 301 described above). The implement transports the multicellular body to an assembly area (for example, a glass surface) where a three-dimensional construct (e.g., as illustrated in any of FIG. 1C, 2, 7, 7A, or 8-10) is being assembled and dispenses or otherwise places the multicellular body in position relative to any other multicellular bodies and any filler bodies that have already been transported to the assembly area and placed in the construct that is being assembled.

After the multicellular body has been placed in its position, the process is suitably repeated to add another multicellular body or a filler body to the construct (e.g., by placing it alongside a multicellular body that has already been placed in the construct). If the construct that is being assembled includes one or more filler bodies, another implement (which is not shown, but which may be similar to the shaping device 51 or capillary pipette 51') is suitably used to pick up a filler body 5 (or make a filler body, as described above), transport the filler body to the assembly area, and dispense or otherwise place the filler body in its position within the construct that is being assembled whenever a filler body is needed. The implement 51, 51' used to transport multicellular bodies to the assembly area is suitably carried by a printing head of a bioprinter or other automated apparatus operable to arrange the multicellular bodies and filler bodies in a desired pattern. For example, one suitable bioprinter is disclosed in U.S. Patent App. No. 20040253365, which is hereby incorporated by reference. Those skilled in the art of tissue engineering will be familiar with other suitable bioprinters and similar apparatus that can be used to arrange the multicellular bodies (and filler bodies if they are used) into a suitable construct. The implement used to transport filler bodies to the assembly area is suitably part of another head of the bioprinter. A bioprinter can have multiple heads and/or the various implements 51, 51' for transporting the multicellular bodies and filler bodies can be loaded sequentially into one or more bioprinter heads. Although it may be desirable to use a bioprinter or similar apparatus to assemble the construct automatically, the methods described herein can be performed manually (e.g., using one or more capillary pipettes) within the scope of the invention.

Figure 12:
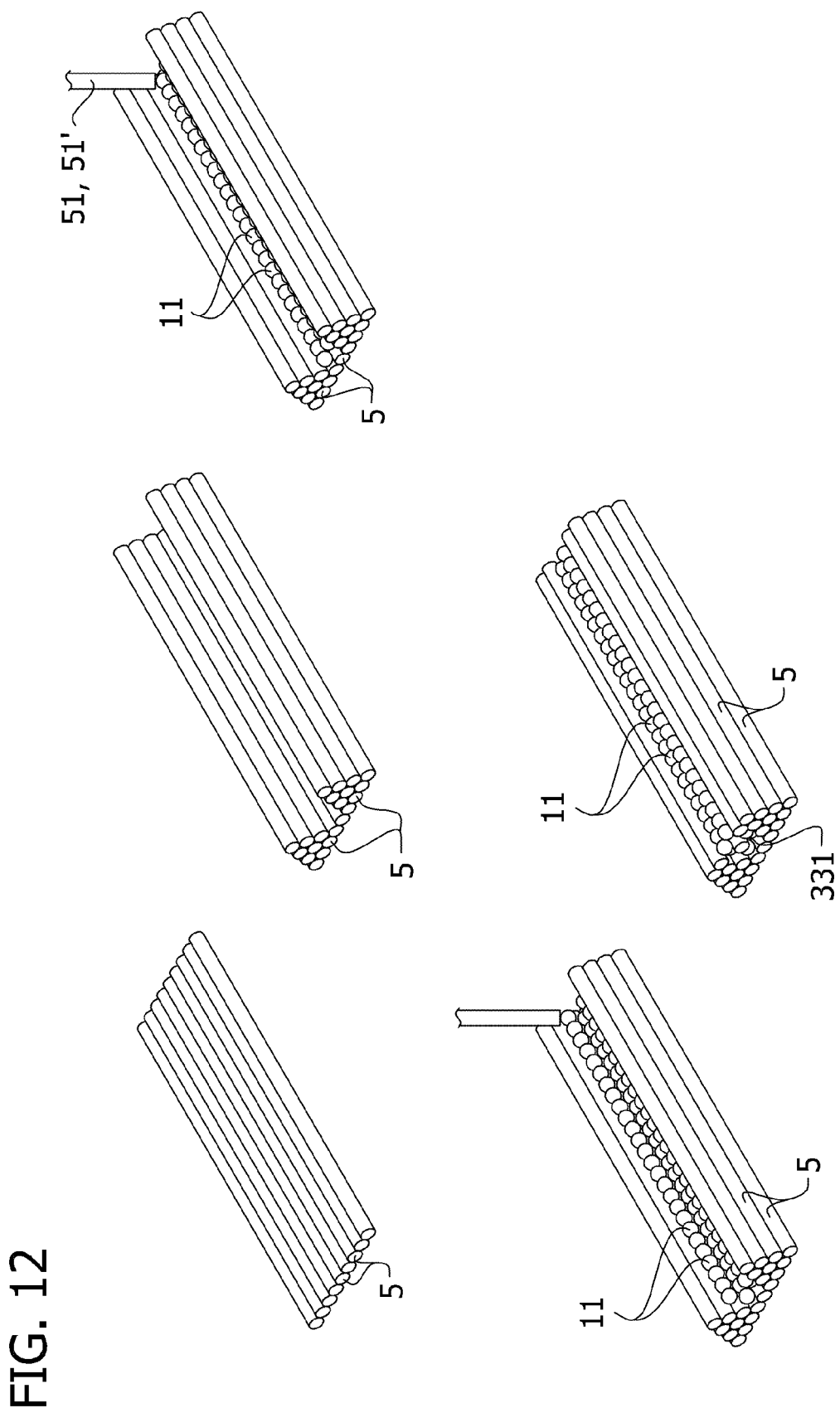

As illustrated in FIG. 11, the multicellular bodies 1 are suitably placed (e.g., stacked) on top of one or more filler bodies 5. The multicellular bodies 1 are suitably placed adjacent the other multicellular bodies and/or filler bodies 5. Thus, the multicellular bodies 1 are not pushed into or embedded in any of the filler bodies 5. This can be referred to as "printing in air" because the multicellular bodies are not dispensed into a gel or liquid. The method illustrated in FIG. 12 is substantially similar to the one illustrated in FIG. 11 except that the spherical multicellular bodies 11 are used instead of the elongate multicellular bodies 1 illustrated in FIG. 11. FIGS. 11 and 12 illustrate the process of making the constructs shown in FIGS. 2 and 8, respectively, but it is understood that constructs such as those illustrated in FIGS. 1C, 7, 7A, 8, and 9 and described above (and many others) can be produced in substantially the same way within the scope of the invention.

Once assembly of the construct is complete, a tissue culture medium is suitably poured over the top of the construct. The tissue culture medium can enter the spaces 17 between the multicellular bodies and the filler bodies to support the cells in the multicellular bodies. The multicellular bodies in the three-dimensional construct are allowed to fuse to one another to produce a biological engineered tissue. By "fuse," "fused" or "fusion", it is meant that the cells of contiguous multicellular bodies become adhered to one another, either directly through interactions between cell surface proteins, or indirectly through interactions of the cells with ECM components or derivatives of ECM components. After fusion, any filler bodies that were included in the construct are separated from the engineered tissue. In the case of a construct that includes a tube-like structure, for example, any filler bodies outside of the tube can be removed (e.g., by peeling them away from the tubular structure formed from the tube-like construct). Any of the lumen-forming filler bodies 5' inside the tubular structure are suitably pulled out of an open end of the tubular structure. The lumen-forming filler bodies 5' can suitably be made of a flexible material if desired to facilitate pulling the filler bodies out of the lumen, which may be helpful (e.g., if the engineered tissue is a branched tubular structure). Another option is to make the filler bodies 5 and any lumen-forming filler bodies 5' from a material that can be dissolved (e.g., by temperature change, light, or other stimuli) after fusion.

The present invention further provides another method of engineering a biological construct with a 3-D shape, such as a tissue, blood vessel, or an organ, using the multicellular bodies by further delivering a plurality of multicellular bodies according to a pre-determined 3-D pattern in a pre-selected receiving environment, so that the cellular units may fuse into the desired bio-construct. The two or more multicellular bodies that are fused may be of identical or differing shapes and sizes, and may contain the same or differing cell types. The multicellular bodies may be applied in bio-construct-engineering in number of ways. For example, two differently shaped multicellular bodies comprising a top half and a bottom half of a desired structure may be produced, and may be brought into contact and allowed to fuse. Alternatively, a plurality of multicellular bodies may be assembled and allowed to fuse into a desired shape, in combination with filler bodies. According to one embodiment, when the multicellular bodies are employed with the filler bodies, the engineering method may comprise the steps of A) delivering the plurality of multicellular bodies in a pre-determined combination with a plurality of filler bodies according to the pre-determined pattern to form a layered construct, whereby the multicellular bodies and the filler bodies are contiguous, B) depositing the layered construct into a pre-selected controlled environment for maturation, whereby the multicellular bodies fuse with each other to result in a fused construct, and C) removing the filler bodies from the fused construct to produce the desired biological construct.

Furthermore, each multicellular body 1, 11 may be comprised of two or more cell types, creating a bio-construct containing two or more cell types. These cell types may be expected to segregate based on their affinity to the surface of the structure or other forces, such as cell-cell interactions. For example, cylindrical molded multicellular body may be created from a mixture of smooth muscle cells and endothelial cells to create a tubular structure, such as a transplantable blood vessel. These multicellular bodies may then be placed into position (e.g., as in FIG. 2), and allowed to fuse into a tubular construct. The endothelial cells, upon perfusion of the construct through its lumen may be expected to move to the central internal surface of the tubular construct, while the smooth muscle cells dominate the exterior. As another example, if the multicellular bodies 1 include a mixture of endothelial cells and fibroblasts, the endothelial cells may be expected to move to the central internal surface of the tubular construct upon perfusion of the construct through its lumen, while the fibroblasts dominate the exterior. As another example, if the multicellular bodies 1 include a mixture of smooth muscle cells and fibroblasts, the smooth muscle cells may be expected to move to the central internal surface of the tubular construct, while the fibroblasts dominate the exterior. As a further example, if the multicellular bodies 1 include a mixture of endothelial cells, smooth muscle cells, and fibroblasts, the endothelial cells may be expected to sort to an inner layer of the construct upon perfusion of the construct through its lumen, the fibroblasts may be expected to sort to an outer layer of the construct, and the smooth muscle cells may be expected to sort to a middle layer sandwiched between the inner endothelial layer and the outer fibroblast layer.

Three-Dimensional Engineered Tubular Structures

Figure 13:
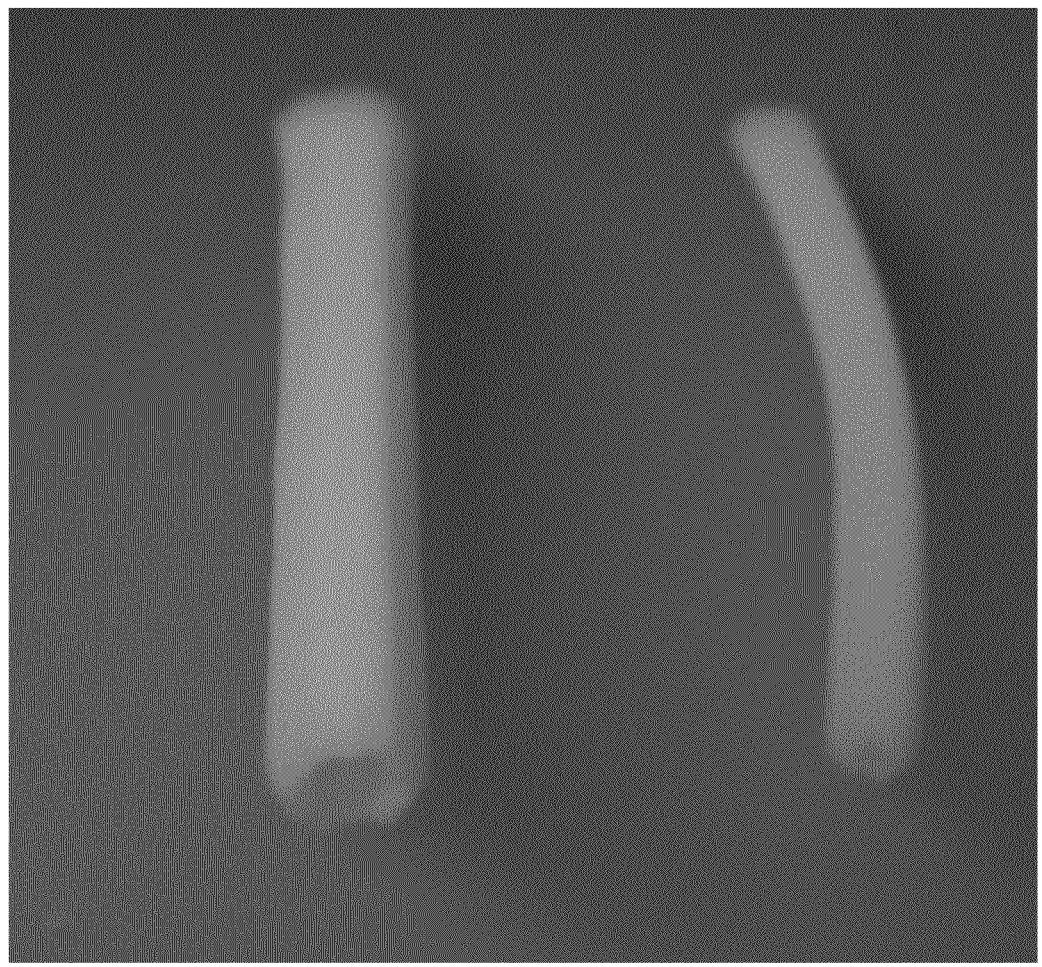
FIG. 13 is a photograph of two tubular structures engineered according to the methods described herein having outside diameters of 1200 microns and 900 microns, respectively.
Figure 14:
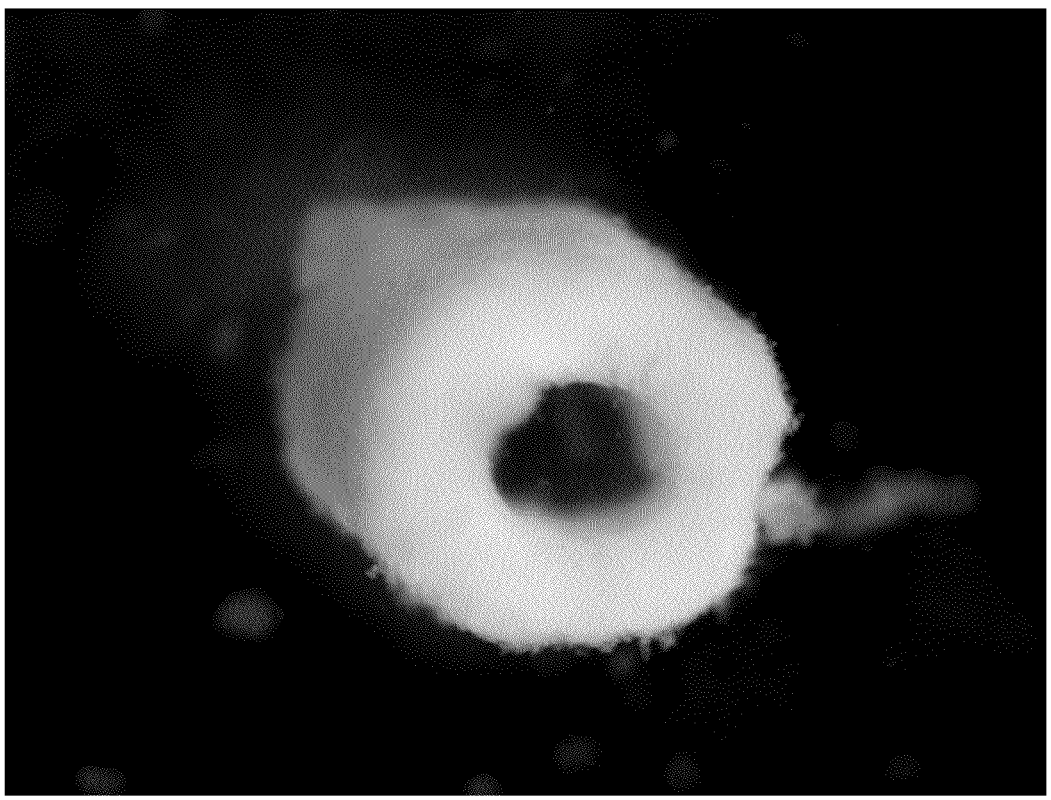
FIG. 14 is a photograph of another tubular structure engineered according to the methods described herein.

The invention further provides an example of a cellular tubular construct engineered according to the invention method. FIGS. 13 and 14 show actual tubular bio-constructs built by the processes described herein. FIG. 13 shows the sides of two different tubular bio-constructs, after the maturation and removal of the filler bodies. FIG. 14 shows the end of a tubular construct after all filler bodies have been removed.

Figure 15:
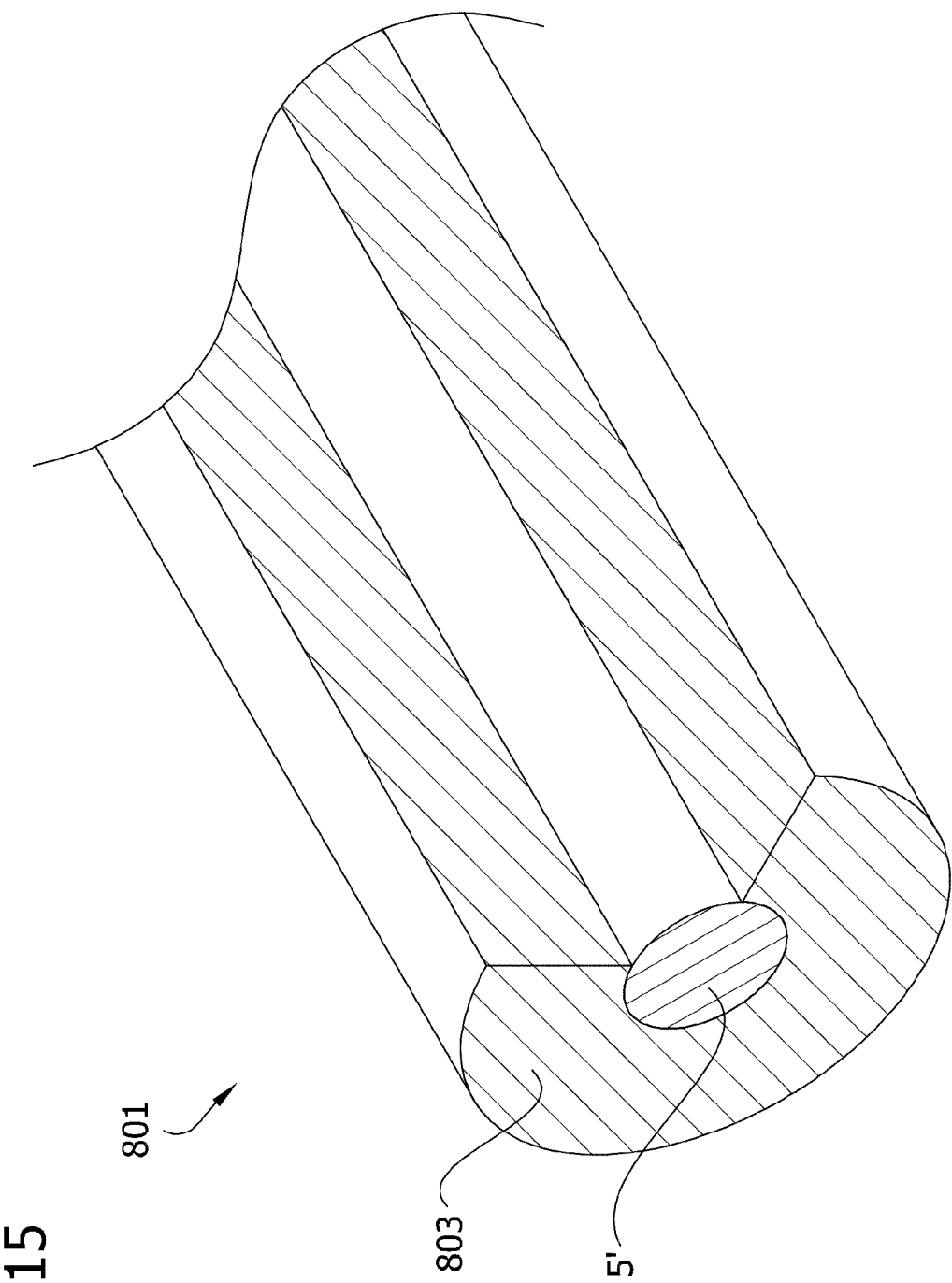
FIG. 15 is a schematic perspective of one embodiment of a tubular structure engineered according to the methods described herein in combination with a filler body in the lumen of the tubular structure.

One embodiment of such a construct is illustrated schematically in FIG. 15, and is generally designated 801. The three-dimensional tubular structure 801 includes at least one filler body 5' and a plurality of living cells which are cohered to one another, the cells forming a tubular structure 801 substantially surrounding the at least one filler body. The filler body 5' comprises a compliant biocompatible material that resists migration and ingrowth of cells into the material and which resists adherence of cells to the material. The biocompatible material may also be permeable to nutrients.

The three-dimensional tubular structure suitably has a length of at least about 1000 microns, more suitably a length of at least about 5 centimeters (e.g., in the range of about 5 centimeters to about 30 centimeters). In some cases the three-dimensional tubular structure suitably has a length of less than about 30 centimeters. As with the multicellular bodies, there is no theoretical upper limit on the length of the three-dimensional tubular structure, and thus it is recognized that it is possible to make a three-dimensional tubular structure having a length in excess of 30 centimeters (or any arbitrary length different from 30 centimeters) within the scope of the invention, so long as a person is willing to overcome practical difficulties associated with making a long tubular structure (e.g., obtaining a sufficient quantity of cells, handling long multicellular bodies which may be needed to make such a structure, etc.)

Like the individual multicellular bodies, the three-dimensional tubular structure can be composed of a single cell type, or can include multiple cell types. The three-dimensional tubular structure can be made using any of the various cell types discussed above. Thus, for example, the tubular structure can be substantially homocellular (i.e., almost all of the living cells in the tubular structure are cells of a single cell type, subject to some tolerance for low levels of impurities, including a relatively small number of cells of a different cell type that have no more than a negligible impact on the maturation of the tubular construct). More specifically, the cells of the tubular structure can suitably consist essentially of cells of a single cell type. Alternatively, the cells of the tubular structure can suitably comprise living cells of a first cell type and at least about 90 percent of the cells are cells of the first cell type.

The tubular structure can also be heterocellular, including two or more different cell types. If the tubular structure is a vascular tubular structure, the tubular structure will advantageously include cell types typically found in vascular tissue (e.g., endothelial cells, smooth muscle cells, fibroblasts, etc.). In one example, the cells of the tubular structure include a plurality of living cells of a first cell type and a plurality of living cells of a second cell type, the second cell type being different from the first cell type. In another example, the cells of the tubular structure include a plurality of living cells of a first cell type, a plurality of living cells of a second type, and a plurality of living cells of a third cell type. Thus, for vascular tubular structures, the cells can suitably include: (i) endothelial cells and smooth muscle cells; (ii) smooth muscle cells and fibroblasts; (iii) endothelial cells and fibroblasts; or (iv) endothelial cells, smooth muscle cells, and fibroblasts. Moreover, in vascular tubular structures, the endothelial cells, smooth muscle cells, and fibroblasts can advantageously form layers mimicking the layers of cell types found in naturally occurring tissue. Thus, in one example, in a vascular tubular structure containing endothelial cells and smooth muscle cells, the endothelial cells advantageously form an inner layer substantially surrounding said at least one filler body and the smooth muscle cells advantageously form a layer substantially surrounding said at least one filler body and the inner layer formed by the endothelial cells. In another example, in a vascular tubular structure containing endothelial cells and fibroblasts, the endothelial cells advantageously form an inner layer substantially surrounding said at least one filler body and the fibroblasts advantageously form a layer substantially surrounding said at least one filler body and the inner layer formed by the endothelial cells. As another example, in a vascular tubular structure containing smooth muscle cells and fibroblasts, the smooth muscle cells advantageously form an inner layer substantially surrounding said at least one filler body and the fibroblasts advantageously form a layer substantially surrounding said at least one filler body and the inner layer formed by the smooth muscle cells. In another example, in a vascular tubular structure which contains endothelial cells, smooth muscle cells, and fibroblasts, the endothelial cells suitably form an inner layer substantially surrounding said at least one filler body, the smooth muscle cells suitably form a second layer substantially surrounding said at least one filler body and the inner layer formed by the endothelial cells, and the fibroblasts suitably form a third layer substantially surrounding said at least one filler body, the inner layer formed by the endothelial cells, and the second layer formed by the smooth muscle cells.

Also within the scope of the invention are three-dimensional branched tubular structures. In one example of such a structure, a plurality of living cells form a branched tubular structure substantially surrounding one or more of the filler bodies which are lumen-forming filler bodies. The lumen-forming filler bodies are arranged to prevent ingrowth of the living cells into first and second elongate spaces, wherein an end of the first elongate space is adjacent a side of the second elongate space.

The compliant biocompatible material of the at least one filler body is selected from the group consisting of agarose, agar, hyaluronic acid, and polyethylene glycol. The at least one filler body is suitably separable from the tubular structure by pulling the filler body out of the tubular structure.

EXAMPLES

Example 1

Preparation of Multicellular Bodies and Tissue Engineering Using Pig Smooth Muscle Cells I. Pig Smooth Muscle Cells. Pig smooth muscle cells (SMCs) were grown in the same conditions used in previous studies. The medium composition was Dulbecco's Modified Eagle Medium (DMEM) low glucose supplemented with 10% porcine serum, 10% bovine serum, 50 mg/L of proline, 20 mg/L of alanine, 50 mg/L of glycine, 50 mg/L of ascorbic acid, 12 µg/L, of Platelet Derived Growth Factor-BB (PDGF-BB), 12 µg/L of Basic Fibroblast Growth Factor (bFGF), 3.0 µg/L of $CuSO_4$, 0.01M of HEPES buffer, and $1.0 \times 10^5$ units/L of penicillin and streptomycin. The cells were grown on gelatin (gelatin from porcine skin) coated 10 cm Petri dishes and incubated at 37° C., 5% $CO_2$. The SMCs were subcultured up to passage 7 before being used for multicellular body (e.g., cellular unit) preparation. Eighteen confluent Petri (i.e. cell culture) dishes were necessary to prepare 24 cellular units and 4 tubes (outside diameter (OD): 1.5 mm; inside diameter (ID): 0.5 mm; length (L): 5 cm).

II. Agarose Mold.

(i) Preparation of a 2% agarose solution. 2 g of Ultrapure Low Melting Point (LMP) agarose was dissolved in 100 ml of ultrapure water/buffer solution (1:1, v/v). The buffer solution can be PBS=Dulbecco's phosphate buffered saline 1× or HBSS=Hanks' balanced salt solution 1×. The agarose solution was placed in a beaker containing warm water (over 80° C.) and held on the hot plate until the agarose dissolves completely. The agarose solution remains liquid as long as the temperature is above 36° C. Below 36° C., a phase transition occurs, the viscosity increases, and finally the agarose forms a gel.

(ii) Preparation of an agarose mold. An agarose mold was formed using a Teflon print (i.e., a Teflon tool) (FIGS. 5A-5C) that fits into a Petri dish (10 cm diameter). The assembly (Teflon print+Petri dish) was maintained horizontally and about 40 ml of a pre-warmed agarose was poured in the Petri dish through a hole in the Teflon print. After removing all air bubbles, the assembly was placed at 4° C. for at least 1 hour. After complete gelification of the agarose, the Teflon print was removed and grooves were visible in the agarose (see the grooves 305 in FIG. 4D). 10 ml of medium was added to the mold.

III. Preparation of the Multicellular Bodies.

The medium was removed from confluent Petri dishes and the cells were washed with 10 ml of HBSS+2 mM $CaCl_2$. 1.5 ml of trypsin 0.1% was spread evenly to detach the cells from the surface. 5 ml of medium+2 mM $CaCl_2$ was added to the Petri dish. The cell suspension is centrifuged at 900 g for 5 minutes. After removal of the medium (i.e., the supernatant), the cell pellet was resuspended in 200 µl of medium+2 mM $CaCl_2$ and pumped up and down (i.e., vigorously pipetted) several times to break up cells clusters and obtain a single cell suspension. The solution was transferred into 2 ml Eppendorf tubes placed inside a 15 ml centrifuge tube. A high density cell paste was formed by centrifugation at 1300 g for 2 minutes. The medium (i.e., supernatant) was removed and the cell paste was transferred by aspiration into capillary tubes (OD 1 mm, ID 0.5 or 0.3 mm) inserted into 1 ml tips mounted on an 1 ml Eppendorf pipettor. The capillary tubes containing the cell paste were incubated in medium+2 mM $CaCl_2$ for 15 minutes at 37° C., 5% $CO_2$. The shaped cell paste was extruded from the capillary tubes with the plunger into the grooves of an agarose mold filled with medium (FIG. 3C). The mold was placed in the incubator overnight. The next day, the mature multicellular bodies were aspirated (i.e., sucked back) manually into capillary tubes (FIG. 3D) and placed into medium until further use.

IV. Tissue Engineering.

Ten ml of a pre-warmed solution of 2% agarose was deposited in a 10 cm diameter Petri dish and evenly spread to form a uniform layer. Agarose gel was prepared at 4° C. in a fridge. Capillary tubes were filled up with an agarose solution and rapidly cooled (using cold blowing air or a cold PBS solution) to form the filler bodies. For lumen-forming filler bodies, the agarose concentration was 4%; for all other filler bodies, the agarose concentration was 2%. Under a binocular microscope, a filler body was extruded from the capillary tube using a piston or wire and a 5 cm agarose rod (i.e., filler body) was laid down straight on the agarose layer inside the Petri dish. A second filler body was juxtaposed to the first one and so on until 9 filler bodies were deposited that form the first layer. The 6 filler bodies that constitute the second layer were deposited as shown in FIG. 11. Two multicellular bodies were deposited in the 4th and 5th positions to form the first layer of a tube. The third layer was formed by deposition of 5 filler bodies and 2 multicellular bodies in the 3rd and 5th positions. The fourth layer was composed of 4 filler bodies and 2 multicellular bodies in the 3rd and 4th positions. The fifth layer was composed of 5 filler bodies (FIG. 2). Throughout the deposition process, small amounts of medium (10 µl at the time) were added on the side of the construct to avoid dehydration of the material (agarose and multicellular bodies). 0.5 to 1 ml of liquid agarose (37° C.<T<40° C.) was poured around and on top of the construct to maintain its integrity. After gelification, medium was added until the construct was totally submerged. The construct was placed in the incubator. After 48 hours, the multicellular bodies had fused with one another. The agarose was removed by peeling it off of the outer surface of the tubular structure and by pulling the filler body which filled the lumen of the tubular structure out of the tubular structure. The tube was then transferred into a bioreactor for further maturation. Any commercially available bioreactor can be used for the maturation.

Example 2

Alternative Procedure for Preparing Multicellular Bodies and for Tissue Engineering I. Growth Conditions for Cells of Various Types Chinese Hamster Ovary (CHO) cells transfected with N-cadherin were grown in Dulbecco's Modified Eagle Medium (DMEM) supplemented with 10% Fetal Bovine Serum (FBS), antibiotics (100 U/mL penicillin streptomycin and 25 µg/mL gentamicin) and 400 µg/ml geneticin. Besides gentamicin all antibiotics were purchased from Invitrogen.

Human Umbilical Vein Smooth Muscle Cells (HUSMCs) and Human Skin Fibroblasts (HSFs) were purchased from the American Type Culture Collection (CRL-2481 and CRL-2522 respectively). HUSMCs were grown in DMEM with Ham's F12 in ratio of 3:1, 10% FBS, antibiotics (100 U/mL penicillin-streptomycin and 25 µg/mL gentamicin), 20 µg/mL Endothelial Cell Growth Supplement (ECGS), and Sodium Pyruvate (NaPy) 0.1M. Human skin fibroblasts (HSFs) were grown in DMEM with Ham's F12 in ratio of 3:1, 20% FBS, antibiotics (100 U/mL penicillin/streptomycin and 25 µg/mL gentamicin), glutamine 2 mM, NaPy 0.1M.

Freshly isolated porcine aortic smooth muscle cells (PASMCs) were grown in low glucose DMEM with 10% FBS, 10% porcine serum, L-ascorbic acid, copper sulfate, HEPES, L-proline, L-alanine, L-glycine, and Penicillin G.

All cell lines (except CHO) were cultured on 0.5% gelatin (porcine skin gelatin) coated dishes and were maintained at 37° C. in a humidified atmosphere containing 5% $CO_2$.

II. Preparation of Multicellular Bodies

Cell cultures were washed twice with phosphate buffered saline solution (PBS), treated for 10 min with 0.1% Trypsin, and the resulting cell suspension was centrifuged at 1,500 RPM for 5 min. Cells were resuspended in 4 ml of cell-type specific medium and incubated in 10-ml tissue culture flasks at 37° C. with 5% $CO_2$ on a gyratory shaker for one hour, for adhesion recovery, and then centrifuged at 1,500 RPM for 5 minutes. The cells were then resuspended and vigorously pipetted in 200 μl of medium and recentrifuged at 3,500 RPM for 2 minutes. The resulting cell pellets (the cell paste) were transferred into capillary tubes having 300 μm or 500 μm internal diameters and incubated at 37° C. with 5% $CO_2$ for 15 min.

For substantially spherical multicellular bodies, HSFs or CHO cells were used, and the partially cohered cell paste was mechanically extruded and cut into equal fragments that were allowed to round up overnight on a gyratory shaker at 37° C., 5% $CO_2$. Depending on the diameter of the capillary tubes, this procedure provided regular spheroids of defined size and cell number.

For elongate multicellular bodies, PASMCs, HUSMCs, or HSFs were used, and the partially cohered cell paste was mechanically extruded into specifically prepared non-adhesive Teflon or agarose molds using a bioprinter. After overnight maturation in the mold at 37° C., 5% $CO_2$, the multicellular bodies were cohesive enough to be deposited along with filler bodies to create a three-dimensional engineered tissue as described in Example 1.

III. Preparation of Filler Bodies

To prepare agarose rods, liquid agarose (temperature>40° C.) was loaded into capillary tubes (300 or 500 μm ID). For lumen-forming filler bodies, the agarose concentration was 4%; for all other filler bodies, the agarose concentration was 2%. Loaded capillary tubes were immersed into cold PBS (4° C.). As agarose did not adhere to the capillary tubes, upon gelation, continuous rods could easily be extruded by the bioprinter using another printing head.

IV. Immunohistochemistry

Tissues were fixed overnight in 4% paraformaldehyde. After dehydration, tissues were processed for paraffin infiltration and embedding. For global aspect, 5 μm sections were stained with hematoxylin-eosin. For immunohistochemistry, sections were incubated with the following antibodies: anti-cleaved caspase-3 (1:50 dilution of a rabbit anti-cleaved caspase-3 polyclonal antibody that reacts with mouse and human cleaved caspase-3); anti-smooth muscle actin (1:400 dilution of a mouse anti-human smooth muscle actin (1A4). Secondary antibodies (EnVision+, a horseradish peroxidase-labeled polymer conjugated with either anti-mouse or anti-rabbit antibodies) were visualized using DAB (3'-diaminobenzidine tetrahydrochloride). Sections were counterstained with Mayer's hematoxylin, and coverslipped for microscopic examination (IX70).

V. Tissue Engineering Using Substantially Spherical Multicellular Bodies.

To assemble the substantially spherical multicellular bodies into customized tubular structures of defined topology, a scaffold-free approach was designed based on the use of filler bodies (e.g. agarose rods) as building blocks. When agarose rods and substantially spherical and substantially uniform multicellular bodies were deposited layer-by layer, accurate control of tube diameter, wall thickness, and branching pattern was possible (FIG. 10).

Figure 16:
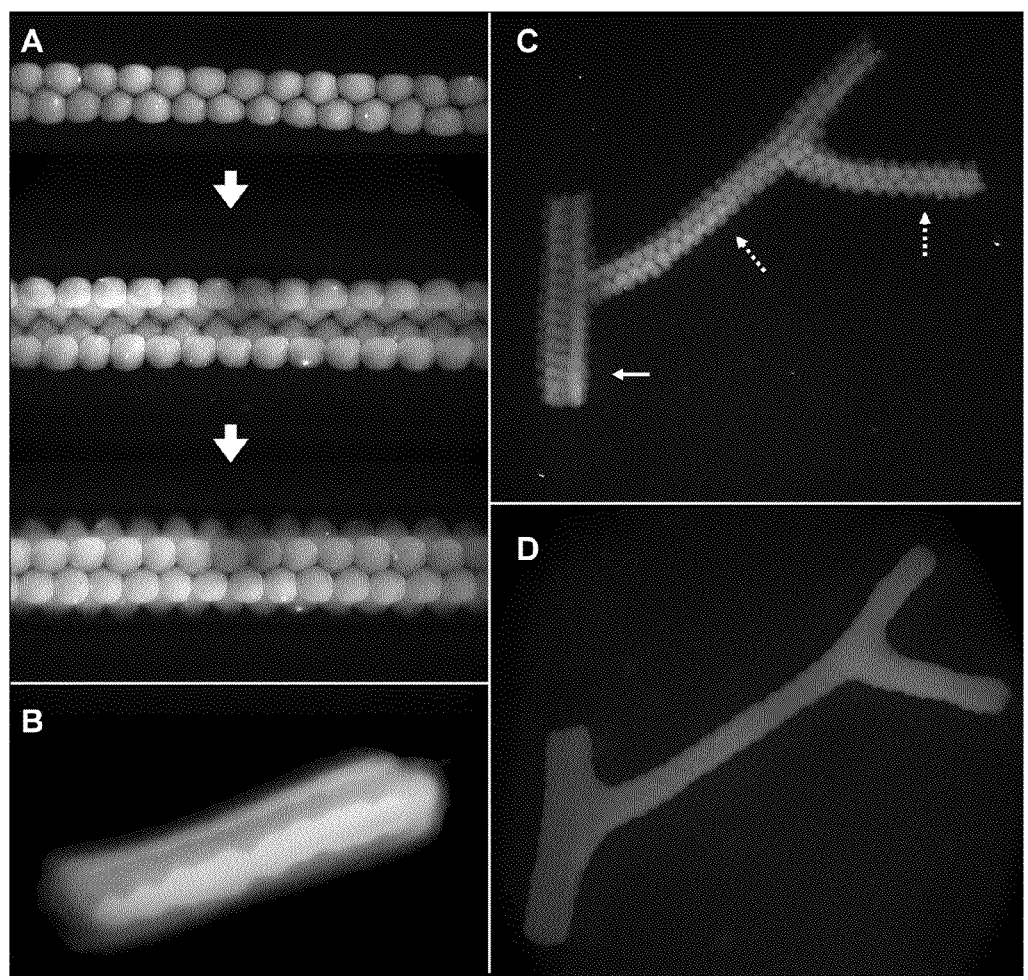
FIG. 16 includes a group of photographs illustrating fusion of spherical multicellular bodies to form a branched tubular structure.

Using this approach, straight tubes were initially built manually, according to the patterns shown in FIG. 8. The smallest tube was assembled using substantially spherical multicellular bodies made up of HSFs and was 900 μm in diameter with a wall thickness of 300 μm (FIG. 16A). Once assembled, the substantially spherical multicellular bodies fused with one another within 5 to 7 days to result in the final tubular construct. To study the fusion process in more detail, CHO cells stained with either green or red membrane dyes were used to create the substantially spherical multicellular bodies, which were then assembled according to the scheme shown in FIG. 8. Fusion of alternate sequences of green and red spheroids is shown in FIG. 16B and reveals a sharp fusion boundary with little intermingling, confirming earlier findings.

In addition to flexibility in tube diameter and wall thickness, the presented method, as its unique feature, provides a way to construct branched macrovascular structures. For this purpose, to ensure correct luminal connection, the different branches of the vascular tree were assembled simultaneously. A branched tubular structure having branches of distinct diameters (FIG. 16C) was built according to the pattern in FIG. 10 using 300 μm diameter substantially spherical multicellular bodies made up of HSFs. The branches were 1.2 mm (solid arrow) and 0.9 mm (broken arrows) in diameter (FIG. 16C). The substantially spherical multicellular bodies fused to one another in 5 to 7 days to form a fused branched tubular structure (FIG. 16D).

VI. Tissue Engineering to Create Single and Double-Layered Vascular Tubes Using Elongate Multicellular Bodies.

To improve speed, precision, and reproducibility and thereby adapt the method for potential clinical applications, the specifically built three-dimensional delivery device (i.e., bioprinter) was adapted for the deposition of filler bodies (e.g., agarose rods) and elongate multicellular bodies, keeping the same conceptual approach as described above (FIG. 2).

The computer-aided rapid prototyping bioprinting technology allowed for the controlled, simultaneous deposition of the filler bodies (e.g., agarose rods) and elongate multicellular bodies (e.g., multicellular cylinders) according to the same templates as before (FIG. 2). Deposition was carried out using a bioprinter equipped with two vertically moving print heads, one for the preparation and extrusion of agarose rods, the other for the deposition of multicellular cylinder. Loading, gelation and extrusion of agarose rods took place in a fully automated cycle. The capillary pipette-cartridge attached to the print head was first moved to a warm liquid agarose vial for loading. Next, to allow for the rapid gelation of the agarose, the loaded cartridge was immersed in a cold vial of PBS. Finally, the resulting agarose rod was extruded into a Petri Dish. When the deposition scheme called for the delivery of a multicellular cylinder), one such cylinder was drawn from the agarose mold into a capillary pipette. The capillary pipette was then loaded into the second print head and the multicellular cylinder extruded similarly to an agarose rod. Simple straight tubes of HUSMCs were printed according to the design shown in FIG. 2. The computer-aided motion and coordination of the two print heads assured the reproducibility of the pre-programmed pattern. After assembly, multicellular bodies made up of HUSMCs fused within two to four days into final tubular structures, and the supporting agarose rods were removed. Fused tubes of two distinct diameters (outside diameters of 1200 microns and 900 microns, respectively) are shown in FIG. 13.

Figure 17:
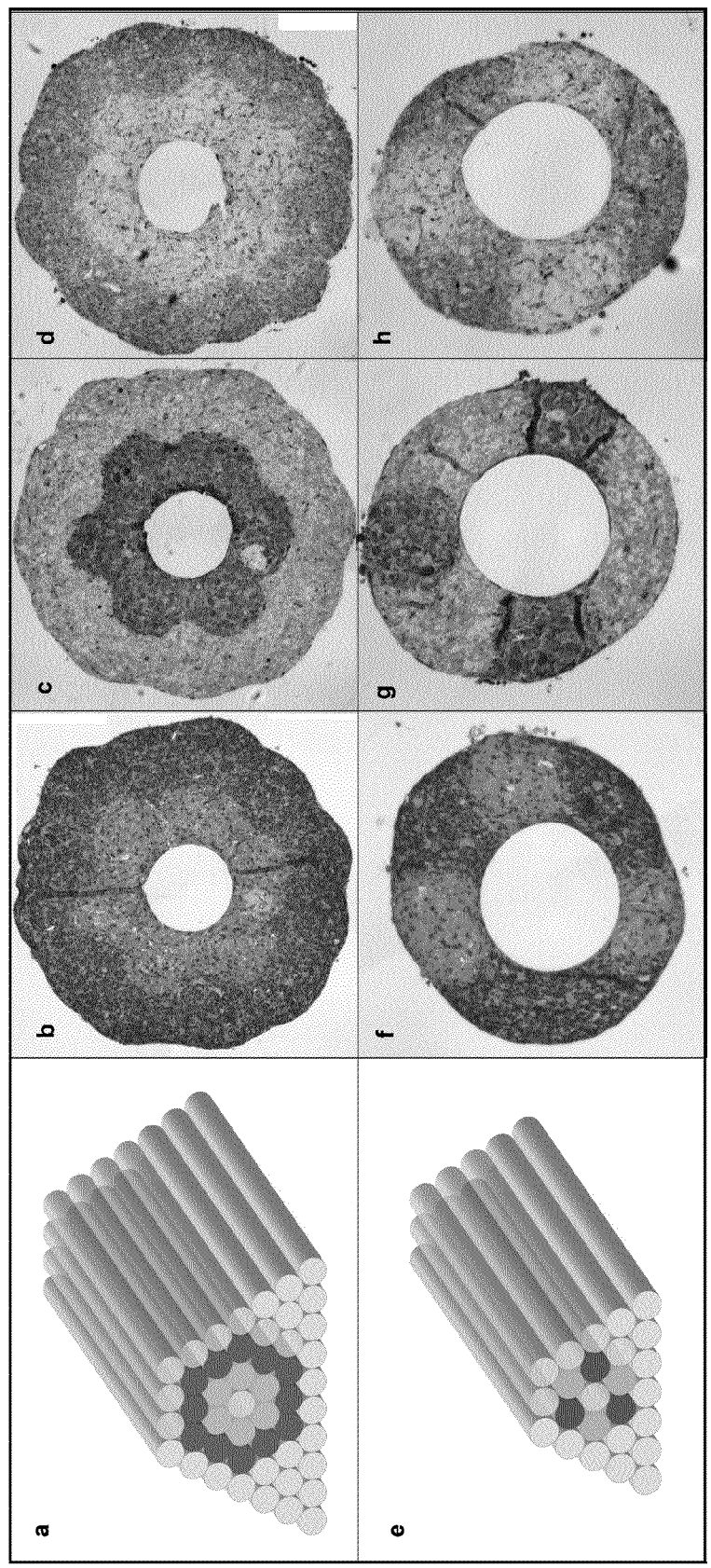
FIG. 17 includes a group of photographs illustrating fusion of a first set of multicellular bodies with a second set of multicellular bodies that have a cell type composition that is different from the composition of the multicellular bodies in the first set.

Next double-layered vascular tubes similar to vessels in the macrovasculature with a media and adventitia were constructed. For this both HUSMC and HSF cylinders were used as building blocks according to the pattern shown in FIG. 17. To show the versatility of the method, tubes were also engineered by alternatively depositing multicellular cylinders composed of HUSMCs and HSFs (FIG. 17E), a pattern that has no in vivo equivalent. Hematoxilin-eosin (H&E) (FIGS. 17B, 17F) and smooth muscle actin staining of HUSMCs (FIG. 17C, 17G) indicated a sharp boundary between the SMC and fibroblast layers or regions in the engineered constructs after 3 days of fusion. Caspase 3 staining revealed a few apoptotic cells in the wall of the tubular structure (FIGS. 17D, 17H). The more complex double-layered structure shown in FIGS. 17A-D required more time to fuse.

The single- and double-layered tubes ranged from about 0.9 mm to about 2.5 mm in outer diameter.

In the tissue engineering methods of the present invention, engineered constructs are built from cells only, the highest possible cell density is achieved. This is important as native vessels present a relatively cell-dense media layer with overlapping adjacent SMCs. The methods of the present invention use multicellular three-dimensional spheroids or cylinders as building blocks. Tissue cohesion through cell-cell interaction has previously been quantified by analogy with liquid systems, and reported that SMCs represent one of the most self-cohesive cell type ever observed. The analogy between multicellular assemblies and liquids provided a better understanding of some of the developmental morphogenetic processes employed here. Rounding or fusion of multicellular spheroids and cylinders described in this study are consistent with the physical understanding that, on a time scale of hours, tissues composed of motile and adhesive cells mimic highly viscous, incompressible liquids, a concept previously exploited for tissue-engineering.

Example 3

Use of Gelatin and/or Fibrin in Preparing Multicellular Bodies and a Three-Dimensional Fused Tubular Structure Human Aortic Smooth Muscle Cells (HASMCs) were purchased from Cascade Biologics (C-007-5C). HASMCs were grown in medium 231 supplemented with the Smooth Muscle Growth Supplement (SMGS). The HASMCs were grown on uncoated cell culture dishes and were maintained at 37° C. in a humidified atmosphere containing 5% $CO_2$.

The HASMCs were trypsinized, resuspended in tissue culture media, and centrifuged as described above in Examples 1 and 2. Following centrifugation, the tissue culture medium (i.e., the supernatant) is removed, and the cells (1 confluent Petri dish) were resuspended first in 100 μl of a solution of fibrinogen (50 mg/ml in 0.9% NaCl), and then 70 μl of a solution of gelatin (20% in phosphate buffered saline (PBS)) was added. The cell suspension was centrifuged again, the supernatant was removed, and the centrifuge tube containing the cell pellet was placed in a 37° C. water bath (a temperature at which the gelatin remains liquid), until the cell paste could be aspirated into a capillary tube. The cell paste was then aspirated into a capillary tube and placed in a ice cold solution of PBS for 15 minutes. During this step, the gelatin gelled and rendered the multicellular bodies sufficiently cohesive so that they could be printed immediately, without need for a second shaping step or a second incubating step. The multicellular bodies were deposited together with filler bodies onto a receiving surface as described above in Example 1 to form a desired three-dimensional biological structure (e.g., a tubular structure). A thrombin solution (50 U/ml) was added after each layer was deposited to convert the fibrinogen into fibrin. The three-dimensional structure was then placed in an incubator for maturation and fusion of the multicellular bodies to one another, as described above in Example 1.

Figure 18:
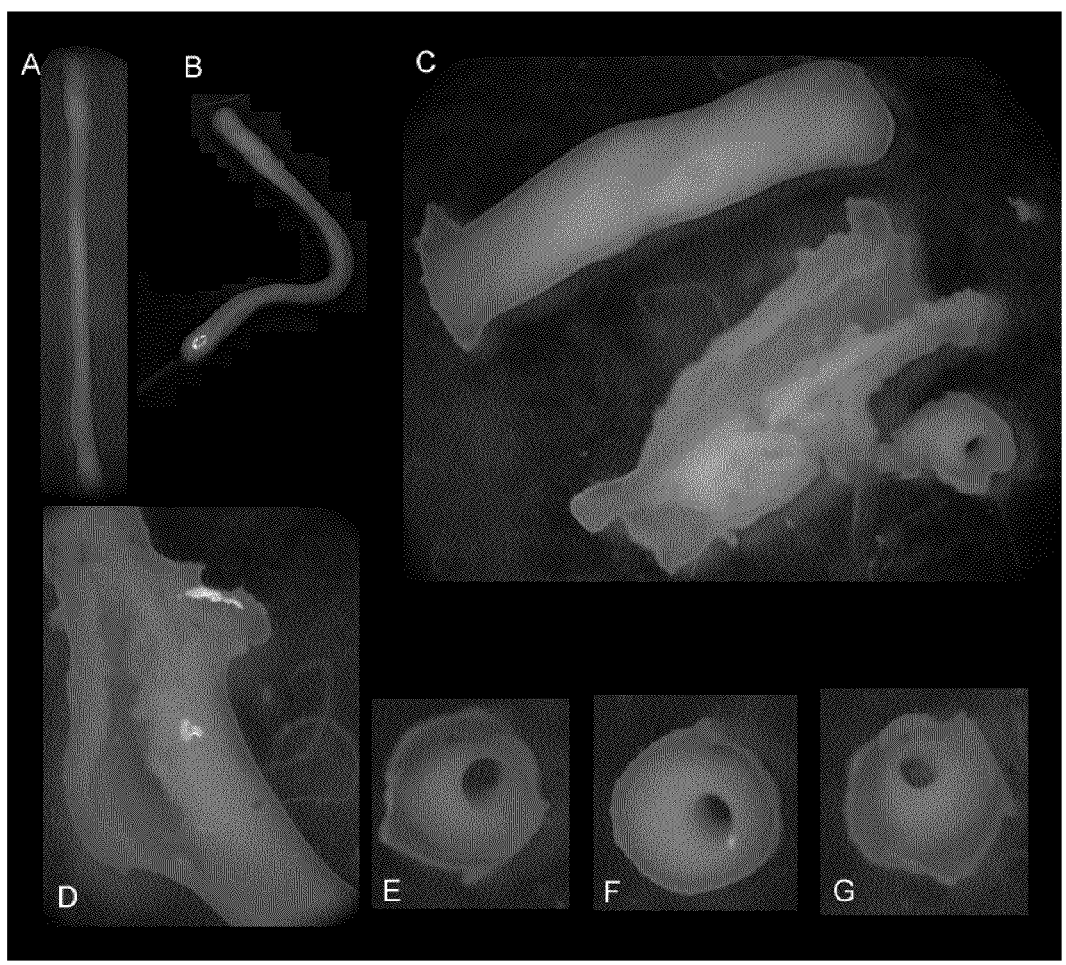
FIG. 18 includes a group of photographs illustrating a tubular engineered structure that includes gelatin and fibrin.

FIG. 18 shows some tubular structures created using this method, 12 days after deposition. FIG. 18A shows a tubular structure created using this method prior to removal of the agarose filler bodies, and FIGS. 18B-G show such structures following agarose removal. FIGS. 18C and 18D show tubular structures created using this method which have been cut open longitudinally to show the extent of fusion between the multicellular bodies. FIGS. 18E-18G are transverse views of tubular structures made using this method.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A three-dimensional structure comprising:
a plurality of multicellular bodies, each multicellular body comprising a plurality of living cells cohered to one another; and
a plurality of discrete filler bodies, each filler body comprising a biocompatible material that resists migration and ingrowth of cells from the multicellular bodies into the filler bodies and resists adherence of cells in the multicellular bodies to the filler bodies,
wherein the multicellular bodies and filler bodies are arranged in a pattern in which each multicellular body contacts at least one other multicellular body or at least one filler body.

2. The three-dimensional structure of claim 1, wherein the multicellular bodies each have an average cross-sectional area along their longitudinal axis in the range of about 7,850 square microns to about 360,000 square microns.

3. The three-dimensional structure of claim 1, wherein each of the multicellular bodies has a length of less than about 30 centimeters.

4. The three-dimensional structure of claim 1, wherein each multicellular body consists essentially of cells of a single cell type.

5. The three-dimensional structure of claim 1, wherein one or more of the multicellular bodies comprises a plurality of living cells of a first cell type and a plurality of living cells of a second cell type wherein the first and second cell types are different from one another.

6. The three-dimensional structure of claim 1, wherein the multicellular bodies are substantially uniform in shape.

7. The three-dimensional structure of claim 1, wherein the multicellular bodies are elongate in shape.

8. The three-dimensional structure of claim 1, wherein at least some of the multicellular bodies are arranged to form a sheet.

9. The three-dimensional structure of claim 1, wherein the multicellular bodies are substantially cylindrical and have substantially circular cross-sections.

10. The three-dimensional structure of claim 1, wherein the cohesion of the cells in each multicellular body is sufficiently strong to allow each multicellular body to support the weight of another multicellular body that is substantially identical to the multicellular body when said other multicellular body is on top of the multicellular body.

11. The three-dimensional structure of claim 1, wherein at least some of said plurality of multicellular bodies are arranged to form a tube-like structure and at least one of the filler bodies is inside the tube-like structure.

12. The three-dimensional structure of claim 5, wherein the one or more multicellular bodies further comprises a plurality of living cells of a third type, wherein each of the first, second and third cell types are different from the others of the first, second, and third cell types.

13. The three-dimensional structure of claim 12, wherein the first, second, and third cell types are each selected from the group consisting of endothelial cells, smooth muscle cells, and fibroblasts.

14. The three-dimensional structure of claim 6, wherein the filler bodies are substantially uniform in shape.

15. The three-dimensional structure of claim 7, wherein the filler bodies are elongate in shape.

16. The three-dimensional structure of claim 11, wherein the multicellular bodies include first and second sets of multicellular bodies, each multicellular body in said first set comprising endothelial cells, each multicellular body in said second set comprising smooth muscle cells; the multicellular bodies of the first set being arranged to form an inner layer substantially surrounding said at least one filler body, the multicellular bodies of the second set being arranged to form a second layer substantially surrounding said at least one filler body and the inner layer formed by the first set of multicellular bodies.

17. The three-dimensional structure of claim 16, wherein the multicellular bodies further include a third set of multicellular bodies, each multicellular body in said third set comprising fibroblasts, the multicellular bodies of the third set being arranged to form a layer substantially surrounding said at least one filler body, said inner layer formed by the first set of multicellular bodies, and said second layer formed by the second set of multicellular bodies, wherein a ratio of the number of fibroblasts to the number of non-fibroblasts in the third set is greater than a ratio of the number of fibroblasts to the number of non-fibroblasts in the first set or the second set.

18. The three-dimensional structure of claim 11, wherein the multicellular bodies include a first set of multicellular bodies, each multicellular body in said first set comprising a plurality of endothelial cells and a plurality of smooth muscle cells, the multicellular bodies of the first set being arranged to form an inner layer substantially surrounding said at least one filler body.

19. The three-dimensional structure of claim 18 further comprising a second set of multicellular bodies, each multicellular body in said second set comprising fibroblasts, the multicellular bodies of the second set being arranged to form a layer substantially surrounding said at least one filler body and the inner layer formed by the first set of multicellular bodies, wherein a ratio of the number of fibroblasts to the number of non-fibroblasts in the second set is greater than a ratio of the number of fibroblasts to the number of non-fibroblasts in the first set.

* * * * *